US012281980B2

(12) United States Patent
Wood et al.

(10) Patent No.: US 12,281,980 B2
(45) Date of Patent: Apr. 22, 2025

(54) MEASUREMENT OF NITROGEN FIXATION AND INCORPORATION

(71) Applicant: Pivot Bio, Inc., Berkeley, CA (US)

(72) Inventors: Kent Wood, Berkeley, CA (US); Russell Brown, Berkeley, CA (US); Jeremy Gage, Berkeley, CA (US); Rikke Rasmussen, Berkeley, CA (US); Paul Raine, Berkeley, CA (US); Sarah Bloch, Berkeley, CA (US); Alvin Tamsir, Berkeley, CA (US); Karsten Temme, Berkeley, CA (US); Bilge Ozaydin Eskiyenenturk, Berkeley, CA (US)

(73) Assignee: Pivot Bio, Inc., Berkeley, CA (US)

( * ) Notice: Subject to any disclaimer, the term of this patent is extended or adjusted under 35 U.S.C. 154(b) by 246 days.

(21) Appl. No.: 17/922,689

(22) PCT Filed: May 1, 2020

(86) PCT No.: PCT/US2020/031199
§ 371 (c)(1),
(2) Date: Nov. 1, 2022

(87) PCT Pub. No.: WO2021/221689
PCT Pub. Date: Nov. 4, 2021

(65) Prior Publication Data
US 2023/0175959 A1    Jun. 8, 2023

(51) Int. Cl.
*G01N 21/64* (2006.01)
*A01G 7/04* (2006.01)
(Continued)

(52) U.S. Cl.
CPC ......... *G01N 21/3563* (2013.01); *A01G 7/045* (2013.01); *A01G 9/18* (2013.01);
(Continued)

(58) Field of Classification Search
CPC .......... A01G 7/045; A01G 9/18; A01G 9/246; A01G 9/249; A01G 9/26; A01G 29/00;
(Continued)

(56) References Cited

U.S. PATENT DOCUMENTS

| 1,520,545 A | 12/1924 | Murphy |
| 4,782,022 A | 11/1988 | Puhler et al. |

(Continued)

FOREIGN PATENT DOCUMENTS

| AU | 636565 | 5/1993 |
| CA | 2051071 | 3/1993 |

(Continued)

OTHER PUBLICATIONS

Hardy et al., "The Acetylene-Ethylene Assay for N2 Fixation: Laboratory and Field Evaluation," Plant Physiology, Aug. 1968, 43(8):1185-1207.

(Continued)

*Primary Examiner* — Mark R Gaworecki
(74) *Attorney, Agent, or Firm* — Fish & Richardson P.C.

(57) ABSTRACT

Systems for plant culture include a chamber featuring one or more walls enclosing a spatial volume internal to the chamber, where the one or more walls include a surface for supporting a plant within the enclosed spatial volume, a gas delivery apparatus with at least one gas source, a nutrient delivery apparatus with a reservoir, a sampling apparatus connected to a port formed in the one or more walls, and a controller configured so that during operation of the system, the controller activates the nutrient delivery apparatus to deliver an aqueous growth medium to the plant, and activates the gas delivery apparatus to deliver into the enclosed spatial volume a mixture of isotopically-substituted gases. Also provided are methods of use of the system for mea- (Continued)

suring nitrogen in a plant and for identifying microbes capable of providing fixed nitrogen to a plant.

28 Claims, 9 Drawing Sheets

Specification includes a Sequence Listing.

(51) Int. Cl.
| | |
|---|---|
| A01G 9/18 | (2006.01) |
| A01G 9/24 | (2006.01) |
| A01H 1/00 | (2006.01) |
| A01H 4/00 | (2006.01) |
| A01N 63/20 | (2020.01) |
| G01N 21/3563 | (2014.01) |
| G01N 21/84 | (2006.01) |
| G01N 33/00 | (2006.01) |
| A01G 29/00 | (2006.01) |

(52) U.S. Cl.
CPC ............... *A01G 9/246* (2013.01); *A01H 1/12* (2021.01); *A01H 4/001* (2013.01); *A01N 63/20* (2020.01); *G01N 21/6456* (2013.01); *G01N 21/84* (2013.01); *G01N 33/0027* (2013.01); *G01N 33/0098* (2013.01); *A01G 9/249* (2019.05); *A01G 29/00* (2013.01); *G01N 2021/8466* (2013.01); *Y02A 40/25* (2018.01)

(58) Field of Classification Search
CPC .......... A01H 1/12; A01H 4/001; A01N 63/20; C07K 14/26; C12N 1/20; C12N 1/205; C12N 9/1241; C12R 2001/22; C12Y 207/07042; C12Y 207/07059; G01N 21/3563; G01N 21/6456; G01N 21/84; G01N 33/0027; G01N 33/0098; G01N 2021/8466; Y02A 40/25
See application file for complete search history.

(56) References Cited

U.S. PATENT DOCUMENTS

| | | | |
|---|---|---|---|
| 4,832,728 A | 5/1989 | Allan et al. |
| 5,071,743 A | 12/1991 | Slilaty et al. |
| 5,116,506 A | 5/1992 | Williamson et al. |
| 5,188,960 A | 2/1993 | Payne et al. |
| 5,229,291 A | 7/1993 | Nielsen et al. |
| 5,354,670 A | 10/1994 | Nickoloff et al. |
| 5,427,785 A | 6/1995 | Ronson et al. |
| 5,503,651 A | 4/1996 | Kloepper et al. |
| 5,610,044 A | 3/1997 | Lam et al. |
| 5,780,270 A | 7/1998 | Lesley |
| 5,789,166 A | 8/1998 | Bauer et al. |
| 5,877,012 A | 3/1999 | Estruch et al. |
| 5,880,275 A | 3/1999 | Fischhoff et al. |
| 5,916,029 A | 6/1999 | Smith et al. |
| 6,033,861 A | 3/2000 | Schaffer et al. |
| 6,033,874 A | 3/2000 | Baum et al. |
| 6,083,499 A | 7/2000 | Narva et al. |
| 6,107,279 A | 8/2000 | Estruch et al. |
| 6,114,148 A | 9/2000 | Seed et al. |
| 6,127,180 A | 10/2000 | Narva et al. |
| 6,137,033 A | 10/2000 | Estruch et al. |
| 6,218,188 B1 | 4/2001 | Cardineau et al. |
| 6,248,535 B1 | 6/2001 | Danenberg et al. |
| 6,326,351 B1 | 12/2001 | Donovan et al. |
| 6,340,593 B1 | 1/2002 | Cardineau et al. |
| 6,391,548 B1 | 5/2002 | Bauer et al. |
| 6,399,330 B1 | 6/2002 | Donovan et al. |
| 6,548,289 B1 | 4/2003 | Beynon et al. |
| 6,548,291 B1 | 4/2003 | Narva et al. |
| 6,596,509 B1 | 7/2003 | Bauer et al. |
| 6,624,145 B1 | 9/2003 | Narva et al. |
| 6,673,610 B2 | 1/2004 | Miyawaki et al. |
| 6,713,063 B1 | 3/2004 | Malvar et al. |
| 6,713,285 B2 | 3/2004 | Bauer et al. |
| 6,773,900 B2 | 8/2004 | Short et al. |
| 6,841,358 B1 | 1/2005 | Locht et al. |
| 6,949,626 B2 | 9/2005 | Donovan et al. |
| 6,962,705 B2 | 11/2005 | Malvar et al. |
| 7,064,249 B2 | 6/2006 | Corbin et al. |
| 7,070,982 B2 | 7/2006 | Malvar et al. |
| 7,084,331 B2 | 8/2006 | Isawa et al. |
| 7,105,332 B2 | 9/2006 | Abad et al. |
| 7,132,265 B2 | 11/2006 | Bauer et al. |
| 7,244,820 B2 | 7/2007 | Miles et al. |
| 7,329,736 B2 | 2/2008 | Abad et al. |
| 7,378,499 B2 | 5/2008 | Abad et al. |
| 7,385,107 B2 | 6/2008 | Donovan et al. |
| 7,449,552 B2 | 11/2008 | Abad et al. |
| 7,462,760 B2 | 12/2008 | Abad et al. |
| 7,470,427 B2 | 12/2008 | Cocking |
| 7,476,781 B2 | 1/2009 | Abad et al. |
| 7,485,451 B2 | 2/2009 | Vandergheynst et al. |
| 7,491,698 B2 | 2/2009 | Hey et al. |
| 7,491,869 B2 | 2/2009 | Abad et al. |
| 7,504,229 B2 | 3/2009 | Donovan et al. |
| 7,615,686 B2 | 11/2009 | Miles et al. |
| 7,803,943 B2 | 9/2010 | Mao et al. |
| 7,858,849 B2 | 12/2010 | Cerf et al. |
| 7,923,602 B2 | 4/2011 | Carozzi et al. |
| 8,076,142 B2 | 12/2011 | Huang et al. |
| 8,084,416 B2 | 12/2011 | Sampson et al. |
| 8,084,418 B2 | 12/2011 | Hey et al. |
| 8,137,665 B2 | 3/2012 | Cocking |
| 8,236,757 B2 | 8/2012 | Carozzi et al. |
| 8,237,020 B2 | 8/2012 | Miles et al. |
| 8,268,584 B1 | 9/2012 | Hardwood et al. |
| 8,304,604 B2 | 11/2012 | Lira et al. |
| 8,304,605 B2 | 11/2012 | Lira et al. |
| 8,319,019 B2 | 11/2012 | Abad et al. |
| 8,334,366 B1 | 12/2012 | Hughes et al. |
| 8,334,431 B2 | 12/2012 | Sampson et al. |
| 8,377,671 B2 | 2/2013 | Cournac et al. |
| 8,481,026 B1 | 7/2013 | Woodruff et al. |
| 8,513,494 B2 | 8/2013 | Wu et al. |
| 8,530,411 B2 | 9/2013 | Cerf et al. |
| 8,575,433 B2 | 11/2013 | Cerf et al. |
| 8,686,233 B2 | 4/2014 | Cerf et al. |
| 8,759,619 B2 | 6/2014 | Sampson et al. |
| 8,795,965 B2 | 8/2014 | Zjang |
| 8,802,933 B2 | 8/2014 | Abad et al. |
| 8,802,934 B2 | 8/2014 | Abad et al. |
| 9,150,851 B2 | 10/2015 | Wigley et al. |
| 9,321,697 B2 | 4/2016 | Das et al. |
| 9,487,451 B2 | 11/2016 | Doty et al. |
| 9,512,431 B2 | 12/2016 | Mirsky et al. |
| 9,657,298 B2 | 5/2017 | Soto et al. |
| 9,796,957 B2 | 10/2017 | Barney et al. |
| 9,957,509 B2 | 5/2018 | Mirsky et al. |
| 9,975,817 B2 | 5/2018 | Temme et al. |
| 9,994,557 B2 | 6/2018 | Davidson et al. |
| 10,384,983 B2 | 8/2019 | Temme et al. |
| 10,525,318 B2 | 1/2020 | Dougherty |
| 10,556,839 B2 | 2/2020 | Temme et al. |
| 10,662,432 B2 | 5/2020 | Mirsky et al. |
| 10,919,814 B2 | 2/2021 | Temme et al. |
| 10,934,226 B2 | 3/2021 | Temme et al. |
| 10,968,446 B2 | 4/2021 | Zhao et al. |
| 2004/0197916 A1 | 10/2004 | Carozzi et al. |
| 2004/0197917 A1 | 10/2004 | Carozzi et al. |
| 2004/0210964 A1 | 10/2004 | Carozzi et al. |
| 2004/0210965 A1 | 10/2004 | Carozzi et al. |
| 2004/0216186 A1 | 10/2004 | Carozzi et al. |
| 2004/0235663 A1 | 11/2004 | Cocking |
| 2004/0241847 A1 | 12/2004 | Okuyama et al. |
| 2004/0250311 A1 | 12/2004 | Carozzi et al. |
| 2005/0081262 A1 | 4/2005 | Cook et al. |
| 2005/0266541 A1 | 12/2005 | Dillon |
| 2006/0033867 A1 | 2/2006 | Krisko et al. |
| 2006/0096918 A1 | 5/2006 | Semmens |
| 2006/0112447 A1 | 5/2006 | Bogdanova et al. |

(56) References Cited

U.S. PATENT DOCUMENTS

| | | |
|---|---|---|
| 2006/0127988 A1 | 6/2006 | Wood et al. |
| 2006/0191034 A1 | 8/2006 | Baum |
| 2006/0243011 A1 | 11/2006 | Someus |
| 2007/0249018 A1 | 10/2007 | Vemuri et al. |
| 2008/0295207 A1 | 11/2008 | Baum et al. |
| 2008/0311632 A1 | 12/2008 | Figge et al. |
| 2009/0105076 A1 | 4/2009 | Stewart et al. |
| 2009/0137390 A1 | 5/2009 | Triplett |
| 2009/0144852 A1 | 6/2009 | Tomso et al. |
| 2009/0152195 A1 | 6/2009 | Rodgers et al. |
| 2009/0162477 A1 | 6/2009 | Nadel |
| 2009/0258404 A1 | 10/2009 | Mikkelsen et al. |
| 2009/0308121 A1 | 12/2009 | Reddy et al. |
| 2010/0005543 A1 | 1/2010 | Sampson et al. |
| 2010/0017914 A1 | 1/2010 | Hart et al. |
| 2010/0028870 A1 | 2/2010 | Welch et al. |
| 2010/0184038 A1 | 7/2010 | Boddy et al. |
| 2010/0197592 A1 | 8/2010 | Heinrichs |
| 2010/0267147 A1 | 10/2010 | Qiao |
| 2010/0298211 A1 | 11/2010 | Carozzi et al. |
| 2011/0023184 A1 | 1/2011 | Desai et al. |
| 2011/0064710 A1 | 3/2011 | Benson et al. |
| 2011/0104690 A1 | 5/2011 | Yu et al. |
| 2011/0263488 A1 | 10/2011 | Carozzi et al. |
| 2012/0015806 A1 | 1/2012 | Paikray et al. |
| 2012/0107889 A1 | 5/2012 | Doty et al. |
| 2012/0192605 A1 | 8/2012 | McSpadden Gardener et al. |
| 2012/0266332 A1 | 10/2012 | Kuykendall |
| 2012/0278954 A1 | 11/2012 | Bowen et al. |
| 2012/0284813 A1 | 11/2012 | Oliver et al. |
| 2012/0311745 A1 | 12/2012 | Meade et al. |
| 2012/0311746 A1 | 12/2012 | Meade et al. |
| 2012/0317681 A1 | 12/2012 | Meade et al. |
| 2012/0317682 A1 | 12/2012 | Meade et al. |
| 2012/0324605 A1 | 12/2012 | Meade et al. |
| 2012/0324606 A1 | 12/2012 | Meade et al. |
| 2012/0331589 A1 | 12/2012 | Meade et al. |
| 2012/0331590 A1 | 12/2012 | Meade et al. |
| 2013/0116170 A1 | 5/2013 | Graser et al. |
| 2013/0126428 A1 | 5/2013 | Jones et al. |
| 2013/0167268 A1 | 6/2013 | Narva et al. |
| 2013/0167269 A1 | 6/2013 | Narva et al. |
| 2014/0011261 A1 | 1/2014 | Wang et al. |
| 2014/0155283 A1 | 6/2014 | Venkateswaran et al. |
| 2014/0182018 A1 | 6/2014 | Lang et al. |
| 2014/0223598 A1 | 8/2014 | Sampson et al. |
| 2014/0223599 A1 | 8/2014 | Sampson et al. |
| 2014/0230504 A1 | 8/2014 | Finlayson et al. |
| 2014/0273226 A1 | 9/2014 | Wu |
| 2014/0301990 A1 | 10/2014 | Gregory et al. |
| 2014/0329326 A1 | 11/2014 | Mirsky et al. |
| 2014/0336050 A1 | 11/2014 | Soto et al. |
| 2015/0080261 A1 | 3/2015 | Wigley et al. |
| 2015/0101373 A1 | 4/2015 | Munusamy et al. |
| 2015/0128670 A1 | 5/2015 | Das |
| 2015/0237807 A1 | 8/2015 | Valiquette |
| 2015/0239789 A1 | 8/2015 | Kang et al. |
| 2015/0315570 A1 | 11/2015 | Zhao et al. |
| 2016/0174570 A1 | 6/2016 | Vukanovic et al. |
| 2016/0264929 A1 | 9/2016 | Barney et al. |
| 2016/0292355 A1 | 10/2016 | Lou et al. |
| 2016/0295868 A1 | 10/2016 | Jones et al. |
| 2017/0086402 A1 | 3/2017 | Meadows-Smith et al. |
| 2017/0119690 A1 | 5/2017 | Hansen et al. |
| 2017/0152519 A1 | 6/2017 | Mirsky et al. |
| 2017/0267997 A1 | 9/2017 | Nicol et al. |
| 2017/0367349 A1 | 12/2017 | Gruver et al. |
| 2018/0002243 A1 | 1/2018 | Temme et al. |
| 2018/0020671 A1 | 1/2018 | Bioconsortia |
| 2018/0065896 A1 | 3/2018 | Ibema et al. |
| 2018/0073028 A1 | 3/2018 | Mirsky et al. |
| 2018/0273437 A1 | 9/2018 | Temme et al. |
| 2018/0290942 A1 | 10/2018 | Voigt et al. |
| 2018/0297905 A1 | 10/2018 | Temme et al. |
| 2018/0297906 A1 | 10/2018 | Temme et al. |
| 2019/0039964 A1 | 2/2019 | Temme et al. |
| 2019/0144352 A1 | 5/2019 | Temme et al. |
| 2020/0087221 A1 | 3/2020 | Temme et al. |
| 2020/0115715 A1 | 4/2020 | Mirsky et al. |
| 2020/0299637 A1 | 9/2020 | Voigt et al. |
| 2020/0308594 A1 | 10/2020 | Tamsir et al. |
| 2020/0331820 A1 | 10/2020 | Tamsir et al. |
| 2021/0009483 A1 | 1/2021 | Temme et al. |
| 2021/0029928 A1 | 2/2021 | Gilsinger et al. |
| 2021/0163374 A1 | 6/2021 | Bioch et al. |
| 2021/0214282 A1 | 7/2021 | Temme et al. |
| 2021/0315212 A1 | 10/2021 | Rezaei et al. |
| 2022/0017911 A1 | 1/2022 | Temme et al. |
| 2022/0079163 A1 | 3/2022 | Reisinger et al. |

FOREIGN PATENT DOCUMENTS

| | | |
|---|---|---|
| CN | 1289852 | 4/2001 |
| CN | 1500801 | 6/2004 |
| CN | 1552846 | 12/2004 |
| CN | 1746304 | 3/2006 |
| CN | 101880676 | 11/2010 |
| CN | 101899430 | 12/2010 |
| CN | 102041241 | 5/2011 |
| CN | 102417882 | 4/2012 |
| CN | 102690808 | 9/2012 |
| CN | 103451130 | 12/2013 |
| CN | 104136599 | 11/2014 |
| CN | 104204211 | 12/2014 |
| CN | 106086042 | 11/2016 |
| CN | 107047265 | 8/2017 |
| CN | 108271339 | 7/2018 |
| CN | 113268923 | 8/2021 |
| EA | 002757 | 8/2002 |
| EP | 0256889 | 2/1988 |
| EP | 0292984 | 11/1988 |
| EP | 0339830 | 11/1989 |
| EP | 1535913 | 6/2005 |
| EP | 2186890 | 5/2010 |
| EP | 3056569 | 8/2016 |
| EP | 3322679 | 5/2018 |
| FR | 2254409 | 7/1975 |
| FR | 2910230 | 6/2008 |
| JP | H01-225483 | 9/1989 |
| JP | H02-131581 | 5/1990 |
| JP | 2009-232721 | 10/2009 |
| JP | 2014-096996 | 5/2014 |
| JP | 2015-037385 | 2/2015 |
| JP | 2015-042633 | 3/2015 |
| JP | 2015-113274 | 6/2015 |
| JP | 2015-518023 | 6/2015 |
| JP | 2015-519352 | 7/2015 |
| JP | 2016183931 | 10/2016 |
| WO | WO 1987/004182 | 7/1987 |
| WO | WO 1993/005154 | 3/1993 |
| WO | WO 1998/010088 | 3/1998 |
| WO | WO 1999/009834 | 3/1999 |
| WO | WO 2000/057183 | 9/2000 |
| WO | WO 2001/007567 | 2/2001 |
| WO | WO 2003/010535 | 2/2003 |
| WO | WO 2004/074462 | 9/2004 |
| WO | WO 2005/021585 | 3/2005 |
| WO | WO 2005/038032 | 4/2005 |
| WO | WO 2006/005100 | 1/2006 |
| WO | WO 2006/083891 | 8/2006 |
| WO | WO 2006/098225 | 9/2006 |
| WO | WO 2006/119457 | 11/2006 |
| WO | WO 2007/027776 | 3/2007 |
| WO | WO 2009/060012 | 5/2009 |
| WO | WO 2009/091557 | 7/2009 |
| WO | WO 2010/080184 | 7/2010 |
| WO | WO 2011/099019 | 8/2011 |
| WO | WO 2011/099024 | 8/2011 |
| WO | WO 2011/103247 | 8/2011 |
| WO | WO 2011/103248 | 8/2011 |
| WO | WO 2011/154960 | 12/2011 |
| WO | WO 2012/139004 | 10/2012 |
| WO | WO 2012/154651 | 11/2012 |
| WO | WO 2012/174271 | 12/2012 |

(56) References Cited

FOREIGN PATENT DOCUMENTS

| | | |
|---|---|---|
| WO | WO 2013/076687 | 5/2013 |
| WO | WO 2013/132518 | 9/2013 |
| WO | WO 2013/176777 | 11/2013 |
| WO | WO 2014/042517 | 3/2014 |
| WO | WO 2014/071182 | 5/2014 |
| WO | WO 2014/201044 | 12/2014 |
| WO | WO 2015/006675 | 1/2015 |
| WO | WO 2016/016629 | 2/2016 |
| WO | WO 2016/016630 | 2/2016 |
| WO | WO 2016/100727 | 6/2016 |
| WO | WO 2016/146955 | 9/2016 |
| WO | WO 2016/178580 | 11/2016 |
| WO | WO 2016/179046 | 11/2016 |
| WO | WO 2016/181228 | 11/2016 |
| WO | WO 2016/191828 | 12/2016 |
| WO | WO 2016/200987 | 12/2016 |
| WO | WO 2017/011602 | 1/2017 |
| WO | WO 2017/042833 | 3/2017 |
| WO | WO 2017/062412 | 4/2017 |
| WO | WO 2017/069717 | 4/2017 |
| WO | WO 2017/112827 | 6/2017 |
| WO | WO 2017/203440 | 11/2017 |
| WO | WO 2018/081543 | 5/2018 |
| WO | WO 2018/132774 | 7/2018 |
| WO | WO 2018/133774 | 7/2018 |
| WO | WO 2019/032926 | 2/2019 |
| WO | WO 2019/084342 | 5/2019 |
| WO | WO 2019/140125 | 7/2019 |
| WO | WO 2020/006064 | 1/2020 |
| WO | WO 2020/006246 | 1/2020 |
| WO | WO 2020/014498 | 1/2020 |
| WO | WO 2020/023630 | 1/2020 |
| WO | WO 2020/061363 | 3/2020 |
| WO | WO 2020/092940 | 5/2020 |
| WO | WO 2020/118111 | 6/2020 |
| WO | WO 2020/146372 | 7/2020 |
| WO | WO 2020/163251 | 8/2020 |
| WO | WO 2020/190363 | 9/2020 |
| WO | WO 2020/191201 | 9/2020 |
| WO | WO 2020/219893 | 10/2020 |
| WO | WO 2020/219932 | 10/2020 |
| WO | WO 2021/113352 | 6/2021 |
| WO | WO 2021/146209 | 7/2021 |
| WO | WO 2021/221689 | 11/2021 |

OTHER PUBLICATIONS

International Search Report and Written Opinion in International Application No. PCT/US2023/011735, mailed on May 15, 2023, 24 pages.
Islam et al., "Isolation and Identification of Plant Growth Promoting Rhizobacteria from Cucumber Rhizosphere and Their Effect on Plant Growth Promotion and Disease Suppression," Front Microbiol., Feb. 2, 2016, 6:1360.
Morel et al., "Fate of genetically modified microorganisms in the corn rhizosphere," Current Microbiology, Jun. 18, 1989:355-360.
Baudoin et al., "Impact of artificial root exudates on the bacterial community structure in bulk soil and maize rhizosphere," Soil Biology and Biochemistry, Sep. 2003, 35(9):1183-1192.
US 8,476,226, 11/1999, Koenck (withdrawn)
"New Plant Breeding Techniques," Science Council of Japan, retrieved from URL <http://www.scj.go.jp/ja/info/kohyo/pdf/kohyo-22-h140826.pdf>, Aug. 26, 2014, 88 pages (partial English translation).
"T7 RNA Polymerase Expression System for Bacillus megaterium," T7 RNAP Expression System Handbook, Jan. 2010, © MoBiTec GmbH, 18 pages.
40 CFR 725.3 U.S. Government Publishing Office (Jul. 1, 2010) https://www.gpo.gov/fdsys/pkg/CFR-2010-title40-vol30/pdf/CFR-2010-title40-vol30-sec725-3.pdf (Year: 2010), 3 pages.
Aita, T., Husimi, Y. "Adaptive walks by the fittest among finite random mutants on a Mt. Fugi-type fitness landscape," J. Theor. Biol. 193:383-405 (1998).

Alper et al., "Tuning genetic control through promoter engineering," Proc Natl Acad Sci U SA, 2005, 102(36):12678-12683.
Altschul et al. "Basic local alignment search tool," J Mol Biol., 1990, 215(3):403-441.
Altschul et al., "Gapped BLAST and PSI-BLAST: a new generation of protein database search programs," Nucleic Acids Res., 1997, 25:3389-3402.
Amalraj et al., "Effect of Polymeric Additives, Adjuvants, Surfactants on Survival, Stability and Plant Growth Promoting Ability of Liquid Bioinoculants," J. Plant Physiol Pathol, Jan. 2013:2, 6 pages.
Ambrosio et al., "Metabolic engineering of a diazotrophic bacterium improves ammonium release and biofertilization of plants and microalgae," Metab Eng., Mar. 2017, 40:59-68.
An et al., "Constitutive expression of the nifA gene activates associative nitrogen fixation of Enterobacter gergoviae 57-7, an opportunistic endophytic diazotroph," Journal of Applied Microbiology, 2007, 103(3):613-620.
Andersen et al., "Energetics of biological nitrogen fixation: determination of the ratio of formation of H2 to NH4+ catalysed by nitrogenase of Klebsiella pneumoniae in vivo," J Gen Microbial., Nov. 1977, 103(1):107-22.
Andersen et al., "Herpesvirus-mediated gene delivery into the rat brain: specificity and efficiency of the neuron-specific enolase promoter," Cell. Mol. Neurobiol., 1993, 13:503-515.
Anderson et al., "BglBricks: A flexible standard for biological part assembly," Journal of Biological Engineering, Apr. 2010:1, 12 pages.
Andrews et al., "Use of Nitrogen Fixing Bacteria Inoculants as a Substitute for Nitrogen Fertiliser for Dryland Graminaceous Crops: Progress Made, Mechanisms of Action and Future Potential," Symbiosis, 2003, 34:21 pages.
Andrianantoandro et al., "Synthetic biology: new engineering rules for an emerging discipline," Mol. Syst. Biol., Feb. 2006:2006.0028, 14 pages.
Arbuthnot et al., "In vitro and in vivo hepatoma cell-specific expression of a gene transferred with an adenoviral vector," Hum Gene Ther., 1996, 7(13):1503-1514.
Arnold et al., "Nucleotide sequence of a 24,206-base-pair DNA fragment carrying the entire nitrogen fixation gene cluster of Klebsiella pneumoniae," J. Mol. Biol., 1988, 203(3):715-738.
Arriel-Elias et al., "Shelf-life enhancement of plant growth promoting rhizobacteria using a simple formulation screening method," African Journal of Microbiology Research, Feb. 2018, 12(5):115-126.
Arsene et al., "Modulation of NifA activity by PII in Azospirillum brasilense: Evidence for a Regulatory role of the NifA N-Terminal Domain," Journal of Bacteriology, Aug. 1996, 178(16):4830-4838.
Austin et al. "Characterisation of the Klebsiella pneumoniae nitrogen-fixation regulatory proteins NIFA and NIFL in vitro, " Eur J Biochem., 1990, 187(2):353-360.
Ausubel et al., "Glutamine Synthetase Mutations Which Affect Expression of Nitrogen Fixation Genes in Klebsiella pneumoniae," J Bacteriol, Nov. 1979, 140(2):597-606.
Bageshwar et al., "An Environmentally Friendly Engineered Azotobacter Strain That Replaces a Substantial Amount of Urea Fertilizer while Sustaining the Same Wheat Yield," Appl Environ Microbial., Aug. 2017, 83(15):e00590-17.
Bali et al., "Excretion of Ammonium by a nifL Mutant of Azotobacter vinelandii fixing Nitrogen," Applied and Environmental Microbiology, May 1992, 58(5):1711-1718.
Barney et al., "Gene deletions resulting in increased nitrogen release by azotobacter vinelandii: application of a novel nitrogen biosensor," Appl. Environ. Microbial., Jul. 2015, 81(13):4316-4328.
Barney et al., "Transcriptional analysis of an Ammonium-excreting stain of azotobacter vinelandii deregulated for nitrogen fixation," Appl. Environ. Microbial. Jul. 2017, 83(20):1-22.
Barrangou et al., "Exploiting CRISPR-Cas immune systems for genome editing in bacteria," Curr. Opin. Biotechnol., Nov. 2016, 37:61-68.
Batista et al. "Manipulating nitrogen regulation in diazotrophic bacteria for agronomic benefit," Biochem Soc Trans., 2019, 47(2):603-614.

(56) References Cited

OTHER PUBLICATIONS

Batzer et al., "Enhanced evolutionary PCR using oligonucleotides with inosine at the 3'-termins," Nucleic Acid Res., 1991, 19:5081, 1 page.
Baum et al., "Control of coleopteran insect pests through RNA interference," Nature Biotechnology, Nov. 2007, 25(11):1322-1326.
Bayer et al., "Synthesis of Methyl Halides from Biomass Using Engineered Microbes," J. Am. Chem. Soc., 2009, 131(18):6508-6515.
Bender et al., "Regulatory mutations in the Klebsiella aerogenes structural gene for glutamine synthetase," J Bacteriol., Oct. 1977, 132(1):100-105.
Beringer et al., "Genetic engineering and nitrogen fixation," Biotech. Gen. Eng. Rev., Feb. 1984, 1(1):65-88.
Berninger et al., "Maintenance and assessment of cell viability in formulation of non-sporulating bacterial inoculants," Microb. Biotechnol., Mar. 2018, 11(2):277-301 (2018); doi: 10.1111/1751-7915.12880.
Beynon et al., "The nif promoters of Klebsiella pneumoniae have a characteristic primary structure," Cell, 1983, 34(2):665-671.
Biggins et al., "Metabolites from the induced expression of cryptic single operons found in the genome of Burkolderia pseudomallei," JACS, 2011, 133:1638-1641.
Bikard et al., "The synthetic integron: an in vivo genetic shuffling device," Nucleic Acids Res., 2010, 38(15):e153, 7 pages.
Bilitchenko et al., "Eugene—a domain specific language for specifying and constraining synthetic biological parts, devices, and systems," PLoS One, Apr. 2011, 6(4):e18882, 12 pages.
Bittner et al., "RpoS and RpoN are involved in the growth-dependent regulation of rfaH transcription and O antigen expression in Salmonella enterica serovar typhi," Microbial Pathogenesis, Jan. 2004, 36(1):19-24.
Blanco et al., "Sequence and molecular analysis of the nifL gene of Azotobacter vine landii." Mol Microbial. Aug. 1993, 9(4):869-79.
Blast.ncbi.nlm.nih.gov, [online], "BLAST. Basic local alignment search tool," 2021, retrieved on Apr. 8, 2021, retrieved from URL<https://blast.ncbi.nlm.nih.gov/Blast.cgi>, 3 pages.
Bloch et al., "Biological nitrogen fixation in maize: optimizing nitrogenase expression in a root-associated diazotroph," Journal of Experimental Botany, Jul. 2020, 71(15):4591-4603.
Bonde et al., "MODEST: a web-based design tool for oligonucleotide-mediated genome engineering and recombineering," Nucleic Acids Res., 2014, 42(W1):W408-W415.
Boshart et al. "A very strong enhancer is located upstream of an immediate early gene of human cytomegalovirus," Cell, 1985, 41(2):521-30.
Bosmans et al., "Sea anemone venom as a source of insecticidal peptides acting on voltage-gated Na+ channels," Toxicon, Mar. 2007, 49(4):550-560.
Bosworth et al., "Alfalfa yield response to inoculation with recombinant strains of Rhizobium meliloti with an extra of dctABD and/or modified nifA expression," Appl Environ Microbial. Oct. 1994, 60(10):3815-32.
Boyle et al., "Tools for genome-wide strain design and construction," Curr Opin Biotechnol., 2012, 23(5):666-671.
Brandl et al., "Salmonella interactions with plants and their associated microhiota," Phytopathology, 2013, 103:316-325.
Brewin et al., "The Basis of Ammonium release in nifL Mutants of Azotobacter vinelandii," Journal of Bacteriology, Dec. 1999, 181(23):7356-7362.
Buchanan-Wollaston et al., "Role of the nifA gene product in the regulation of nif expression in Klebsiella pneumoniae," Nature., Dec. 1981, 294(5843):776-8.
Buck et al., "Frameshifts close to the Klebsiella pneumoniae nifH promoter prevent multicopy inhibition by hybrid nifH plasmids," Mol. Gen. Genet., 1987, 207(2-3):492-498.
Buckley Lab NifH database, retrieved via WayBack Machine from URL <http://www.css.cornell.edu/faculty/buckley/nifh.htm>, available on or before Jan. 10, 2018, 2 pages.

Buddrus-Schiemann et al., "Root colonization by Pseudomonas sp. DSMZ 13134 and impact on the indigenous rhizosphere bacterial community of barley." Microb Ecol. Aug. 2010, 60(2):381-393.
Burris et al., "Nitrogenases," J. Biol. Chem., 1991, 266(15):9339-9342.
Cardinale et al., "Contextualizing context for synthetic biology identifying causes of failure of synthetic biological systems," Biotechnol. J., Jul. 2012:856-866.
Carr et al., "Enhanced multiplex genome engineering through co-operative oligonucleotide coselection," Nucleic Acids Res., 2012, 40(17):e132, 11 pages.
cera-gmc.org [online], "GM Crop Database," Center for Environmental Risk Assessment (CERA), 2010, retrieved from URL <http://ucbiotech.org/biotech_info/PDFs/Center_for_Environmental_Risk_Assessment_CERA_2011_GM_Crop_Database.pdf>, 1 page.
Ceranic et al., "Preparation of uniformly labelled 13C- and 15N-plants using customised growth chambers, " Plant Methods, Apr. 2020, 16(1), 15 pages.
Cerestrust.org [online]. "Year-end Final Report" Young et al., Ceres Trust, retrieved from URL <https://cerestrust.org/wpcontent/uploads/NitrogenFixingBacteriaCorn.pdf>, 2012, 9 pages.
Chakroun et al., "Bacterial Vegetative Insecticidal Proteins (Vip) from Entomopathogenic Bacteria," Microbiol Mol Biol Rev., Mar. 2016, 80(2):329-50.
Chan et al., "Refactoring bacteriophage T7," Molecular Systems Biology, 2005, 1(1):E1-E10.
Chen et al., "An automated growth enclosure for metabolic labeling of Arabidopsis thaliana with 13C-carbon dioxide—an in vivo labeling system for proteomics and metabolics research," Proteome Science, Feb. 2011, 9(1):9.
Chen et al., "Characterization of 582 natural and synthetic terminators and quantification of their design constraints," Nat. Methods, Oct. 2013:659-664.
Chen et al., "Complete genome sequence of Kosakonia sacchari type strain SP1 T," Stand Genomic Sci., Jun. 15, 2014, 9(3):1311-1318.
Chen et al., "Expression of rat bone sialoprotein promoter in transgenic mice," J Bone Miner Res., May 1996, 11(5):654-64.
Chiang et al., "Mutagenic Oligonucleotide-directed PCR Amplification (Mod-PCR): An Efficient Method for Generating Random Base Substitution Mutations in a DNA sequence element," PCR methods and applications, Feb. 1993:210-217.
Chin, "Programming and engineering biological networks," Curr. Opin. Struct. Biol., 2006, 16:551-556.
Choi et al., "A Tn7-based broad-range bacterial cloning and expression system," Nat Methods, Jun. 2005, 2(6):443-8.
Choudhary et al., "Interactions of Bacillus spp. and Plants—With Special Reference to Induced Systemic Resistance (ISR)," Microbiological Research, 2009, 164(5):493-513.
Clancy et al., "The domains carrying the opposing activities in adenylyltransferase are separated by a central regulatory domain," FEBS Journal, 2007, 274(11):2865-2877.
Cobb et al., "Directed evolution: an evolving and enabling synthetic biology tool," Curr Opin Chem Biol., Aug. 2012, 16(3-4):285-91.
Cohen, "In vitro Tomato Fruit Cultures Demonstrate a Role for Indole-3-acetic Acid in Regulating Fruit Ripening," J. Amer. Soc. Hort. Sci., 1996, 121(3):520-524.
Colby, "Calculating Synergistic and Antagonistic Responses of Herbicide Combinations," Weeds, Jan. 1967, 15(1):20-22, 4 pages.
Colebatch et al., "Symbiotic nitrogen fixation research in the postgenomics era," New Phytologist., 2002, 153(1):37-42.
Colnaghi et al., "Lethality of glnD null mutations in Azotobacter vinelandii is suppressible by prevention of glutamine synthetase adenylylation," Microbiology, May 2001, 147(Pt 5):1267-76.
Colnaghi et al., "Strategies for increased ammonium production in free-living or plant associated nitrogen fixing bacteria," Plant and Soil, Nov. 1997, 194:145-154.
Compant et al., "A review on the plant microbiome: Ecology, functions, and emerging trends in microbial application," Journal of Advanced Research, Sep. 19, 2019:29-37.

(56) References Cited

OTHER PUBLICATIONS

Conniff, "Microbes Help Grow Better Crops," (Sep. 1, 2013) Scientific American. Retrieved from URL <https://www.scientificamerican.com/article/microbes-helpgrow-better-crops/>, (Year: 2013), 7 pages.

Contreras et al., "The product of the nitrogen fixation regulatory gene nfrX of Azotobacter vinelandii is functionally and structurally homologous to the uridylyltransferase encoded by glnD in enteric bacteria." J Bacterial. Dec. 1991, 173(24):7741-7749.

Cornelis et al., "The type III secretion injectisome," Nature Reviews Microbiology, 2006, 4(11):811-825.

Costerton et al., "Microbial Biofilms," Annu. Rev. Microbial., Oct. 1995, 49:711-745.

Crameri et al., "Molecular evolution of an arsenate detoxification pathway by DNA shuffling," Nat. Biotechnol., 1997, 15:436-438.

Crickmore et al., "Revision of the Nomenclature for the Bacillus thuringiensis Pesticidal Crystal Proteins," Microbiol Mol Biol Rev., Sep. 1998, 62(3):807-813.

Crook et al., "Re-engineering multicloning sites for function and convenience," Nucl. Acids Res., 2011, 39:e92, 10 pages.

Curatti et al., "Genes required for rapid expression of nitrogenase activity in Azotobacter vinelandii," PNAS, May 2005, 102(18):6291-6296.

Czar et al., "Gene synthesis demystified," Trends Biotechnol, 2009, 27(2):63-72.

Da Silva et al., "Survival of endophytic bacteria in polymer-based inoculants and efficiency of their application to sugarcane," Plant Soil, May 2012, 356:231-243.

Dandekar et al., "Conservation of gene order: a fingerprint of proteins that physically interact," Trends Biochem. Sci., 1998, 23:324-328.

Das et al., "Microbial assay of N2 fixation rate, a simple alternate for acetylene reduction assay," MethodsX, May 2018:909-914.

Datsenko et al., "One-step inactivation of chromosomal genes in *Escherichia coli* K-12 using PCR products," PNAS, Jun. 2000, 97(12):6640-6645.

Davin-Regli et al., "Enterobacter aerogenes and Enterobacter cloacae; versatile bacterial pathogens confronting antibiotic treatment," Front. Microbiol., Jun. 2015:392, 10 pages.

De Bruijn et al., "The Cloning and characterization of the glnF (ntrA) Gene of *Klebsiella pneumoniae*: Role of glnF (ntrA) in the Regulation of Nitrogen Fixation (nif) and other Nitrogen assimilation genes," Mol. Genet., Aug. 1983, 192:342-353.

De Freitas, "Yield and N assimilation of winter wheat (*Triticum aestivum* L., var. *Norstar*) inoculated with rhizobacteria," Pedobiologia, Jan. 2000, 44(2):97-104.

De Raad et al., "A solid-phase platform for combinatorial and scarless multipart gene assembly," ACS Synth. Biol., Feb. 2013:316-326.

Delaux et al., "Tracing the evolutionary path to nitrogen-fixing crops." Curr. Opin. Plant Biol., Jun. 26, 2015:95-99.

Dent et al., "Establishing symbiotic nitrogen fixation in cereals and other non-legume crops: The greener nitrogen revolution," Agric & Food Secur, Dec. 2017, 6(7):1-9.

Dersch et al., "Novel Approach for High-Throughput Metabolic Screening of Whole Plants for Stable Isotopes," Plant Physiology, Mar. 2016, 171(1):25-42.

Desnoues et al., "Nitrogen fixation genetics and regulation in a Pseudomonas stutzeri strain associated with rice," Microbiology, May 2003, 149:2251-2262.

Dixon et al., "Genetic regulation of biological nitrogen fixation," Nature Reviews, Aug. 2, 2004:621-631.

Dixon et al., "Genetic transfer of nitrogen fixation from Klebsiella pneumoniae to *Escherichia coli*," Nature, 1972, 237(5350):102-103.

Dong et al., "Kinetics and Strain Specificity of Rhizosphere and Endophytic Colonization by Enteric Bacteria on Seedlings of *Medicago sativa* and Medicago truncatula," Appl Environ Microbial., Mar. 2003, 69(3):1783-1790.

Dos Santos et al., "Distribution of nitrogen fixation and nitrogenase-like sequences amongst microbial genomes," BMC Genomics, Dec. 2012, 13(1):162, 12 pages.

Du et al., "Customized optimization of metabolic pathways by combinatorial transcriptional engineering," Nucleic Acids Res., Oct. 2012, 40(18):e142, 10 pages.

Dykxhoorn et al., "A set of compatible tac promoter expression vectors," Gene, 1996, 177(1-2):133-136.

Easter et al., "Role of the parCBA Operon of the Broad-Host-Range Plasmid RK2 in Stable Plasmid Maintenance," Journal Of Bacteriology, 1998, 180(22):6023-6030.

Egener et al., "Identification of NifL-like protein in a diazotroph of the b-subgroup of the proteobacteria, *azoarcus* sp. strain BH72," Microbiology, Oct. 2002, 148(10):3203-3212.

Emboss. Emboss Needle: Pairwise Sequence Alignment (Nucleotide). Available at URL<http://www.ebi.ac.uk/Tools/psa/emboss_needle/nucleotide.html>, Accessed on Oct. 10, 2016, 1 page.

Emboss. Emboss Water: Pairwise Sequence Alignment (Nucleotide). Available at URL<http://www.ebi.ac.uk/Tools/psa/emboss_water/nucleotide.html>, Accessed on Oct. 10, 2016, 1 page.

Endy et al., "Foundations for engineering biology," Nature, 2005, 438:449-453.

Engler et al., "A one pot, one step, precision cloning method with high throughput capability," PLoS One, 2008, 3(11):e3647, 7 pages.

Engler et al., "Golden gate shuffling: a one-pot DNA shuffling method based on type IIs restriction enzymes," PLoS One, 2009, 4(5):e5553, 9 pages.

Enkh-Amgalan et al., "Molecular evolution of the nif gene cluster carrying nifI1 and nifI2 genes in the Gram-positive phototrophic bacterium Heliobacterium chlorum," International Journal of Systematic and Evolutionary Microbiology, 2006, 56:65-74.

EP Extended European Search Report in European Appln. No. 12800054.4, mailed Dec. 19, 2014, 8 pages.

EP Extended European Search Report in European Appln. No. 16825147.8, dated Jun. 6, 2019, 19 pages.

EP Extended European Search Report in European Appln. No. 16854192.8, dated Feb. 20, 2019, 11 pages.

EP Extended European Search Report in European Appln. No. 18739050.5, dated Feb. 1, 2021, 22 pages.

EP Extended European Search Report in European Appln. No. 18843845.1, dated Jul. 22, 2021, 20 pages.

EP Extended European Search Report in European Appln. No. 18870346.6, dated Jul. 22, 2021, 5 pages.

EP Extended European Search Report in European Appln. No. 19186353.9, dated Nov. 13, 2019, 9 pages.

EP Partial Supplementary European Search Report Appln. No. 16825147.8 dated Mar. 4, 2019, 21 pages.

EP Partial Supplementary European Search Report Appln. No. 19826654.6 dated Mar. 17, 2022, 11 pages.

EP Partial Supplementary European Search Report in European Appln. No. 18843845.1, dated Apr. 12, 2021, 17 pages.

EP Partial Supplementary European Search Report in European Appln. No. 18870036.3, dated Aug. 19, 2021, 19 pages.

EP Supplementary Partial European Search Report in International Appln. No. 18739050.5, dated Oct. 27, 2020, 18 pages.

Estrem et al., "Identification of an UP element consensus sequence for bacterial promoters," PNAS, 1998, 95(11):9761-9766.

Extended European Search Report in European Application No. 20751885.3, mailed on Mar. 3, 2023, 4 pages.

Extended European Search Report in European Appln. No. 18870036.3, dated Dec. 14, 2021, 28 pages.

Extended European Search Report in European Appln. No. 19833252.0, dated Mar. 14, 2022, 24 pages.

Eyraud et al., "Expression and Biological Activity of the Cystine Knot Bioinsecticide PA1b (Pea Albumin 1 Subunit b)," PLOS One, Dec. 2013, 8(12):e81619, 9 pages.

Fani et al., "Molecular evolution of nitrogen fixation: the evolutionary history of the nifD, nifK, nifE, and nifN gene," J. Mol. Evol., 2000, 51(1):1-11.

Feher et al. "In the fast lane: large-scale bacterial genome engineering," J Biotechnol., Jul. 2012, 160(1-2):72-9.

(56) References Cited

OTHER PUBLICATIONS

Ferrières et al., "The yjbEFGH locus in *Escherichia coli* K-12 is an operon encoding proteins involved in exopolysaccharide production," Microbiology, Apr. 2007, 153(Pt 4):1070-80.

Fischbach et al., "Prokaryotic gene clusters: A rich toolbox for synthetic biology," Biotechnology Journal, 2010, 15(12):1277-1296.

Fischbach et al., "The evolution of gene collectives: how natural selection drives chemical innovation," Proc. Natl. Acad. Sci. USA, 2008, 105:4601-4608.

Fontana et al., "RNA folding and combinatory landscapes," Phys. Rev. E., 1993, 47:2083-2099.

Forner et al., "Treatment of hepatocellular carcinoma," Crit Rev Oncol Hematol., Nov. 2006, 60(2):89-98.

Fox et al., "Major cereal crops benefit from biological nitrogen fixation when inoculated with the nitrogen-fixing bacterium Pseudomonas protegens Pf-5 X940." Environmental Microbiology, 2016, 18(10):3522-3534.

Frasch et al., "Design-based re-engineering of biosynthetic gene clusters: plug-and-play in practice," Curr Opin Biotechnol., Dec. 2013, 24(6):1144-50.

Gaby et al., "A comprehensive aligned nifH gene database: a multipurpose tool for studies of nitrogen-fixing bacteria," Database, 2014, 2014:bau001, 8 pages.

Gamer et al., "A T7 RNA polymerase-dependent gene expression system for Bacillus megaterium," Appl Micro Biol Biotechnol., Apr. 2009, 82(6):1195-203.

Gebeyehu et al., "Novel biotinylated nucleotide-analogs for labeling and colorimetric detection of DNA," Nucl. Acids Res., 1987, 15:4513, 22 pages.

Geddes et al., "Use of plant colonizing bacteria as chassis for transfer of N2-fixation to cereals." Curr. Opin. Biotechnol. 2015, 32:216-222.

GenBank Accession No. CP007215.3, "Kosakonia sacchari SP1 chromosome, complete genome," Sep. 19, 2017, 729 pages.

GenBank Accession No. CP016337.1 "Kosakonia sacchari strain BO-1 chromosome, complete genome," Jul. 11, 2016, 1119 pages.

Georg et al., "cis-antisense RNA, another level of gene regulation in bacteria," Microbiol. Mol. Biol. Rev., 2011, 75(2):286-300.

Gibson et al., "Chemical synthesis of the mouse mitochondrial genome," Nat. Methods, Jul. 2010:901-903.

Gibson et al., "Enzymatic assembly of DNA molecules up to several hundred kilobases," Nat Methods, 2009, 6(5):343-345.

Gibson, "Physical Environment and Symbiotic Nitrogen Fixation," Australian Journal of Biological Sciences, 1963, 16(1):28-42.

Gosink et al., "The product of the Klebsiella pneumoniae nifX gene is a negative regulator of the nitrogen fixation (nif) regulon," J Bacteriology, 1990, 172(3):1441-1447.

Gossen et al., "Tight control of gene expression in mammalian cells by tetracycline-responsive promoters," PNAS USA, 1992, 89(12):5547-5551.

Gossen et al., "Transcriptional activation by tetracyclines in mammalian cells," Science, 1995, 268(5218):1766-1769.

Gottelt et al., "Deletion of a regulatory gene within the cpk gene cluster reveals novel antibacterial activity in Streptomyces coelicolor A3(2)," Microbiology, 2010, 156:2343-2353.

Govantes et al., "Mechanism of coordinated synthesis of the antagonistic regulatory proteins NifL and NifA of Klebsiella pneumoniae," J Bacteriol. Dec. 1996, 178(23):6817-6823.

Guell et al., "Bacterial transcriptomics: what is beyond the RNA horiz-ome?," Nature Reviews Microbiology, 2011, 9(9):658-669.

Guell et al., "Transcriptome complexity in a genome-reduced bacterium," Science, 2009, 326:1268-1271.

Guo et al., "Discovery of Reactive Microbiota-Derived Metabolites that Inhibit Host Proteases," Cell, Jan. 2017, 168(3):517-526, e18.

Haapalainen et al., "Soluble plant cell signals induce the expression of the type III secretion system of Pseudomonas syringae and upregulate the production of pilus protein HrpA," Mol. Plant Microbe Interact., 2009, 22:282-290.

Hale et al., "An efficient stress-free strategy to displace stable bacterial plasmids," BioTechniques, Mar. 2010, 48:223-228.

Hansal et al., "Cutting Edge: Induction of antigen-specific hyporesponsiveness by transplantation of hemopoietic cells containing an MHC class I transgene regulated by a lymphocyte-specific promoter," J Immunol., Aug. 1998, 161(3):1063-8.

Hara et al., "Identification of Nitrogden-Fixing Bradyrhizobium Assoicated with Roots of Field-Grown Sorghum by Metagenome and Proteome Analyses," Frontiers in Microbiology, Mar. 10, 2019.

Hardarson et al., "Use of 15N methodology to assess biological nitrogen fixation," Use of Nuclear Techniques in Studies of Soil-plant Relationships, May 1990, pp. 129-160.

Harvey et al., "Inducible control of gene expression: prospects for gene therapy," Curr Opin Chem Biol., Aug. 1998, 2(4):512-8.

Herlache et al., "Characterization of the Agrobacterium vitis pehA gene and comparison of the encoded polygalacturonase with the homologous enzymes from Erwinia carotovora and Ralstonia solanacearum," Appl Environ Microbial., Jan. 1997, 63(1):338-346.

Hernandez et al., "Biochemical analysis of the recombinant Fur (ferric uptake regulator) protein from Anabaena PCC 7119: factors affecting its oligomerization state," Biochem. J., 2002, 366:315-322.

Hidaka et al., "Promotion of the Growth of Rice by Inoculation of Nitrogen-Fixing-Activity—Enhanced Bacteria to the Rhizosphere," Nitrogen Fixation: From Molecules to Crop Productivity (Part of the Current Plant Science and Biotechnology in Agriculture book series (PSBA, vol. 38)), 2002, p. 445.

Hippler et al., "Mass and Isotope Selective Infrared Spectroscopy," Handbook of High-Resolution Spectroscopy, vol. 2, Chapter 28, pp. 1069-1118 (2011).

Hoeschle-Zeledon et al., "Regulatory challenges for biological control," The CGIAR Systemwide Program on Integrated Pest Management, Jan. 2013, SP-IPM Secretariat, International Institute of Tropical Agriculture (IITA), Ibadan, Nigeria, 53 pages.

Holden et al., "Colonization outwith the colon: plants as an alternative environmental reservoir for human pathogenic enterobacteria," FEMS Microbiol. Rev., 2009, 33:689-703.

Hu et al., "Assembly of nitrogenase MoFe protein," Biochemistry, 2008, 47(13):3973-3981.

Hunter, "'Genetically Modified Lite' placates public but not activists," EMBO Reports, Jan. 2014, 15(2):138-141.

Huynen et al., "Smoothness within ruggedness: the role of neutrality in adaptation," Proc. Natl. Acad. Sci. USA, 1996, 93:397-401.

Iber, "A quantitative study of the benefits of co-regulation using the spoIIA operon as an example," Mol. Sys. Biol., Feb. 2006:1-6.

Idalia et al., "*Escherichia coli* as a model organism and its application in biotechnology," Recent Advances on Physiology, Pathogenesis, and Biotechnological Applications, Chapter 13, 2017, pp. 253-274.

Iniguez et al., "Nitrogen Fixation in Wheat Provided by Klebsiella pneumoniae 342," MPMI, 2004, 17(10):1078-1085.

Intechopen.com, [online], "*Escherichia coli* as a Model Organism and Its Application in Biotechnology, IntechOpen," 2020, retrieved on Mar. 31, 2020, retrieved from URL<https://www.intechopen.com/books/-i-escherichia-coli-i-recent-advances-on-physiology-pathogenesis-and-biotechnological-applications/-i-escherichi%E2%80%A6>, 15 pages.

International Preliminary Report on Patentability in International Appln. No. PCT/US2019/039528, mailed Jan. 7, 2021, 15 pages.

International Preliminary Report on Patentability in International Appln. No. PCT/US2020/029831, mailed Nov. 4, 2021, 8 pages.

International Search Report and Written Opinion in International Appln. No. PCT/US2019/064782, mailed Apr. 16, 2020, 14 pages.

International Search Report and Written Opinion in International Appln. No. PCT/US2020/014083, mailed Jul. 20, 2020, 24 pages.

International Search Report and Written Opinion in International Appln. No. PCT/US2021/029993, mailed Sep. 15, 2021, 12 pages.

International Search Report and Written Opinion in International Appln. No. PCT/US2021/055858, dated Mar. 25, 2022, 12 pages.

Invitation to Pay Additional Fees in International Appln. No. PCT/US2020/014083, mailed May 28, 2020, 20 pages.

(56) References Cited

OTHER PUBLICATIONS

Ishihama, "Prokaryotic genome regulation: multifactor promoters, multitarget regulators and hierarchic networks," FEMS Microbial Rev., 2010, 34(5):628-645.
Ivanova et al., "Artificial Regulation of Genes, Of the coding proteins of the nitrogenase complex Rhizobial bacteria," Natural Sciences, 2014, 13(174):36-39 (Machine Translation).
Izquierdo et al., "Distribution of Extensive nifH Gene Diversity Across Physical Soil Microenvironments," Microbial Ecology, 2006, 51(4):441-452.
Jacob et al., "Solid-state NMR studies of Klebsiella pneumoniae grown under nitrogen-fixing conditions," J. Biol. Chem., 1987, 262(1):254-259.
Jacoby et al., "The Role of Soil Microorganisms in Plant Mineral Nutrition-Current Knowledge and Future Directions," Frontiers in Plant Science, 2017, 8(19):1-19.
Jahn et al., "Extraction of Extracellular Polymeric Substances (EPS) from Biofilms Using a Cation Exchange Resin," Wat. Sci. Tech., 1995, 32(8):157-164.
Janczarek et al., "Multiple copies of rosR and pssA genes enhance exopolysaccharide production, symbiotic competitiveness and clover nodulation in *Rhizobium leguminosarum* bv. *trifolii*," Antonie Van Leeuwenhoek, Nov. 2009, 96(4):471-86.
Jashke et al., "A fully decompressed synthetic bacteriophage 0X174 genome assembled and archived in yeast," Virology, 2012, 434:278-284.
Jensen, "The *Escherichia coli* K-12 "wild types" W3110 and MG1655 have an rph frameshift mutation that leads to pyrimidine starvation due to low pyre expression levels," J. Bacteriol., 1993, 175:3401-3407.
Johnson et al., "Properties of overlapping genes are conserved across microbial genomes," Genome Res., 2004, 14(11):2268-2272.
Joseph et al., "Recent developments of the synthetic biology toolkit for Clostridum," Frontiers in Microbiology, 2018, 9(154):1-13.
Kabaluk et al., "The use and regulation of microbial pesticides in representative jurisdictions worldwide," IOBC Global, 2010, 99 pages.
Kalir et al., "Ordering genes in a flagella pathway by analysis of expression kinetics from living bacteria," Science, 2001, 292(5524):2080-2083.
Kaneko et al., "Complete genomic structure of the cultivated rice endophyte *Azospirillum* sp. B510," DNA Res., 2010, 17:37-50.
Kant et al., "Understanding plant response to nitrogen limitation for the improvement of crop nitrogen use efficiency," Journal of Experimental Botany, 2011, 62(4):1499-1509.
Karlin et al., "Applications and statistics for multiple high-scoring segments in molecular sequences," Proc Natl Acad Sci USA, Jun. 1993, 90(12):5873-7.
Karlin et al., "Methods for assessing the statistical significance of molecular sequence features by using general scoring schemes," Proc Natl Acad Sci USA, Mar. 1990, 87(6):2264-8.
Katsnelson, "Engineered bacteria could boost corn yields: Gene-edited microbe offer continuous nitrogen fixation," Chemical & Engineering News, Dec. 28, 2021, retrieved from URL <https://cen.acs.org/food/agriculture/Engineered-bacteria-boost-corn-yields/99/web/2021/12>, 3 pages.
Kececioglu et al., "Of mice and men: Algorithms for evolutionary distances between genomes with translocation," SODA: Proceedings of the sixth annual ACM-SIAM symposium on Discrete algorithms, 1995, 10 pages.
Kelly et al., "Measuring the activity of BioBrick promoters using an in vivo reference standard," J. Biol. Eng., Mar. 2009:4, 13 pages.
Kent et al., "A Transposable Partitioning Locus Used To Stabilize Plasmid-Borne Hydrogen Oxidation and Trifolitoxin Production Genes in a Sinorhizobium Strain," Appl. Environ. Microbiol., 1998, 64(5):1657-1662.
Kerby et al., "Photoproduction of ammonium by immobilized mutant strains of Anabaena variabilis," Applied Microbiology and Biotechnology, Apr. 1986, 24(1):42-46.
Kim et al., "A 20 nucleotide upstream element is essential for the nopaline synthase (nos) promoter activity," Plant Mol Biol., Jan. 1994, 24(1):105-17.
Kim et al., "Constitutive expression of nitrogenase system in Klebsiella oxytoca by gene targeting mutation to the chromosomal nifLA operon," Journal of Biotechnology, Jun. 1989, 10(3-4):293-301.
King et al., "Spider-Venom Peptides: Structure, Pharmacology, and Potential for Control of Insect Pests," Annu. Rev. Entomol., 2013, 58:475-96.
Kingsford et al., "Rapid, accurate, computational discovery of Rho-independent transcription terminators illuminates their relationship to DNA uptake," Genome Bio. 2007, 8(2):R22, 12 pages.
Kitano, "Systems biology: a brief overview," Science, 2002, 295(5560): 1662-1664.
Klose et al., "Glutamate at the site of phosphorylation of nitrogen-regulatory protein NTRC mimics aspartyl-phosphate and activates the protein," J Mol Biol., Jul. 1993, 232(1):67-78.
Knight, "Idempotent Vector Design for Standard Assembly of Biobricks," MIT Artificial Intelligence Laboratory, The TTL Data Book for Design Engineers, 2003, 11 pages.
Kovacs et al., "Stochasticity in protein levels drives colinearity of gene order in metabolic operons of *Escherichia coli*," PLoS Biol., 2009, 7(5):e1000115, 9 pages.
Kranz et al., "Ammonia-constitutive nitrogen fixation mutants of Rhodobacter capsulatus," Gene, Nov. 1988, 71(1):65-74.
Kumar et al., "Metabolic regulation of *Escherichia coli* and its gdhA, glnL, gltB, D mutants under different carbon and nitrogen limitations in the continuous culture," Microbial Cell Factories, Jan. 2010, 9(8):1-17.
Kurzweil, "Plant Bacteria breakthrough enables crops worldwide to take nitrogen from the air," Plant Bacteria Breakthrough Enables Crops Worldwide Take Nitrogen From Air. Aug. 1, 2013. http://www.kurzweilai.neUplant-bacteria-breakthrough-enables-cropsworldwide-to-take-nitrogen-from- the-air, 4 pages.
Kutter et al., "Colonization of barley (*Hordeum vulgare*) with *Salmonella enterica* and *Listeria* spp," FEMS Microbial. Ecol., 2006, 56, 262-271.
Lauritsen et al., "A versatile one-step CRISPR-Cas9 based approach to plasmid-curing." Microb Cell Fact, 2017, 16(135):1-10.
Leang et al, "Genome-wide analysis of the RpoN regulon in Geobacter sulfurreducens," BMC Genomics, Jul. 10, 2009:331, 19 pages.
Lee et al., "The class IId bacteriocin thuricin-17 increases plant growth," Planta, 2009, 229:747-755.
Lenski et al., "Effects of Segregation and Selection on Instability of Plasmid pACYC184 in *Escherichia coli* B," Journal of Bacteriology, Nov. 1987, 169(11):5314-5316.
Levican et al., "Comparative genomic analysis of carbon and nitrogen assimilation mechanisms in three indigenous bioleaching bacteria: predictions and validations," BMC Genomics, Sep. 2008:581, 19 pages.
Levin-Karp et al., "Quantifying translational coupling in *E. coli* synthetic operons using RBS modulation and fluorescent reporters," ACS Synth. Biol., Feb. 2013:327-336.
Li et al., "Human Enhancers Are Fragile and Prone to Deactivating Mutations," Mol Biol Evol., Aug. 2015, 32(8):2161-80.
Liang et al., "Minimal effect of gene clustering on expression in *Escherichia coli*," Genetics, Feb. 2013, 193(2):453-65.
Lifesci.sussex.ac.uk, [online], "Bacillus thuringiensis Toxin Nomenclature," 2016, retrieved on Mar. 25, 2021, retrieved from URL<www.lifesci.sussex.ac.uk/home/Neil_Crickmore/Bt/> 1 page.
Lim et al., "Fundamental relationship between operon organization and gene expression," Proc Natl Acad Sci USA, Jun. 2011, 108(26):10626-31.
Lin et al., "PC, a Novel Oral Insecticidal Toxin from Bacillus bombysepticus Involved in Host Lethality via APN and BtR-175," Scientific Reports, Jun. 2015, 5:11101, 14 pages.
Liu et al., "Phenazine-1-carboxylic acid biosynthesis in Pseudomonas Chlororaphis GP72 is positively regulated by the sigma factor RpoN," World Journal of Microbiology and Biotechnology, Jan. 2008, 24(9):1961-1966.

(56) References Cited

OTHER PUBLICATIONS

Liu et al., "Whole genome analysis of halotolerant and alkalotolerant plant growth-promoting rhizobacterium *Klebsiella* sp. D5A," Sci Rep., May 6, 2016:1-10.
Lombo et al., "The mithramycin gene cluster of Streptomyces argillaceus contains a positive regulatory gene and two repeated DNA sequences that are located at both ends of the cluster," J. Bacterial., 1999, 181:642-647.
Lowman et al., "Strategies for enhancement of switchgrass (*Panicum virgatum* L.) performance under limited nitrogen supply based on utilization of N-fixing bacterial endophytes," Plant and Soil, Aug. 2016, 405(1):47-63, 17 pages.
Lucks et al., "Toward scalable parts families for predictable design of biological circuits," Curr. Opin. Microbiol., Nov. 2008:567-573.
Ma et al., "Effect of nicotine from tobacco root exudates on chemotaxis, growth, biocontrol efficiency, and colonization by *Pseudomonas aeruginosa* NXHG29," Antonie van Leeuwenhoek, 2018, 111(7):1237-1257.
Mabrouk et al., "Chapter 6: Potential of Rhizobia in Improving Nitrogen Fixation and Yields of Legumes," Symbiosis, May 30, 2018, IntechOpen, pp. 1-16, retrieved on Jan. 12, 2021, retrieved from URL<https://www.intechopen.com/books/symbiosis/potential-of-rhizobia-in-improving- B351nitrogen-fixation-and-yields-of-legumes> 2 pages, Abstract.
MacNeil et al., "Fine-structure mapping and complementation analysis of nif (nitrogen fixation) genes in *Klebsiella pneumoniae*," J Bacterial. Oct. 1978, 136(1):253-266.
MacNeil et al., "Mutations in nif genes that cause *Klebsiella pneumoniae* to be derepressed for nitrogenase synthesis in the presence of ammonium," J Bacterial, Nov. 1980, 144(2):744-751.
Maduro, "Random DNA Generator," retrieved from URL <http://www.faculty.ucr.edu/~mmaduro/random.htm>, 2011, 1 page.
Magari et al., "Pharmacologic control of a humanized gene therapy system implanted into nude mice," J Clin Invest., Dec. 1997, 100(11):2865-2872.
Magasanik, "Genetic control of nitrogen assimilation in bacteria," Ann. Rev. Genet, 1982, 16:135-68.
Mandal et al., "Gene regulation by riboswitches," Nat. Rev. Mol. Cell Biol., 2004, 5(6):451-463.
Mao et al., "Silencing a cotton bollworm P450 monooxygenase gene by plant-mediated RNAi impairs larval tolerance of gossypol," Nature Biotechnology, Nov. 2007, 25(11): 1307-1313.
Marroqui et al., "Enhanced Symbiotic Performance by Rhizobium tropici Glycogen Synthase 17, 18 Mutants," Journal of Bacteriology, Feb. 2001, 183(3):854-864.
Martiez-Noel et al., "NifB and NifEN protein levels are regulated by ClpX2 under nitrogen fixation conditions in Azotobacter vinelandii," Mol Microbiol., Mar. 2011, 79(5):1182-93.
Martinelli et al., "Structure-function studies on jaburetox, a recombinant insecticidal peptide derived from jack bean (*Canavalia ensiformis*) urease," Biochimica et Biophysica Acta, Mar. 2014, 1840(3):935-44.
Marx et al., "Broad-host-range ere-lox system for antibiotic marker recycling in gram-negative bacteria," Biotechniques, Nov. 2002, 33(5):1062-7.
Masepohl et al., "Organization and regulation of genes encoding the molybdenum nitrogenase and the alternative nitrogenase in Rhodobacter capsulatus," Arch. Microbial., Sep. 1996, 165:80-90.
Mason et al., "Cryptic Growth in Klebsiella-Pneumoniae," Appl. Microbiol. Biot., 1987, 25(6):577-584.
Matsubayashi et al., "Peptide hormones in plants," Annu Rev Plant Biol., 2006, 57:649-74.
Medema et al., "Computational tools for the synthetic design of biochemical pathways," Nat Rev Microbiol., Jan. 2012, 10(3):191-202.
Medema et al., "Exploiting plug-and-play synthetic biology for drug discovery and production in microorganisms," Nat. Rev. Microbiol., Sep. 2011:131-137.
Medema et al., "Synthetic biology in Streptomyces bacteria," Methods Enzymol., 2011, 497:485-502.
Mengel, "Roots, growth and nutrient uptake." Dept. of Agronomy publication #AGRY-95-08 (Rev. May 1995), 8 pages.
Merriam-webster.com, [online], "Merriam-Webster Originate," 2020, Retrieved on Jun. 7, 2020, retrieved from URL<https://www.merriam-webster.com/dictionary/originate?utm_campaign=sd&utm_medium=serp&utm_source=jsonld>, 13 pages.
Mills, "Optical Sensors for Carbon Dioxide and Their Applications," *Sensors for Environment, Health and Security*, 2009, 347-370 (Abstract Only).
Mirsky, "Refactoring the Salmonella Type III Secretion System," Doctoral Dissertation, Apr. 12, 2012, 60 pages.
Mirzahoseini et al., "Heterologous Proteins Production in *Escherichia coli*: An Investigation on the Effect of Codon Usage and Expression Host Optimization," Cell Journal (Yakhteh), Dec. 2011, 12(4):453, 7 pages.
Mitra, "Regulation of nifLA operon in Azotobacter vinelandii," Thesis submitted to the Jawaharlal Nehru University, New Delhi, for the degree of doctor of philosophy, 2000, 153 pages.
Miyazaki, "Creating random mutagenesis libraries by megaprimer PCR of whole plasmid (MEGA WHOP)," Methods Mol. Biol., 2003, 231:23-28.
Montoya et al., "A Simple, High-Precision, High-Sensitivity Tracer Assay for N(inf2) Fixation," Applied and Enviornmetnal Microbiology, Jan. 1996, 62(3):986-993.
Moon et al., "Genetic programs constructedfrom layered logic gates in single cells," Nature, Nov. 2012, 491(7423):249-53.
Mueller et al., "Closing yield gaps through nutrient and water management," Nature, 2012, 490:254-257.
Mus et al., "Diazotrophic Growth Allows Azotobacter vinelandii To Overcome the Deleterious Effects of a glnE Deletion," Appl Environ Microbiol., Jun. 2017, 83(13):e00808-17.
Mus et al., "Symbiotic Nitrogen Fixation and the Challenges to Its Extension to Nonlegumes," Appl Environ Microbial., Jul. 2016, 82(13):3698-3710.
Muse et al., "The nac (Nitrogen Assimilation Control) Gene from *Escherichia coli*," Journal of Bacteriology, Mar. 1998, 180(5):1166-1173.
Mutalik et al., "Quantitative estimation of activity and quality for collections of functional genetic elements," Nat. Methods, Oct. 2013:347-353.
Nagy et al., "Nanofibrous solid dosage form of living bacteria prepared by electrospinning," eXPRESS Polymer Letters, 2014, 8(5):352-361.
Naimov et al., "Solubilization, Activation, and Insecticidal Activity of Bacillus thuringiensis Serovar thompsoni HD542 Crystal Proteins," Applied and Environmental Microbiology, Dec. 2008, 74(23):7145-7151.
Nassar et al., "Promotion of plant growth by an auxin-producing isolate of the yeast Williopsis saturnus endophytic in maize (*Zea mays* L.) roots," Biology and Fertility of Soils, 2005, 42:97-108.
Nature.com, [online], "Transcription Unit," 2005, retrieved on Apr. 15, 2021, retrieved from URL<https://www.nature.com/scitable/definition/transcription-unit-260>, 2 pages.
Nelissen et al., "Translational research:from pot to plot," Plant Biotechnology Journal, Jan. 12, 2014:277-285.
Nestmann, "Mutagenesis by nitrosoguanidine, ethyl methanesulfonate, and mutator gene mutH in continuous cultures of *Escherichia coli*," Science Direct, Jun. 1975, 28(3):323-330.
Nichkawade, "Studies on upstream regulatory sequence of the nifLA promoter of Klebsiella pnuemoniae," Thesis submitted to the Jawaharlal Nehru University, New Delhi, for the degree of doctor of philosophy, 1996, 166 pages.
Nielsen et al., "Conceptual model for production and composition of exopolymers in biofilms," Wat. Sci. Tech., 1997, 36(1): 11-19.
Nielsen et al., "Extraction of EPS," Wingender et al. (eds.), Microbial Extracellular Polymeric Substances, 1999, 24 pages.
Nielsen, "Transgenic organisms—time for conceptual diversification?," Nature Biotechnology, 2003, 21:227-228.
No et al., "Ecdysone-inducible gene expression in mammalian cells and transgenic mice," Proc. Natl. Acad. Sci. USA, Apr. 1996, 93(8):3346-3351.
Noskov et al., "Assembly of large, high G+C bacterial DNA fragments in yeast," ACS Synth. Biol., Jan. 2012:267-273.

(56) References Cited

OTHER PUBLICATIONS

Oh et al., "Organization of nif gene cluster in *Frankia* sp. EuIK1 strain, a symbiont of Elaeagnus umbellata," Arch. Microbiol., 2012, 194:29-34.
Ohta et al., "Associative N2-fixation of Rice with Soil and Microorganisms," 1985, 27:17-27 (Abstract Only).
Ohtsuka et al., "An alternative approach to deoxyoligonucleotides as hybridization probes by insertion of deoxyinosine at ambiguous codon positions," J. Biol. Chem., 1985, 260:2605-2608.
Okubo et al., "Effects of Elevated Carbon Dioxide, Elevated Temperature, and Rice Growth Stage on the Community Structure of Rice Root-Associated Bacteria," Microbes Environ., Jun. 2014, 29(2):184-190.
Orme-Johnson, "Molecular basis of biological nitrogen fixation," Annu. Rev. Biophys. Biophys. Chem., 1985, 14:419-459.
Ortiz-Marquez et al., "Association with an Ammonium-excreting bacterium allows diazotrophic culture of oil-rich Eukaryotic microalagae," Appl. Microbial., 2012, 78(7):2345-2352.
Pakula et al., "Genetic analysis of protein stability and function," Annu Rev Genet, 1989, 23:289-310.
Parker et al., "Pore-forming protein toxins: from structure to function," Progress in Biophysics & Molecular Biology, 2005, 88:91-142.
Patil et al., "Liquid formulations of Acetobacter diazotrophicus L 1 and Herbaspirillum seropedicae J24 and their field trials on wheat," International Journal of Environmental Science, 2012, 3(3):1116-1129, 4 pages (Abstract Only).
PCT International Preliminary Report on Patentability in International Application No. PCT/US2020/031199, mailed on Nov. 10, 2022, 15 pages.
PCT International Preliminary Report on Patentability in International Appln. No. PCT/US2012/042502, dated Dec. 17, 2013, 8 pages.
PCT International Preliminary Report on Patentability in International Appln. No. PCT/US2013/068055, dated May 14, 2015, 10 pages.
PCT International Preliminary Report on Patentability in International Appln. No. PCT/US2016/042170, dated Jan. 16, 2018, 19 pages.
PCT International Preliminary Report on Patentability in International Appln. No. PCT/US2016/055429, dated Apr. 10, 2018, 12 pages.
PCT International Preliminary Report on Patentability in International Appln. No. PCT/US2018/013671, dated Jul. 16, 2019, 6 pages.
PCT International Preliminary Report on Patentability in International Appln. No. PCT/US2018/046148, dated Feb. 11, 2020, 10 pages.
PCT International Preliminary Report on Patentability in International Appln. No. PCT/US2018/057174, dated Apr. 28, 2020, 4 pages.
PCT International Preliminary Report on Patentability in International Appln. No. PCT/US2018/057613, dated Apr. 28, 2020, 7 pages.
PCT International Preliminary Report on Patentability in International Appln. No. PCT/US2019/041429, dated Jan. 12, 2021, 11 pages.
PCT International Preliminary Report on Patentability in International Appln. No. PCT/US2019/068152, mailed Jul. 1, 2021, 12 pages.
PCT International Preliminary Report on Patentability in International Appln. No. PCT/US2020/029894, dated Nov. 4, 2021, 13 pages.
PCT International Search Report and Written Opinion in International Application No. PCT/US2020/031199, mailed on Apr. 22, 2021, 28 pages.
PCT International Search Report and Written Opinion in International Appln. No. PCT/2020/29831, dated Nov. 3, 2020, 19 pages.
PCT International Search Report and Written Opinion in International Appln. No. PCT/US2012/042502, dated Jan. 31, 2013, 11 pages.
PCT International Search Report and Written Opinion in International Appln. No. PCT/US2013/068055, dated Feb. 18, 2014, 15 pages.
PCT International Search Report and Written Opinion in International Appln. No. PCT/US2016/042170, dated Dec. 2, 2016, 22 pages.
PCT International Search Report and Written Opinion in International Appln. No. PCT/US2016/055429, dated Dec. 30, 2016, 16 pages.
PCT International Search Report and Written Opinion in International Appln. No. PCT/US2018/0013671, dated Mar. 22, 2018, 8 pages.
PCT International Search Report and Written Opinion in International Appln. No. PCT/US2018/046148, dated Dec. 3, 2018, 6 pages.
PCT International Search Report and Written Opinion in International Appln. No. PCT/US2018/057613, dated Mar. 5, 2019, 11 pages.
PCT International Search Report and Written Opinion in International Appln. No. PCT/US2019/039528, dated Nov. 6, 2019, 19 pages.
PCT International Search Report and Written Opinion in International Appln. No. PCT/US2019/041429, dated Dec. 3, 2019, 18 pages.
PCT International Search Report and Written Opinion in International Appln. No. PCT/US2019/059450, dated Mar. 10, 2020, 20 pages.
PCT International Search Report and Written Opinion in International Appln. No. PCT/US2019/068152, dated Jun. 25, 2020, 21 pages.
PCT International Search Report and Written Opinion in International Appln. No. PCT/US2019/39217, dated Nov. 19, 2019, 13 pages.
PCT International Search Report and Written Opinion in International Appln. No. PCT/US2020/029894, mailed Aug. 31, 2020, 19 pages.
PCT International Search Report and Written Opinion in International Appln. No. PCT/US2020/031201, dated Mar. 9, 2021, 28 pages.
PCT Written Opinion in International Appln. No. PCT/US2018/057174, dated Jan. 4, 2019, 3 pages.
Pfleger et al., "Combinatorial engineering of intergenic regions in operons tunes expression of multiple genes," Nature Biotechnology, 2006, 24(8):1027-1031.
Philippe et al., "Improvement of pCVD442, a suicide plasmid for gene allele exchange in bacteria," Plasmid, 2004, 51(3):246-255.
Piccioli et al. "Neuroantibodies: ectopic expression of a recombinant anti-substance P antibody in the central nervous system of transgenic mice," Neuron., Aug. 1995, 15(2):373-84.
Piccioli et al., "Neuroantibodies: molecular cloning of a monoclonal antibody against substance P for expression in the central nervous system," Proc Natl Acad Sci USA, Jul. 1991, 88(13):5611-5615.
Pickens et al., "Metabolic engineering for the production of natural products," Annu. Rev. Chem. Biomol. Eng., Feb. 2011:211-236.
Plotnikova et al., "Pathogenesis of the human opportunistic pathogen Pseudomonas aeruginosa PA14 in *Arabidopsis*," Plant Physiol., 2000, 124:1766-1774.
Poliner et al., "Nontransgenic Marker-Free Gene Disruption by an Episomal CRISPR System in the Oleaginous Microalga, Nannochloropsis oceanica CCMP1779," ACS Synth. Biol., 2018, 7(4):962-968.
Price et al., "Operon formation is driven by coregulation and not by horizontal gene transfer," Genome Res., 2005, 15:809-819.
Price et al., "The life-cycle of operons," PLoS Genet., Feb. 2006:e96, 15 pages.
Purcell et al., "Cholesterol oxidase: a potent insecticidal protein active against boll weevil larvae," Biochem Biophys Res Commun, Nov. 1993, 196(3):1406-13.

(56) References Cited

OTHER PUBLICATIONS

Purnick et al., "The second wave of synthetic biology: from modules to systems," Nat. Rev. Mol. Cell Biol., 2009, 10(6):410-422.
Pyne et al., "Coupling the CRISPR/Cas9 System with Lambda Red Recombineering Enables Simplified Chromosomal Gene Replacement in Escherichia coli," Applied and Environmental Microbioloy, Aug. 2015, 81(15):5103-5144.
Qaim et al., "Yield Effects of Genetically Modified Crops in Developing Countries," Science, Feb. 2003, 299(5608):900-2.
Qiu et al., "Construction of genetically engineered strains of Enterobacter cloacae (nifl~(-)A~(c))," Acta Phytophysiologica Sinica, Jan. 1999, 25(3):269-273.
Rakhee et al., "Extracellular polymeric substances of the marine fouling diatom amphora rostrata Wm.Sm," Biofouling, 2001, 17(2):117-127, 12 pages.
Ramirez et al., "Burkholderia and Paraburkholderia are Predominant Soybean Rhizobial Genera in Venezuelan Soils in Different Climatic and Topographical Regions," Microbes and Environments, Mar. 2019, 34(1):43-58.
Ramon et al., "Single-step linker-based combinatorial assembly of promoter and gene cassettes for pathway engineering," Biotechnol. Lett., 2011, 33:549-555.
Ran et al., "Genome erosion in a nitrogen-fixing vertically transmitted endosymbiotic multicellular cyanobacterium," PLoS One, Jul. 2010, 5(7):e11486, 11 pages.
Resendis-Antonio et al., "Systems biology of bacterial nitrogen fixation: High-throughput technology and its integrative description with constraint-based modeling," BMC Syst Biol., May 2011:120, 15 pages.
Riedel et al., "Nitrogen fixation by Klebsiella pneumoniae is inhibited by certain multicopy hybrid nif plasmids," J. Bacterial., 1983, 153(1):45-56.
Roberts et al., "Regulation and characterization of protein products coded by the nif (nitrogen fixation) genes of *Klebsiella pneumoniae*," J Bacterial., Oct. 1978, 136(1): 267-279.
Robledo et al., "Rhizobium cellulase CelC2 is essential for primary symbiotic infection of legume host roots," Proc Natl Acad Sci USA, May 2008, 105(19):7064-9.
Robledo et al., "Role of Rhizobium endoglucanase CelC2 in cellulose biosynthesis and biofilm formation on plant roots and abiotic surfaces," Microb Cell Fact., Sep. 11, 2012:125, 12 pages.
Robson et al., "Azotobacter Genomes: The Genome of Azotobacter chroococcum NCIMB 8003 (ATCC 4412)," PLOS One, Jun. 2015, 35 pages.
Rodrigues et al., "Chapter 3—Stable Isotope Analysis," *Comprehensive Analytical Chemistr*, 2013, 60: 77-99 (Abstract Only).
Rogers et al., "Synthetic biology approaches to engineering the nitrogen symbiosis in cereals," Journal of Experimental Botany, 2014, 65(8):1939-1946.
Rojas-Tapias et al., "Preservation of Azotobacter chroococcum vegetative cells in dry polymers," Univ. Sci., 2015, 20(2):201-207.
Rommens et al., "Intergeneric transfer and functional expression of the tomato disease resistance gene Pto," Plant Cell, Oct. 1995, 7(10):1537-1544.
Roncato-Maccari et al., "Endophytic Herbaspirillum seropedicae expresses nif genes in gramineous plants," FEMS Microbiology Ecology, 2003, 45:39-47.
Rong et al., "Promoter specificity determinants of T7 RNA polymerase," Proc. Natl. Acad. Sci. USA, 1998, 95(2):515-519.
Rosenblueth et al., "Bacterial endophytes and their interactions with hosts," Mol Plant Microbe Interact., Aug. 2006, 19(8):827-37.
Rosenblueth et al., "Nitrogen Fixation in Cereals," Frontiers in Microbiology, Aug. 2018, 9(1794):13 pages.
Rossolini et al., "Use of Deoxyinosine-Containing Primers vs Degenerate Primers for Polymerase Chain Reaction Based on Ambiguous Sequence Information," Mol. Cell. Probes, Aug. 1994:91-98.
Rubio et al., "Maturation of Nitrogenase: a Biochemical Puzzle," J. Bacteriology, 2005, 187(2):405-414.

Ryu et al., "Control of nitrogen fixation in bacteria that associate with cereals," Nat. Microbiol., Feb. 2020, 5(2):314-330, 31 pages.
Saikia et al., "Biological nitrogen fixation with non-legumes: An achievable target or a dogma?," Curr. Sci., Feb. 2007, 92(3): 317-322.
Saleh et al., "Involvement of gacS and rpoS in enhancement of the plant growth-promoting capabilities of Enterobacter cloacae CAL2 and UW4," Canadian Journal of Microbiology, Aug. 2001, 47(8):698-705.
Salis et al., "Automated design of synthetic ribosome binding sites to control protein expression," Nat. Biotechnol., 2009, 27(10):946-950.
Sanahuja et al., "Bacillus thuringiensis: a century of research, development and commercial applications," Plant Biotechnology Journal, Apr. 2011, 9(3):283-300.
Sandoval et al., "Strategy for directing combinatorial genome engineering in *Escherichia coli*," Proc Natl Acad Sci USA, Jun. 2012, 109(26):10540-5.
Sanjuan et al., "Multicopy plasmids carrying the Klebsiella pneumoniae nifA gene enhance Rhizobium meliloti nodulation competitiveness on alfalfa," Molecular Plant—Microbe Interactions, 1991, 4(4):365-369.
Santi et al., "Biological nitrogen fixation in non-legume plants," Annals of Botany, Jan. 2013, 111:743-767.
Sanyal et al., "The etiology of hepatocellular carcinoma and consequences for treatment," Oncologist, 2010, 15(Suppl 4):14-22.
Schmidt et al., "A Simple Urea Leaf-Feeding Method for the Production of 13C and 15N Labelled Plant Material," Plant and Soil, Feb. 2001, 229(2):197-202.
Schmidt-Dannert et al., "Molecular breeding of carotenoid biosynthetic pathways," Nat. Biotechnol., 2000, 18:750-753.
Schmitz et al., "Iron is required to relieve inhibitory effects on NifI on transcriptional activation by NifA in Klebsiella pneumoniae," J Bacterial, Aug. 1996, 178(15):4679-4687.
Schouten et al., "Do cisgenic plants warrant less stringent oversight?," Nature Biotechnology, Jul. 2006, 24(7):753.
Schuler et al., "Insect-resistant transgenic plants," Trends in Biotechnology, Apr. 1998, 16(4):168-175.
Schuler et al., "Potential side effects of insect-resistant transgenic plants on arthropod natural enemies," Trends Biotechnol., May 1999, 17(5):210-216.
Search Report in AP Appln. No. AP/P/2020/012401, dated Feb. 8, 2022, 4 pages.
Search Report in AP Appln. No. AP/P/2020/012402, dated Feb. 15, 2022, 5 pages.
Search Report in Russian Appln. No. 2020116764, dated Apr. 28, 2022, 15 pages (with English translation).
Service, "Genetically engineered microbes make their own fertilizer, could feed the world's poorest," Science, Apr. 2017, 2 pages.
Setten et al., "Engineering Pseudomonas protegens Pf-5 for Nitrogen Fixation and its application to improve plant growth under nitrogen-deficient conditions," PLOS One, 2013, 8(5):1-14.
Shamseldin, "The role of different genes involoved in symbiotic nitrogen fixation—review," Global Journal of Biotechnology & Biochemistry, 2013, 8(4):84-94.
Shetty et al., "Engineering BioBrick vectors from BioBrick parts," J. Biol. Eng., Feb. 2008:5, 12 pages.
Shuk, "Oxygen Gas Sensising Technologies Application: A Comprehensive Review," *Sensors for Everyday Life*, Nov. 2016, 81-107 (Abstract Only).
Sibold et al., "A nif mutant of Klebsiella pneumoniae fixing nitrogen in the presence of ammonia," FEMS Microbiology Letters, Jan. 1981, 10(1):37-41.
Sibold et al., "Constitutive expression of nitrogen fixation (nif) genes of *Klebsiella pneumoniae* due to a DNA duplication," EMBO J., 1982, 1(12):1551-8.
Siddavattam et al., "Regulation of nif Gene expression in Enterobacter agglomerans: Nucleotide sequence of the nifLA operon and influence of temperature and ammonium on its transcription," Molecular and general genetics, Dec. 1995, 249(6):629-636.
Simon et al., "Perturbation of niff expression in Klebsiella pneumoniae has limited effect on nitrogen fixation," J. Bacterial., 1996, 178(10):2975-2977.

(56) References Cited

OTHER PUBLICATIONS

Singer et al., "Genes and Genomes," Moscow: Mir, Jan. 1998:33, 4 pages (with machine translation).
Singh et al., "An L-methionine-D,L-sulfoximine-resistant mutant of the cyanobacterium Nostoc muscorum showing inhibitor-resistant y-glutamyl-transferase, defective glutamine synthetase and producing extracellular ammonia during N2 fixation," FESS Letters, Apr. 1983, 154(1):10-14.
Sivaraman et al., "Codon choice in genes depends on flanking sequence information—implications for theoretical reverse translation," Nucleic Acids Res., 2008, 36(3):e16, 8 pages.
Sleight et al., "Designing and engineering evolutionary robust genetic circuits," J Biol Engin., 2010, 4(12):1-20.
Sleight et al., "Randomized BioBrick assembly: a novel DNA assembly method for randomizing and optimizing genetic circuits and metabolic pathways," ACS Synth. Biol., 2013, 2(9):506-518.
Smanski et al., "Engineered Streptomyces platensis strains that overproduce antibiotics platensimycin and platencin," Antimicrob. Agents Chemother., 2009, 53:1299-12304.
Smanski et al., "Functional optimization of gene clusters by combinatorial design and assembly," Nat Biotechnol., 2014, 32(12):1241-1249.
Smanski et al., "Synthetic biology to access and expand nature's chemical diversity," Nat Rev Microbiol., Mar. 2016, 14(3):135-49.
Soong et al., "Design and Operation of a Continuous $^{13}$C and $^{15}$N Labeling Chamber for Uniform or Differential, Metabolic and Structural, Plant Isotope Labeling," Journal of Visualized Experiments, Jan. 2014, 83(16):1-8.
Sorek et al., "Prokaryotic transcriptomics: a new view on regulation, physiology, and pathogenicity," Nat. Rev. Genet., Nov. 2010:9-16.
Souza et al., "The N-Terminus of the NIFA protein of herbaspirillum seropedicae is probably involved in sensing of ammonia," In Tikhonovich et al. (Eds.) Proceedings of the 10th International Congress on Nitrogen Fixation, St. Petersburg, Russia, May 28-Jun. 3, 1995 (p. 260) Dordrecht: Kluwer.
Spiller et al., "Isolation and characterization of nitrogenase-derepressed mutant strains of cyanobacterium Anabaena variabilis," J Bacteriol. Feb. 1986, 165(2):412-419.
Staron et al., "The Third Pillar of Bacterial Signal Transduction: Classification of the Extracytoplasmic Function (ECF) Sigma Factor Protein Family," Mol. Microbiol., 2009, 14(3): 557-81.
Steenhoudt et al., "Azospirillum, a free-living nitrogen-fixing bacterium closely associated with grasses: genetic, biochemical and ecological aspects," FEMS Microbial. Rev., 2000, 24:487-506.
Stein et al., "The osteocalcin gene: a model for multiple parameters of skeletal-specific transcriptional control," Mol Biol Rep., Aug. 1997, 24(3):185-96.
Stemmer, "DNA shuffling by random fragmentation and reassembly: In vitro recombination for molecular evolution," Proc. Natl. Acad. Sci. USA, Oct. 1994, 91:10747-10751.
Stemple, "TILLING—a high-throughput harvest for functional genomics," Nature Reviews Genetics, Feb. 5, 2004:1-7.
Stephanopoulos, "Challenges in engineering microbes for biofuels production," Science, Feb. 2007, 315(5813):801-4.
Stewart et al., "In situ studies on nitrogen fixation with the acetylene reduction technique," Science, 1967, 158(3800):536.
Stucken et al., "The smallest known genomes of multicellular and toxic cyanobacteria: comparison, minimal gene sets for linked traits and the evolutionary implications," PLoS One, 2010, 5:e9235, 15 pages.
Subtil et al., "Secretion of Predicted Inc Proteins of Chlamydia pneumoniae by a Heterologous Type Ill Machinery," Molecular Microbiology, Feb. 2001, 39(3):792-800.
Suh et al., "Functional expression of the FeMo-cofactor-specific biosynthetic genes nifEN as a NifE-N fusion protein synthesizing unit in Azotobacter vinelandii," Biochem. Biophys. Res. Comm., 2002, 299:233-240.
Suzuki et al., "Immune-mediated motor polyneuropathy after hematopoietic stem cell transplantation," Bone Marrow Transplant., Aug. 2007, 40(3):289-91.

Swain et al., "Nitrogen fixation and its improvement through genetic engineering," J. Global Biosciences, 2013, 2(5): 98-112.
Tamsir et al., "Robust multicellular computing using genetically encoded NOR gates and chemical 'wires'," Nature, 2011, 469(7329):212-215.
Tan, "A synthetic biology challenge: making cells compute," Mol. Biosyst., Mar. 2007:343-353.
Temme et al., "Designing and Engineering Complex Behavior in Living Machines," Doctoral Dissertation, Oct. 2011, Retrieved from URL <escholarship.org/uc/item/1r41x99s>, 75 pages.
Temme et al., "Induction and relaxation dynamics of the regulatory network controlling the type III secretion system encoded within *Salmonella* pathogenicity island 1," J. Mol. Biol., 2008, 377(1):47-61.
Temme et al., "Modular control of multiple pathways using engineered orthogonal T7 polymerases," Nucleic Acids Res, Sep. 2012, 40(17):8773-81.
Temme et al., "Refactoring the nitrogen fixation gene cluster from *Klebsiella oxytoca*," Proc. Natl. Acad. Sci. USA, 2012, 109(18):7085-7090.
Thiel et al., "Characterization of genes for a second Modependent nitrogenase in the cyanobacterium *Anabaena variabilis*," J. Bact., 1997, 179:5222-5225.
Thomas et al., "Ammonium Excretion by an I-Methionine-dl-Sulfoximine-Resistant Mutant of the Rice Field Cyanobacterium Anabaena siamensis," Appl Environ Microbiol., Nov. 1990, 56(11):3499-3504.
Tijssen, "Laboratory Techniques In Biochemistry And Molecular Biology," Elsevier, 1993, 24:65 pages.
Tilman et al., "Global food demand and the sustainable intensification of agriculture," PNAS, 2011, 108:20260-20264.
Timmer et al., "Ammonia sensors and their applications—a review," Sensors and Actuators B: Chemical, 2005, 107(2):666-677.
Triplett, "Diazotrophic endophytes: progress and prospects for nitrogen fixation in monocots," Plant and Soil, 1996, 186:29-38.
Tritt et al., "An Integrated Pipeline for de Novo Assembly of Microbial Genomes," PLoS One, Sep. 2012, 7(9):e42304, 9 pages.
Ueda et al., "Remarkable N2-Fixing Bacterial Diversity Detected in Rice Roots by Molecular Evolutionary Analysis of nifH Gene Sequences," Journal of Bacteriology, Mar. 1995, 177:1414-1417.
Uozumi et al., "Cloning and Expression of the nif A Gene of *Klebsiella oxytoca* in *K. pneumoniae* and *Azospirillum lipoferum*," Agricultural and Biological Chemistry, 1986, 50(6):1539-1544.
Van Dongen, "Performance criteria for graph clustering and Markov cluster experiments," CWI, 2000, 36 pages.
Van Heeswijk et al., "Nitrogen Assimilation in *Escherichia coli*: Putting Molecular Data into a Systems Perspective," Microbiology and Molecular Biology Reviews, Dec. 2013, 77(4):628-695.
Vernon et al., "Analysis of 16S rRNA gene sequences and circulating cell-free DNA from plasma of chronic fatigue syndrome and non-fatigued subjects," BMC Microbiology, Feb. 2002:39, 6 pages.
Villa et al., "Azotobacter vinelandii siderophore can provide nitrogen to support the culture of the green algae neochloris oleoabundans and scenedesmus," FEMS Microbial. Lett., 2014, 351(1):70-77.
Villalobos et al., "Gene Designer: a synthetic biology tool for constructing artificial ONA segments," BMC Bioinformatics, Jul. 2006:285, 8 pages.
Voight, "Genetic parts to program bacteria," Current Opinion in Biotechnology, 2006, 17(5):548-557.
Voigt, "Gaining Access: Rebuilding Genetics from the Ground Up," Institute of Medicine Board on Global Health Forum on Microbial Threats, Mar. 14, 2011. Retrieved from URL<iom.edu//media/Files/ActivityFiles/PublicHealth/MicrobialThreats/2011-MAR- 14Noigt. pdf, 82 pages.
Wang et al., "A minimal nitrogen fixation gene cluster from *paenibacillus* sp. WLY78 enables expression of active nitrogenase in *Escheichia coli*," Plos Genetics, 2013, 9(10):1-11.
Wang et al., "Biofilm formation enables free-living nitrogen-fixing rhizobacteria to fix nitrogen under aerobic conditions," The ISME Journal, Jul. 11, 2017:1602-1613.
Wang et al., "Ligand-inducible and liver-specific target gene expression in transgenic mice," Nat Biotechnol., Mar. 1997, 15(3):239-43.

(56) References Cited

OTHER PUBLICATIONS

Wang et al., "Positive and negative regulation of gene expression in eukaryotic cells with an inducible transcriptional regulator," Gene Ther., May 1997, 4(5):432-441.
Wang et al., "Programming cells by multiplex genome engineering and accelerated evolution," Nature, Aug. 2009, 460(7257):894-8.
Wang et al., "Roles of poly-3-hydroxybutyrate (PHB) and glycogen in symbiosis of Sinorhizobium meliloti with *Medicago* sp.," Microbiology, Feb. 2007, 153(2):388-398.
Wang et al., "Using Synthetic biology to distinguish and overcome regulatory and functional barriers related to nitrogen fixation," PLoS One, 2013, 8(7):e68677, 11 pages.
Watanabe et al., "Chapter 15. Plasmid-borne gene cluster assemblage and heterologous biosynthesis of nonribosomal peptides in *Escherichia coli*," Methods Enzymol., 2009, 458:379-99.
Watanabe et al., "Total biosynthesis of antitumor nonribosomal peptides in *Escherichia coli*," Nature Chemical Biology, Feb. 2006:423-428.
Weber et al., "A modular cloning system for standardized assembly of multigene constructs," PLoS One, Feb. 2011, 6(2):e16765, 11 pages.
Wei et al., "Endophytic nitrogen-fixing Klebsiella variicola strain DX120E promotes sugarcane growth," Biology and fertility of soils, 2014, 50:657-666.
Welch et al., "Design Parameters to Control Synthetic Gene Expression in *Escherichia coli*," PLoS One, 2009, 4(9):e7002, 10 pages.
Wells, "Additivity of mutational effects in proteins," Biochemistry, 1990, 29:8509-8517.
Wen et al., "Enabling Biological Nitrogen Fixation for Cereal Crops in Fertilized Fields," ACS Synth. Biol., Dec. 2021, 10(12):3264-3277.
Wenzel et al., "Recent developments towards the heterologous expression of complex bacterial natural product biosynthetic pathways," Curr. Opin. Biotechnol., 2005, 16(6):594-606.
Werner et al., "Fast track assembly of multigene constructs using Golden Gate cloning and the MoClo system," Bioeng Bugs. Jan. 2012, 3(1):38-43.
Widmaier et al., "Engineering the *Salmonella* type III secretion system to export spider silk monomers," Mol. Syst. Biol., May 2009:309, 9 pages.
Wimpenny et al., "Community structure and co-operation in biofilms," 59th Symposium of the Society for General Microbiology, Allison et al. (eds.), Sep. 2000, 23 pages.
Witkowski et al., "Conversion of a β-Ketoacyl synthase to a malonyl decarboxylase by replacement of the active-site cysteine with glutamine," Biochemistry, Sep. 1999, 38(36):11643-50.
Woolbright et al., "Novel insight into mechanisms of cholestatic liver injury," World J Gastroenterol., Sep. 2012, 18(36):4985-93.
Wootton et al., "Statistics of local complexity in amino acid sequences and sequence databases," Computers & Chemistry, Jun. 1993, 17(2):149-163.
Wu et al., "Effects of biofertilizer containing N-fixer, P and K solubilizers and AM fungi on maize growth: a greenhouse trial," Geodernna, Mar. 2005, 125(1-2):155-166.
Wu et al., "Multivariate modular metabolic engineering of *Escherichia coli* to produce resveratrol from L-tyrosine," J. Biotechnol., 2013, 167:404-411.
Wu et al., "Root exudates from two tobacco cultivars affect colonization of *Ralstonia solanacearum* and the disease index," European Journal of Plant Pathology, 2014, 141(4):667-677.

Xie et al., "Interaction between NifL and NifA in the nitrogen-fixing Pseudomonas stutzeri A1501," Microbiology (Reading), Dec. 2006, 152(Pt 12):3535-3542.
Xu et al., "ePathBrick: a synthetic biology platform for engineering metabolic pathways in *E. coli*.," ACS Synth. Biol., Jan. 2012:256-266.
Yan et al., "Global transcriptional analysis of nitrogen fixation and ammonium repression in root-associated Pseudomonas stutzeri A1501," BMC Genomics, Jan. 2010, 11(11):1-13.
Yao et al., "Complementation analysis of heterologous nifA genes to nifA mutants of Sinorhizobium pallida," Chinese Science Bulletin, Oct. 2006, 51(19):2258-2264, 2 pages (English abstract only).
Yarza et al., "Uniting the classification of cultured and uncultured bacteria and archaea using 16S rRNA gene sequences," Nature Rev. Micro., Dec. 2014:635-345.
Ye et al., "Primer-BLAST: a tool to design target-specific primers for polymerase chain reaction," BMC Bioinformatics., Jun. 2012, 13(134):1-11.
Yokobayashi et al., "Directed evolution of a genetic circuit," Proc. Natl. Acad. Sci. USA, 2002, 99(26):16587-16591.
Yoshida et al., "Atmospheric dinitrogen fixation in the flooded rice *rhizosphere* as determined by the N-15 isotope technique," Soil Science and Plant Nutrition, Dec. 1980, 26(4):551-559.
Yu et al., "Recombineering Pseudomonas protegens CHAO: An innovative approach that improves nitrogen fixation with impressive bactericidal potency," Microbiological Research, Jan. 2019, 218:58-65.
Zaslaver et al., "Optimal gene partition into operons correlates with gene functional order," Phys. Biol., 2006, 3(3):183-189.
Zazopoulos et al., "A genomics-guided approach for discovering and expressing cryptic metabolic pathways," Nat. Biotechnol., 2003, 21(2):187-190.
Zehr et al., "New Nitrogen-Fixing Microorganisms Detected in Oligotrophic Oceans by Amplification of Nitrogenase (nifH) Genes," Appl Environ Microbiol., Sep. 1998, 64(9):3444-3450.
Zehr Lab NifH database, retrieved from URL <https://wwwzehr.pmc.ucsc.edu/nifH_Database_Public/>, Apr. 4, 2014, 1 page.
Zhang et al., "GlnD Is Essential for NifA Activation, NtrB/NtrC-Regulated Gene Expression, and Posttranslational Regulation of Nitrogenase Activity in the Photosynthetic, Nitrogen-Fixing Bacterium Rhodospirillum rubrum," J. Bacteriol., Feb. 2005, 187(4):1254-1265.
Zhang et al., "Influence of different factors on the nitrogenase activity of the engineered *Escherichia coli* 78-7," World J Microbiol Biotechnol., Jun. 2015, 31(6):921-7.
Zhang et al., "Involvement of the ammonium transporter AmtB in nitrogenase regulation and ammonium excretion in Pseudomonas stutzeri A 1501," Res. Microbial, Jun. 2012, 163(5):332-339.
Zhang et al., "Mutagenesis and functional characterization of the four domains of GlnD, a bifunctional nitrogen sensor protein," Journal of Bacteriology, Jun. 2010, 192(11):2711-2721.
Zhang et al., "Mutagenesis and Functional Characterization of the glnB, glnA, and nifA Genes from the Photosynthetic Bacterium Rhodospirillum rubrum," Journal of Bacteriology, Feb. 2000, 182(4):983-992.
Zhao et al., "Evidence for nifU and nifS participation in the biosynthesis of the iron-molybdenum cofactor of nitrogenase," J. Biol. Chem., 2007, 282(51):37016-37025.
Zhong et al., "Nitrous oxide emissions associated with nitrogen fixation by grain legumes," Soil Biology and Biochemistry, Nov. 2009, 41(11): 2283-2291 (Abstract Only).
Zomer, "PPP: Perform Promoter Prediction," retrieved from URL <http://bioinformatics.biol.rug.nl/websoftware/ppp/ppp_start.php>, 2011, 2 pages.

MEASUREMENT OF NITROGEN FIXATION AND INCORPORATION

CROSS-REFERENCE TO RELATED APPLICATIONS

This application is a National Stage application under 35 U.S.C. § 371 of International Application No. PCT/US2020/031199 having an International Filing Date of May 1, 2020. The disclosure is incorporated herein by reference in its entirety.

TECHNICAL FIELD

This disclosure relates systems and methods for measurement of incorporation of species, including nutrients such as nitrogen, in plant tissues.

BACKGROUND

Biological nitrogen fixation is a process in which microorganisms such as bacteria convert atmospheric nitrogen gas ($N_2$) into ammonia ($NH_3$) via reduction mediated by the enzyme nitrogenase. Ammonia is soluble in aqueous media and can be incorporated into organic matter such as plant tissues. Successful provision of nitrogen to crop plants is a significant contributing factor to observed yields.

SUMMARY

The present disclosure features systems and methods for measuring nitrogen incorporation by plants. The systems and methods can adjust compositions of gas mixtures delivered to growing plants, and in particular, isotopic ratios of different elements in the gas mixtures. By adjusting the isotopic ratio of atomic nitrogen in a nitrogen gas mixture, for example, nitrogen that is fixed and taken up by plant tissues can be directly and continuously measured. A wide variety of other growth and environmental conditions can also be controlled and adjusted so that nitrogen fixation and incorporation under many different conditions can be evaluated. In addition, the systems and methods described can be used to interrogate nitrogen incorporation in different types of plant tissues, including roots, newly emerged whorl tissue, top-collared leaf tissue, and early vegetative tissue.

Naturally occurring microorganisms such as various strains of bacteria participate in nitrogen gas fixation. A variety of different bacterial strains have been genetically engineered, with specific mutations targeting genes that regulate various pathways involved in nitrogen fixation activity. The systems and methods described herein can be used to evaluate both naturally occurring and engineered microorganisms such as bacteria for their nitrogen-fixing activity. In particular, seeds and plants inoculated with particular microorganisms can be grown and analyzed to obtain quantitative measurements of nitrogen in plant tissues. These measurements can be used to evaluate the ability of the microorganisms to generate nitrogen in reduced form from atmospheric nitrogen gas, and to identify particular strains of microorganisms as nitrogen-fixing or non-nitrogen-fixing.

In an aspect, the disclosure features systems for plant culture that include: a chamber including one or more walls enclosing a spatial volume internal to the chamber, where the one or more walls include a surface for supporting a plant within the enclosed spatial volume; a gas delivery apparatus, including at least one gas source; a nutrient delivery apparatus including a reservoir; a sampling apparatus connected to a port formed in the one or more walls; and a controller connected to the gas delivery apparatus and the nutrient delivery apparatus, and configured so that during operation of the system, with a plant entirely positioned within the enclosed spatial volume of the chamber, the controller activates the nutrient delivery apparatus to deliver an aqueous growth medium to the plant, and activates the gas delivery apparatus to deliver into the enclosed spatial volume a mixture of isotopically-substituted gases.

Embodiments of the systems can include any one or more of the following features.

A height of the enclosed spatial volume measured between the surface and a wall or wall portion opposite the surface can be at least 0.5 meters (e.g., at least 3.0 meters). The enclosed spatial volume can be at least 500 L (e.g., at least 1000 L). When the chamber is filled with a gas at a pressure of 1.5 atmospheres, a leakage rate of the gas from the chamber can be less than 0.5 L/day (e.g., less than 0.1 L/day). When the chamber is filled with a gas at a pressure p at a first time, the one or more walls of the chamber can be sufficiently impermeable so that the gas pressure within the chamber at a second time at least 7 days after the first time is 0.80p or more (e.g., 0.90p or more).

The gas delivery apparatus can include a valve connected to the controller, and during operation of the system, the controller can be configured to activate the valve to regulate gas delivery from the gas delivery apparatus. During operation of the system, the at least one gas source can include a source of nitrogen gas for which an isotopic ratio of $^{15}N$ to $^{14}N$ is greater than a ratio of $^{15}N$ to $^{14}N$ in atmospheric nitrogen gas. During operation of the system, the at least one gas source can include a source of nitrogen gas for which an isotopic ratio of $^{13}N$ to $^{14}N$ is greater than a ratio of $^{13}N$ to $^{14}N$ in atmospheric nitrogen gas. During operation of the system, the controller can be configured to adjust the isotopic ratio of $^{15}N$ to $^{14}N$ in the chamber. During operation of the system, the nitrogen gas mixture in the chamber can include at least 0.1 atom % $^{15}N$ (e.g., at least 0.5 atom % $^{15}N$).

During operation of the system, the control can be configured to adjust the isotopic ratio of $^3N$ to $^{14}N$ in the chamber. During operation of the system, the nitrogen gas mixture in the chamber can include at least 0.1 atom % $^{13}N$ (e.g., at least 0.5 atom % $^{13}N$).

The systems can include a gas detector connected to the controller and configured to generate a measurement signal in response to a presence of one or more gas species within the chamber. The gas detector can be configured to generate a measurement signal representing the isotopic ratio of $^{15}N$ to $^{14}N$ in the chamber, and the controller can be configured to regulate delivery of the nitrogen gas into the chamber based on the measurement signal.

The systems can include a gas removal apparatus connected to a port formed in the one or more walls. The gas removal apparatus can include an oxygen gas scrubber. The systems can include a gas detector connected to the controller and configured to generate a measurement signal representing an amount of oxygen gas in the chamber. The controller can be connected to the gas removal apparatus, and during operation of the system, the controller can be configured to activate the gas removal apparatus based on the measurement signal to adjust an oxygen gas concentration in the chamber.

During operation of the system, the gas delivery apparatus can include a source of carbon dioxide gas. The systems can include a gas detector connected to the controller and configured to generate a measurement signal representing an amount of carbon dioxide gas in the chamber. During operation of the system, the controller can be configured to regulate carbon dioxide delivery into the chamber based on the measurement signal.

The systems can include a temperature sensor connected to the controller and configured to generate a measurement signal representing a temperature within the chamber, and a temperature regulator connected to the controller, where during operation of the system, the controller can be configured to activate the temperature regulator to control the temperature within the chamber based on the measurement signal. The temperature regulator can include a heating element, a cooling element, or both heating and cooling elements.

The systems can include a gas detector connected to the controller and configured to generate a measurement signal in response to a presence of one or more gas species within the chamber. The gas detector can be configured to generate a measurement signal representing an amount of nitrous oxide in the chamber. The gas detector can be configured to generate a measurement signal representing an amount of ammonia in the chamber.

The systems can include an altitude sensor connected to the controller and configured to transmit altitude information to the controller, where the controller can be configured to regulate gas delivery into the chamber based on the altitude information. The systems can include a light source connected to the controller, where during operation of the system, the controller can be configured to activate the light source to deliver light to the enclosed spatial volume in the chamber. The systems can include a humidity sensor connected to the controller and configured to transmit information about humidity within the enclosed spatial volume to the controller, and during operation of the system, the controller can be configured to adjust humidity within the enclosed spatial volume based on the humidity information. The systems can include at least one of a humidifier and a de-humidifier connected to a port formed in the one or more walls, and connected to the controller, where during operation of the system, the controller can be configured to activate the at least one of the humidifier and the de-humidifier to adjust the humidity within the enclosed spatial volume.

The nutrient delivery apparatus can include a valve connected to the controller, and where during operation of the system, the controller can be configured to activate the valve to regulate delivery of a nutrient medium from the nutrient delivery apparatus.

During operation of the system, with a plant present in the chamber, the controller can be configured to obtain nutrient information associated with the plant, and regulate delivery of the nutrient medium to the plant based on the nutrient information.

The systems can include a growth monitoring apparatus connected to the controller and configured to generate a measurement signal including information about growth of a plant within the chamber. The growth monitoring apparatus can include a radiation source configured to direct illumination light to be incident on a plant within the chamber, and a detector configured to detect light emitted from the plant. The detector can be configured to detect light emitted from the plant in three different spectral bands, a first one of the spectral bands having a local maximum wavelength between 635 nm and 700 nm, a second one of the spectral bands having a local maximum wavelength between 520 nm and 560 nm, and a third one of the spectral bands having a local maximum wavelength between 450 nm and 490 nm. The detector can be configured to detect light emitted from the plant in multiple distinct spectral bands, each including a local maximum spectral wavelength. The multiple distinct spectral bands can include three or more bands (e.g., five or more bands).

The detector can be configured to obtain a hyperspectral image of at least a portion of the plant, the hyperspectral image including, at each of multiple pixels, distinct light intensity measurements corresponding to different wavelength bands. The detector can be configured to obtain an image of at least a portion of the plant, the image representing light emitted from the portion of the plant within a near-infrared spectral band having a local maximum wavelength between 800 nm and 1400 nm. The detector can be configured to obtain an image of at least a portion of the plant, the image representing light emitted from the portion of the plant within a short-wavelength infrared spectral band having a local maximum wavelength between 1400 nm and 3000 nm. The detector can be configured to obtain an image of at least a portion of the plant, the image representing light emitted from the portion of the plant within an infrared spectral band. The detector can be configured to detect fluorescent light emitted from at least a portion of the plant. The the radiation source can be a laser scanner.

The growth monitoring apparatus can include a scale positioned on or integrated into the surface, and configured to measure a mass of the plant.

The systems can include a soil moisture detector connected to the controller and configured to generate a measurement signal including information about a percentage of water in a soil within the chamber. The systems can include a scale connected to the controller and positioned on or integrated into the surface, and configured to measure a mass of a soil supported by the scale. The controller can be configured to determine information about a percentage of water in the soil based on the soil mass.

The systems can include at least one chemical sensor connected to the controller and configured to generate a measurement signal including information about an analyte within the chamber. The information about the analyte can include an ammonia concentration within the chamber, an amount of at least one of nitrate ions and nitrate salts within the chamber, a nitrous oxide concentration within the chamber, and/or a carbon dioxide concentration within the chamber.

The systems can include at least one sensor connected to the controller and configured to generate a measurement signal including information about a change in plant mass within the chamber. The at least one sensor can include a touch-sensitive sensor.

The systems can include a fluid removal mechanism including a conduit connected to or extending through a port formed in the one or more walls and configured to extract a fluid from the chamber. The fluid removal mechanism can include a fluid pump configured to cause a fluid to flow through the fluid removal mechanism and out of the chamber. The fluid removal mechanism can include a pressure-reducing device that draws fluid through the fluid removal mechanism and out of the chamber. The conduit can extend into the chamber and can be configured to extract fluid from a plant within the chamber. The conduit can extend into the chamber and can be configured to extract fluid from a soil in which a plant is growing within the chamber. The conduit can extend into the chamber and can be configured to capture a portion of a growth medium delivered to a plant within the chamber.

The extracted fluid can be a liquid, a gas, or a mixture of a liquid and a gas.

The systems can include a fluid analysis apparatus connected to the fluid removal mechanism. The fluid analysis apparatus can include a mass spectrometry apparatus. The fluid analysis apparatus can includes a light source configured to direct illumination light to be incident on at least a portion of the extracted fluid, and a detector configured to measure light emitted from the at least a portion of the extracted fluid in response to the illumination light.

The sampling apparatus can include an auxiliary chamber connected through a sealing mechanism to the chamber such that when the sealing mechanism is deployed, an interior of the auxiliary chamber is disconnected from the enclosed spatial volume of the chamber. The sampling apparatus can include a cover connected through a sealing mechanism to the chamber.

The systems can include one or more gloves connected through sealing mechanisms to one or more ports in the one or more walls.

The gas delivery apparatus can be positioned within the chamber. The gas delivery apparatus can be connected to at least one port formed in the one or more walls.

The nutrient delivery apparatus can be positioned within the chamber. The nutrient delivery apparatus can be connected to at least one port formed in the one or more walls.

The systems can include an inoculation mechanism configured to deliver an inoculation composition to a plant enclosed within the spatial volume. The inoculation mechanism can include a reservoir for storing the inoculation composition. The inoculation mechanism can include a syringe. The inoculation mechanism can include a conduit connected to the reservoir and a metering mechanism connected to the controller, where during operation of the system, the controller can be configured to deliver a metered volume of the inoculation composition to the plant by activating the metering mechanism. The metering mechanism can include a pump and a valve. The systems can include a port located in the one or more walls, where the port is configured to be selectively opened to deliver an inoculation composition to a plant enclosed within the spatial volume.

The gas delivery apparatus can include an acetylene gas source, and the system can include an ethylene detector connected to the controller. The controller can be configured to measure a rate of acetylene reduction by a microorganism present in a soil within the chamber by activating the valve of the gas delivery apparatus to deliver a quantity of acetylene to the soil, after an elapsed measurement time, activating the ethylene detector to measure an amount of ethylene generated from the acetylene gas by the microorganism, and determining a rate of acetylene reduction based on the amount of ethylene generated and the elapsed time.

Embodiments of the systems can also include any of the other features described herein, including any combinations of features described in connection with different embodiments, except as expressly stated otherwise.

In another aspect, the disclosure features systems for plant culture that include: a chamber including one or more walls enclosing a spatial volume internal to the chamber, where the one or more walls include a surface for supporting a plant within the enclosed spatial volume; a gas delivery apparatus including a nitrogen gas source and a carbon dioxide gas source; a gas removal apparatus connected to a port formed in the one or more walls; a gas detection apparatus including one or more sensors configured to generate measurement signals including information about amounts of oxygen and carbon dioxide in the chamber; a nutrient delivery apparatus including a reservoir and a fluid conduit connected to the reservoir; and a controller connected to the gas delivery apparatus, the gas removal apparatus, the gas detection apparatus, and the nutrient delivery apparatus, and configured so that during operation of the system, the controller activates the nutrient delivery apparatus to deliver a nutrient medium to a plant within the chamber to facilitate growth of the plant, and activates the gas delivery apparatus and gas removal apparatus to adjust concentrations of oxygen, carbon dioxide, and nitrogen in the chamber, and to adjust an isotopic ratio of $^{15}N$ to $^{14}N$ in the chamber to a value greater than an isotopic ratio of $^{15}N$ to $^{14}N$ in atmospheric nitrogen gas.

Embodiments of the systems can include any one or more of the following features.

A height of the enclosed spatial volume measured between the surface and a wall or wall portion opposite the surface can be at least 0.5 meters (e.g., at least 3.0 meters). The enclosed spatial volume can be at least 500 L (e.g., at least 1000 L). When the chamber is filled with a gas at a pressure of 1.5 atmospheres, a leakage rate of the gas from the chamber can be less than 0.5 L/day (e.g., less than 0.1 L/day). When the chamber is filled with a gas at a pressure p at a first time, the one or more walls of the chamber are sufficiently impermeable so that the gas pressure within the chamber at a second time at least 7 days after the first time can be 0.80p or more (e.g., 0.90p or more).

The gas delivery apparatus can include a valve connected to the controller, and during operation of the system, the controller can be configured to activate the valve to regulate gas delivery from the gas delivery apparatus. During operation of the system, the at least one gas source can include a source of nitrogen gas for which an isotopic ratio of $^{15}N$ to $^{14}N$ is greater than a ratio of $^{15}N$ to $^{14}N$ in atmospheric nitrogen gas. The adjusted isotopic ratio of $^{15}N$ to $^{14}N$ can be greater than 0.01.

Following adjustment of the isotopic ratio of $^{15}N$ to $^{14}N$ in the chamber, the nitrogen gas in the chamber includes at least 0.1 atom % $^{15}N$ (e.g., at least 0.5 atom % $^{15}N$).

The gas detection apparatus can include a gas detector connected to the controller and configured to generate a measurement signal in response to a presence of one or more gas species within the chamber. The gas detector can be configured to generate a measurement signal representing an isotopic ratio of $^{15}N$ to $^{14}N$ in the chamber, and the controller can be configured to adjust the isotopic ratio in the chamber based on the measurement signal.

The gas removal apparatus can include an oxygen gas scrubber. The gas detection apparatus can includes a gas detector configured to generate a measurement signal representing an amount of oxygen gas in the chamber. The controller can be configured to adjust the oxygen gas concentration in the chamber based on the measurement signal.

The gas detection apparatus can includes a gas detector configured to generate a measurement signal representing an amount of carbon dioxide gas in the chamber. The controller can be configured to adjust the carbon dioxide concentration in the chamber based on the measurement signal.

The systems can include a temperature sensor connected to the controller and configured to generate a measurement signal representing a temperature within the chamber, and a temperature regulator connected to the controller, where during operation of the system, the controller can be configured to activate the temperature regulator to control the temperature within the chamber based on the measurement signal. The temperature regulator can include a heating element, a cooling element, or both heating and cooling elements.

The gas detection apparatus can include at least one gas configured to generate a measurement signal in response to a presence of one or more gas species within the chamber. The gas detector can be configured to generate a measurement signal representing an amount of nitrous oxide in the chamber and/or an amount of ammonia in the chamber.

The systems can include an altitude sensor connected to the controller and configured to transmit altitude information to the controller, where the controller is configured to regulate gas delivery into the chamber based on the altitude information.

The systems can include a light source connected to the controller, where during operation of the system, the controller can be configured to activate the light source to deliver light to the enclosed spatial volume in the chamber. The systems can include a humidity sensor connected to the controller and configured to transmit information about humidity within the enclosed spatial volume to the controller, where during operation of the system, the controller can be configured to adjust humidity within the enclosed spatial volume based on the humidity information.

The systems can include at least one of a humidifier and a de-humidifier connected to a port formed in the one or more walls, and connected to the controller, where during operation of the system, the controller can be configured to activate the at least one of the humidifier and the de-humidifier to adjust the humidity within the enclosed spatial volume.

The nutrient delivery apparatus can include a valve connected to the controller, where during operation of the system, the controller can be configured to activate the valve to regulate the delivery of the nutrient medium from the nutrient delivery apparatus. During operation of the system, with a plant present in the chamber, the controller can be configured to obtain nutrient information associated with the plant. and regulate delivery of the nutrient medium to the plant based on the nutrient information.

The systems can include a growth monitoring apparatus connected to the controller and configured to generate a measurement signal including information about growth of a plant within the chamber. The growth monitoring apparatus can include a radiation source configured to direct illumination light to be incident on a plant within the chamber, and a detector configured to detect light emitted from the plant. The detector can be configured to detect light emitted from the plant in three different spectral bands, a first one of the spectral bands having a local maximum wavelength between 635 nm and 700 nm, a second one of the spectral bands having a local maximum wavelength between 520 nm and 560 nm, and a third one of the spectral bands having a local maximum wavelength between 450 nm and 490 nm. The detector can be configured to detect light emitted from the plant in multiple distinct spectral bands, each including a local maximum spectral wavelength. The multiple distinct spectral bands can include three or more bands (e.g., five or more bands).

The detector can be configured to obtain a hyperspectral image of at least a portion of the plant, the hyperspectral image including, at each of multiple pixels, distinct light intensity measurements corresponding to different wavelength bands. The detector can be configured to obtain an image of at least a portion of the plant, the image representing light emitted from the portion of the plant within a near-infrared spectral band having a local maximum wavelength between 800 nm and 1400 nm. The detector can be configured to obtain an image of at least a portion of the plant, the image representing light emitted from the portion of the plant within a short-wavelength infrared spectral band having a local maximum wavelength between 1400 nm and 3000 nm. The detector can be configured to obtain an image of at least a portion of the plant, the image representing light emitted from the portion of the plant within an infrared spectral band. The detector can be configured to detect fluorescent light emitted from at least a portion of the plant. The radiation source can be a laser scanner.

The growth monitoring apparatus can include a scale positioned on or integrated into the surface, and configured to measure a mass of the plant.

The systems can include a soil moisture detector connected to the controller and configured to generate a measurement signal including information about a percentage of water in a soil within the chamber. The systems can include a scale connected to the controller and positioned on or integrated into the surface, and configured to measure a mass of a soil supported by the scale. The controller can be configured to determine information about a percentage of water in the soil based on the soil mass.

The systems can include at least one chemical sensor connected to the controller and configured to generate a measurement signal including information about an analyte within the chamber. The information about the analyte can include an ammonia concentration within the chamber, an amount of at least one of nitrate ions and nitrate salts within the chamber, and a nitrous oxide concentration within the chamber.

The systems can include at least one sensor connected to the controller and configured to generate a measurement signal including information about a change in plant mass within the chamber. The at least one sensor can include a touch-sensitive sensor.

The systems can include a fluid removal mechanism including a conduit connected to or extending through a port formed in the one or more walls and configured to extract a fluid from the chamber. The fluid removal mechanism can include a fluid pump configured to cause a fluid to flow through the fluid removal mechanism and out of the chamber. The fluid removal mechanism can include a pressure-reducing device that draws fluid through the fluid removal mechanism and out of the chamber. The conduit can extend into the chamber and can be configured to extract fluid from a plant within the chamber. The conduit can extend into the chamber and can be configured to extract fluid from a soil in which a plant is growing within the chamber. The conduit can extend into the chamber and can be configured to capture a portion of a growth medium delivered to a plant within the chamber.

The extracted fluid can be a liquid, a gas, or a mixture of a liquid and a gas.

The systems can include a fluid analysis apparatus connected to the fluid removal mechanism. The fluid analysis apparatus can include a mass spectrometry apparatus. The fluid analysis apparatus can include a light source configured to direct illumination light to be incident on at least a portion of the extracted fluid, and a detector configured to measure light emitted from the at least a portion of the extracted fluid in response to the illumination light.

The systems can include a sampling apparatus connected to a port formed in the one or more walls. The sampling apparatus can include an auxiliary chamber connected through a sealing mechanism to the chamber such that when the sealing mechanism is deployed, an interior of the auxiliary chamber is disconnected from the enclosed spatial volume of the chamber. The sampling apparatus can include a cover or lid connected through a sealing mechanism to the chamber.

The systems can include one or more gloves connected through sealing mechanisms to one or more ports in the one or more walls.

The gas delivery apparatus can be positioned within the chamber. The gas delivery apparatus can be connected to at least one port formed in the one or more walls. The nutrient delivery apparatus can be positioned within the chamber. The nutrient delivery apparatus can be connected to at least one port formed in the one or more walls.

The systems can include an inoculation mechanism configured to deliver an inoculation composition to a plant enclosed within the spatial volume. The inoculation mechanism can include a reservoir for storing the inoculation composition. The inoculation mechanism can include a syringe. The inoculation mechanism can include a conduit connected to the reservoir and a metering mechanism connected to the controller, where during operation of the system, the controller can be configured to deliver a metered volume of the inoculation composition to the plant by activating the metering mechanism. The metering mechanism can include a pump and a valve. The systems can include a port located in the one or more walls, where the port is configured to be selectively opened to deliver an inoculation composition to a plant enclosed within the spatial volume.

The gas delivery apparatus can include an acetylene gas source, and the system can include an ethylene detector connected to the controller. The controller can be configured to measure a rate of acetylene reduction by a microorganism present in a soil within the chamber by activating the valve of the gas delivery apparatus to deliver a quantity of acetylene to the soil, after an elapsed measurement time, activating the ethylene detector to measure an amount of ethylene generated from the acetylene gas by the microorganism, and determining a rate of acetylene reduction based on the amount of ethylene generated and the elapsed time.

Embodiments of the systems can also include any of the other features described herein, including any combinations of features described in connection with different embodiments, except as expressly stated otherwise.

In another aspect, the disclosure features methods of detecting nitrogen incorporation in a plant, the methods including: positioning a test plant in a support medium within an enclosed chamber of a plant culture system; adjusting a composition of a nitrogen gas mixture within the chamber so that a ratio of at least two nitrogen isotopes is different from a naturally occurring atmospheric ratio of the isotopes; delivering an aqueous growth medium to the test plant to cause growth of the test plant over a growth period; performing an isotope analysis of a test plant tissue to determine relative amounts of the at least two nitrogen isotopes in the test plant tissue; and comparing the relative amounts of the at least two nitrogen isotopes in the test plant tissue to reference information to detect nitrogen incorporation in the test plant.

Embodiments of the methods can include any one or more of the following features.

Adjusting the composition of nitrogen gas can include activating a gas delivery apparatus of the plant culture system to deliver nitrogen gas including a ratio of the at least two nitrogen isotopes that differs from a naturally occurring ratio of the at least two isotopes in atmospheric nitrogen gas. The at least two nitrogen isotopes can include $^{15}N$ and $^{14}N$, or $^{13}N$ and $^{14}N$, or $^{15}N$, $^{14}N$, and $^{13}N$. The delivered nitrogen gas can include at least 20 atom % $^{15}N$ (e.g., at least 50 atom % $^{15}N$, at least 90 atom % $^{15}N$). Following adjustment of the composition of the nitrogen gas mixture, the nitrogen gas mixture can include at least 0.1 atom % $^{15}N$ or $^{13}N$ (e.g., at least 0.3 atom % $^{15}N$ or $^{13}N$, at least 0.5 atom % $^{15}N$ or $^{13}N$).

The aqueous growth medium can include a modified Hoaglund's solution. The growth period can include at least 7 days. The test plant tissue can includes root tissue and/or newly emerged whorl tissue and/or top-collared leaf tissue.

The methods can include harvesting the test plant tissue. The methods can include drying the harvested tissue for a drying time, grinding the dried, harvested tissue to form a powder, and performing the isotope analysis on the powder.

The reference information can be derived from tissue of a reference plant. The methods can include growing the reference plant with the test plant in the enclosed chamber of the plant culture system. Growing the reference plant can include positioning the reference plant in a growth medium within the enclosed chamber of the plant culture system, and delivering an aqueous growth medium to the reference plant to cause growth of the reference plant over the growth period. The aqueous growth media delivered to the test and reference plants can be the same.

The methods can include prior to positioning the test and reference plants within the enclosed chamber of the plant culture system, inoculating the test plant or a seed precursor of the test plant with a bacterial suspension. The bacterial suspension can include one or more nitrogen-fixing bacteria.

The methods can include determining the reference information by performing an isotope analysis of the reference plant tissue to determine relative amounts of the at least two nitrogen isotopes in the reference plant tissue.

The methods can include, during growth of the test plant over the growth period, measuring a humidity within the enclosed chamber of the plant culture system, and activating at least one of a humidifier and a de-humidifier to adjust the humidity according to a humidity reference value for the test plant. The methods can include, during growth of the test plant over the growth period, measuring an oxygen concentration within the enclosed chamber of the plant culture system, and activating a gas removal apparatus of the plant culture system to adjust the oxygen concentration according to a reference value for the test plant. The gas removal apparatus can include an oxygen scrubber.

The methods can include, during growth of the test plant over the growth period, measuring a carbon dioxide concentration within the enclosed chamber of the plant culture system, and activating a carbon dioxide gas source to adjust the carbon dioxide concentration according to a reference value for the test plant. The methods can include, during growth of the test plant over the growth period, adjusting a temperature within the enclosed chamber of the plant culture system by selectively activating at least one of a heating element and a cooling element of the system according to one or more temperature reference values for the test plant.

The methods can include, during growth of the test plant over the growth period, activating one or more light sources of the plant culture system to deliver light to the test plant according to a illumination reference information for the test plant.

At least one of the test plant and the support medium can include at least one nitrogen-fixing bacterium. The methods can include inoculating the test plant or a seed precursor of the test plant with the at least one nitrogen-fixing bacterium prior to positioning the test plant within the enclosed chamber of the plant culture system. The methods can include inoculating the test plant with the at least one nitrogen-fixing bacterium after positioning the test plant within the enclosed chamber of the plant culture system.

The methods can include determining a relative measurement of nitrogen fixation by the at least one nitrogen-fixing bacterium. Determining the relative measurement of nitrogen fixation can includes: activating an acetylene gas source to deliver a quantity of acetylene to a portion of the support medium; after an exposure interval, measuring an amount of ethylene generated by the at least one nitrogen-fixing bacterium from the quantity of acetylene; and determining a rate of acetylene reduction by the at least one nitrogen-fixing bacterium based on the amount of ethylene generated.

Embodiments of the methods can also include any of the other features described herein, including any combinations of features described in connection with different embodiments, except as expressly stated otherwise.

In another aspect, the disclosure features methods of identifying a nitrogen-fixing bacterial strain, the methods including: inoculating a test plant or a seed of a test plant with a composition including at least one bacterium of a candidate bacterial strain; positioning the test plant in a support medium within an enclosed chamber of a plant culture system; positioning a reference plant in a support medium within the enclosed chamber; adjusting a composition of a nitrogen gas mixture within the chamber so that a ratio of at least two nitrogen isotopes is different from a naturally occurring atmospheric ratio of the isotopes; growing the test and reference plants over a growth period within the enclosed chamber; determining relative amounts of nitrogen isotopes in test and reference plant tissues; and identifying the candidate bacterial strain as a nitrogen-fixing bacterial strain or a non-nitrogen-fixing bacterial strain based on the relative amounts of at least one nitrogen isotope in the test and reference plant tissues.

Embodiments of the methods can include any one or more of the following features.

The reference plant and a seed of the reference plant are not inoculated with a bacterium of the candidate bacterial strain. Adjusting the composition of nitrogen gas can include activating a gas delivery apparatus of the plant culture system to deliver nitrogen gas including a ratio of the at least two nitrogen isotopes that differs from a naturally occurring ratio of the at least two isotopes in atmospheric nitrogen gas. The at least two nitrogen isotopes can include $^{15}N$ and $^{14}N$. The at least two nitrogen isotopes can include $^{13}N$ and $^{14}N$. The at least two nitrogen isotopes can include $^{15}N$, $^{14}N$ and $^{13}N$.

The delivered nitrogen gas can include at least 20 atom % $^{15}N$ (e.g., at least 50 atom % $^{15}N$, at least 90 atom % $^{15}N$). Following adjustment of the composition of the nitrogen gas mixture, the nitrogen gas mixture can include at least 0.1 atom % $^{15}N$ or $^{13}N$ (e.g., at least 0.3 atom % $^{15}N$ or $^{13}N$, at least 0.5 atom % $^{15}N$ or $^{13}N$).

The growth period can include at least 7 days.

The test and reference plant tissues can each include root tissue and/or newly emerged whorl tissue and/or top-collared leaf tissue.

The methods can include harvesting the test and reference plant tissues from the test and reference plants, drying the harvested test and reference plant tissues for a drying time, grinding the dried, harvested tissues to form respective test and reference powders, and analyzing the test and reference powers to determine the relative amounts of nitrogen isotopes in the test and reference plant tissues.

The methods can include, if a seed of the test plant is inoculated with the composition including the at least one bacterium of the candidate bacterial strain, depositing the seed in a support medium to induce germination of the seed to form the test plant. The methods can include, following formation of the test plant, withholding growth medium from the test plant for an initial period of at least 7 days following germination. The methods can include, following the initial period, delivering a growth medium to the test plant. The growth medium can include a modified Hoaglund's solution.

The methods can include positioning the test plant within the enclosed chamber of a plant culture system at a time at least 14 days following germination of the seed (e.g., at a time at least 21 days following germination of the seed).

The methods can include, during growth of the test and reference plants over the growth period, measuring a humidity within the enclosed chamber of the plant culture system, and activating at least one of a humidifier and a de-humidifier to adjust the humidity according to a humidity reference value for the test and reference plants. The methods can include, during growth of the test and reference plants over the growth period, measuring an oxygen concentration within the enclosed chamber of the plant culture system, and activating a gas removal apparatus of the plant culture system to adjust the oxygen concentration according to a reference value for the test and reference plants. The methods can include, during growth of the test and reference plants over the growth period, measuring a carbon dioxide concentration within the enclosed chamber of the plant culture system, and activating a carbon dioxide gas source to adjust the carbon dioxide concentration according to a reference value for the test and reference plants. The methods can include, during growth of the test and reference plants over the growth period, adjusting a temperature within the enclosed chamber of the plant culture system by selectively activating at least one of a heating element and a cooling element of the system according to one or more temperature reference values for the test and reference plants. The methods can include, during growth of the test and reference plants over the growth period, activating one or more light sources of the plant culture system to deliver light to the test and reference plants according to a illumination reference information for the test and reference plants.

The methods can include determining a relative measurement of nitrogen fixation by the at least one bacterium of the candidate strain. Determining the relative measurement of nitrogen fixation can includes activating an acetylene gas source to deliver a quantity of acetylene to a portion of the support medium in which the test plant is supported, after an exposure interval, measuring an amount of ethylene generated by the at least one bacterium from the quantity of acetylene, and determining a rate of acetylene reduction by the at least one bacterium based on the amount of ethylene generated.

Embodiments of the methods can also include any of the other features described herein, including any combinations of features described in connection with different embodiments, except as expressly stated otherwise.

In another aspect, the disclosure features genetically engineered bacteria having a modification in a gene regulating nitrogen fixation or assimilation, where the bacterium is capable of fixing atmospheric nitrogen substantially throughout the tissues of a plant.

Embodiments of the genetically engineered bacteria can include any one or more of the following features.

The modification can include a deletion of all or a portion of the coding sequence of the nifL gene. All or a portion of the nifL coding sequence can be replaced by the promoter of the cspE gene. The modification can include a deletion of a portion of the coding sequence of the glnE gene.

The deletion of the portion of the coding sequence of the glnE gene can result in a truncated GlnE protein lacking an adenylyl-removing (AR) domain. The modification can include a mutant ntrC gene, where the mutant ntrC gene encodes a NtrC protein having an alanine residue at position 54.

The bacteria can include a deletion of all or a portion of the coding sequence of the nifL gene, a deletion of portion of the coding sequence of the glnE gene, and a mutant ntrC gene, where the mutant ntrC gene encodes a NtrC protein comprising an alanine residue at position 54.

The bacteria can be capable of fixing atmospheric nitrogen in one or more of the roots, roots, stems, leaves, fruits, flowers, seeds, initial growth tissue, and top growth. The bacteria can be diazotrophs.

The bacteria can be *Klebsiella variicola, Kosakonia sacchari, Klebsiella pneumonia, Azotobacter vinelandii,* or *Rahnella aquatilis* bacteria. The bacteria can be designated 137-3890 (genotype glnE_KO2, ΔnifL::Prm1.2, NtrC_D54A), represented by 138-3890 bacteria deposited as ATCC Accession No. PTA-126479.

Embodiments of the genetically engineered bacteria can also include any of the other features described herein, in any combination as appropriate, except as expressly stated otherwise.

In another aspect, the disclosure features genetically engineered bacteria which provide sufficient fixed nitrogen to a plant for the fixed nitrogen to be detectable in multiple plant tissues, the genetically engineered bacteria having a modification in a gene regulating nitrogen fixation or assimilation, where the modification in the gene regulating nitrogen fixation or assimilation results in one or more of: constitutive expression of a nifA gene in nitrogen limiting and non-nitrogen limiting conditions, activity of nifA in non-nitrogen limiting conditions, decreased uridylyl-removing activity of GlnD, decreased adenylyl-removing activity of GlnE, and increased ammonium excretion.

In another aspect, the disclosure features genetically engineered bacteria which provide sufficient fixed nitrogen to a plant for the fixed nitrogen to be detectable in multiple plant tissues, the genetically engineered bacteria having a modification in a gene regulating nitrogen fixation or assimilation that results in constitutive expression of a nifA gene in nitrogen limiting and non-nitrogen limiting conditions and optionally where the genetically engineered bacterium further includes a modification in a gene regulating nitrogen fixation or assimilation that results in one or more of: activity of nifA in non-nitrogen limiting conditions, decreased uridylyl-removing activity of GlnD, decreased adenylyl-removing activity of GlnE, and increased ammonium excretion.

In another aspect, the disclosure features genetically engineered bacteria which provide sufficient fixed nitrogen to a plant for the fixed nitrogen to be detectable in multiple plant tissues, the genetically engineered bacteria having a modification in a gene regulating nitrogen fixation or assimilation that results in constitutive expression of a nifA gene in nitrogen limiting and non-nitrogen limiting conditions and where the genetically engineered bacteria further include a modification in a gene regulating nitrogen fixation or assimilation that results in one or more of: activity of nifA in non-nitrogen limiting conditions, decreased uridylyl-removing activity of GlnD, decreased adenylyl-removing activity of GlnE, and increased ammonium excretion.

In another aspect, the disclosure features genetically engineered bacteria which provide sufficient fixed nitrogen to a plant for the fixed nitrogen to be detectable in multiple plant tissues, the genetically engineered bacteria including a mutation in the coding sequence of the bacteria's ntrC gene, where the coding sequence of the ntrC gene with the mutation encodes a NtrC protein with a D54A amino acid substitution, and where the genetically engineered bacteria are genetically engineered diazotrophs.

In another aspect, the disclosure features genetically engineered bacteria which provide sufficient fixed nitrogen to a plant for the fixed nitrogen to be detectable in multiple plant tissues, the genetically engineered bacteria including a mutation in the coding sequence of the bacteria's ntrC gene, where the coding sequence of the ntrC gene having the mutation encodes a NtrC protein with a D54A amino acid substitution, and where the genetically engineered bacteria further includes at least one modification in a gene regulating nitrogen fixation or assimilation that results in one or more of constitutive expression of a nifA gene in nitrogen limiting and non-nitrogen limiting conditions, activity of nifA in non-nitrogen limiting conditions, decreased uridylyl-removing activity of GlnD, decreased adenylyl-removing activity of GlnE, and increased ammonium excretion.

Embodiments of any of the foregoing genetically engineered bacteria can include any one or more of the following features.

The mutation in the coding sequence of the ntrC can result in increased ammonium excretion. The modification in a gene regulating nitrogen fixation or assimilation that results in activity of nifA in non-nitrogen limiting conditions can include a deletion of all or a portion of the coding sequence of the bacterium's nifL gene. The deletion of all or a portion of the coding sequence of the nifL gene can result in the decreased expression of nifL.

All or a portion of the nifL coding sequence can be replaced by a promoter. The promoter can be a non-intergeneric promoter. The promoter can be a constitutive promoter. The promoter can be an infC gene promoter, an ompX gene promoter, or a cspE gene promoter.

The modification in a gene regulating nitrogen fixation or assimilation that results in the decreased adenylyl-removing activity of GlnE can include a deletion of a portion of the coding sequence of the glnE gene. The deletion of a portion of the coding sequence of the glnE gene can result in a truncated GlnE protein lacking an adenylyl-removing (AR) domain.

The modification in a gene regulating nitrogen fixation or assimilation that results in increased ammonium excretion can include a mutation in the coding sequence of the bacteria's ntrC gene. The coding sequence of the ntrC gene having the point mutation can encode a NtrC protein featuring a D54A amino acid substitution.

The modification in a gene regulating nitrogen fixation or assimilation that results in constitutive expression of the nifA gene in nitrogen limiting and non-nitrogen limiting conditions can include an insertion of the coding sequence of the nifA gene in the genome of the genetically engineered bacteria. The modification in a gene regulating nitrogen fixation or assimilation that results in constitutive expression of the nifA gene in nitrogen limiting and non-nitrogen limiting conditions can include an insertion of the coding sequence of the nifA gene and a constitutive promoter in the genome of the genetically engineered *Klebsiella varicola* bacteria.

The genetically engineered bacteria can be *Agrobacterium radiobacter, Bacillus acidocaldarius, Bacillus acido-*

*terrestris, Bacillus agri, Bacillus aizawai, Bacillus albolactis, Bacillus alcalophilus, Bacillus alvei, Bacillus aminoglucosidicus, Bacillus aminovorans, Bacillus amylolyticus* (also known as *Paenibacillus amylolyticus*) *Bacillus amyloliquefaciens, Bacillus aneurinolyticus, Bacillus atrophaeus, Bacillus azotoformans, Bacillus badius, Bacillus cereus* (synonyms: *Bacillus endorhythmos, Bacillus medusa*), *Bacillus chitinosporus, Bacillus circulans, Bacillus coagulans, Bacillus endoparasiticus Bacillus fastidiosus, Bacillus firmus, Bacillus kurstaki, Bacillus lacticola, Bacillus lactimorbus, Bacillus lactis, Bacillus laterosporus* (also known as *Brevibacillus laterosporus*), *Bacillus lautus, Bacillus lentimorbus, Bacillus lentus, Bacillus licheniformis, Bacillus maroccanus, Bacillus megaterium, Bacillus metiens, Bacillus mycoides, Bacillus natio, Bacillus nematocida, Bacillus nigrificans, Bacillus nigrum, Bacillus pantothenticus, Bacillus popillae, Bacillus psychrosaccharolyticus, Bacillus pumilus, Bacillus siamensis, Bacillus smithii, Bacillus sphaericus, Bacillus subtilis, Bacillus thuringiensis, Bacillus uniflagellatus, Bradyrhizobium japonicum, Brevibacillus brevis Brevibacillus laterosporus* (formerly *Bacillus laterosporus*), *Chromobacterium subtsugae, Delftia acidovorans, Lactobacillus acidophilus, Lysobacter antibioticus, Lysobacter enzymogenes, Paenibacillus alvei, Paenibacillus polymyxa, Paenibacillus popilliae* (formerly *Bacillus popilliae*), *Pantoea agglomerans, Pasteuria penetrans* (formerly *Bacillus penetrans*), *Pasteuria usgae, Pectobacterium carotovorum* (formerly *Erwinia carotovora*), *Pseudomonas aeruginosa, Pseudomonas aureofaciens, Pseudomonas cepacia* (formerly known as *Burkholderia cepacia*), *Pseudomonas chlororaphis, Pseudomonas fluorescens, Pseudomonas proradix, Pseudomonas putida, Pseudomonas syringae, Serratia entomophila, Serratia marcescens, Streptomyces colombiensis, Streptomyces galbus, Streptomyces goshikiensis, Streptomyces griseoviridis, Streptomyces lavendulae, Streptomyces pracinus, Streptomyces saraceticus, Streptomyces venezuelae, Xanthomonas campestris, Xenorhabdus luminescens, Xenorhabdus nematophila, Rhodococcus globerulus* AQ719 (NRRL, Accession No. B-21663), *Bacillus* sp. AQ175 (ATCC Accession No. 55608), *Bacillus* sp. AQ 177 (ATCC Accession No. 55609), *Bacillus* sp. AQ178 (ATCC Accession No. 53522), or *Streptomyces* sp. strain NRRL, Accession No. B-30145.

The genetically engineered bacteria can be *Kosakonia sacchari* bacteria or *Klebsiella variicola* bacteria.

The genetically engineered bacteria can include a deletion of all or a portion of the coding sequence of the nifL gene, a deletion of a portion of the coding sequence of the glnE gene, and a point mutation in the coding sequence of the ntrC gene.

The genetically engineered bacteria can be represented by 137-3890 bacteria deposited as ATCC Accession No. PTA-126749.

The multiple plant tissues can include multiple tissues selected from the group consisting of root, leaf, and whorl tissues.

Embodiments of any of the foregoing genetically engineered bacteria can also include any of the other features described herein, in any combination as appropriate, except as expressly stated otherwise.

In another aspect, the disclosure features compositions that include any of the genetically engineered bacteria described herein. The compositions can include any of the features described herein, in any combination as appropriate, except as expressly stated otherwise.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed.

No language in the specification should be construed as indicating any non-claimed element as essential to the practice of the disclosure.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "about" is used synonymously with the term "approximately." Illustratively, the use of the term "about" with regard to an amount indicates that values slightly outside the cited values, e.g., plus or minus 0.1% to 10%.

Microbes in and around food crops can influence the traits of those crops. Plant traits that may be influenced by microbes include: yield (e.g., grain production, biomass generation, fruit development, flower set); nutrition (e.g., nitrogen, phosphorus, potassium, iron, micronutrient acquisition); abiotic stress management (e.g., drought tolerance, salt tolerance, heat tolerance); and biotic stress management (e.g., pest, weeds, insects, fungi, and bacteria). Strategies for altering crop traits include: increasing key metabolite concentrations; changing temporal dynamics of microbe influence on key metabolites; linking microbial metabolite production/degradation to new environmental cues; reducing negative metabolites; and improving the balance of metabolites or underlying proteins.

As used herein, a "control sequence" refers to an operator, promoter, silencer, or terminator.

As used herein, "in planta" may refer to in the plant, on the plant, or intimately associated with the plant, depending upon context of usage (e.g. endophytic, epiphytic, or rhizospheric associations). The plant may comprise plant parts, tissue, leaves, roots, root hairs, rhizomes, stems, seed, ovules, pollen, flowers, fruit, etc.

In some embodiments, native or endogenous control sequences of genes of the present disclosure are replaced with one or more intrageneric control sequences.

As used herein, "introduced" refers to the introduction by means of modern biotechnology, and not a naturally occurring introduction.

In some embodiments, the bacteria of the present disclosure have been modified such that they are not naturally occurring bacteria.

Fertilizers and exogenous nitrogen of the present disclosure may comprise the following nitrogen-containing molecules: ammonium, nitrate, nitrite, ammonia, glutamine, etc. Nitrogen sources of the present disclosure may include anhydrous ammonia, ammonia sulfate, urea, diammonium phosphate, urea-form, monoammonium phosphate, ammonium nitrate, nitrogen solutions, calcium nitrate, potassium nitrate, sodium nitrate, etc.

As used herein, "exogenous nitrogen" refers to non-atmospheric nitrogen readily available in the soil, field, or growth medium that is present under non-nitrogen limiting conditions, including ammonia, ammonium, nitrate, nitrite, urea, uric acid, ammonium acids, etc.

In some embodiments, the nitrogen fixation and assimilation genetic regulatory network comprises polynucleotides encoding genes and non-coding sequences that direct, modulate, and/or regulate microbial nitrogen fixation and/or assimilation and can comprise polynucleotide sequences of the nif cluster (e.g., nifA, nifB, nifC, . . . nifZ), polynucleotides encoding nitrogen regulatory protein C, polynucleotides encoding nitrogen regulatory protein B, polynucleotide sequences of the gln cluster (e.g. glnA and glnD), draT, and ammonia transporters/permeases. In some cases, the Nif cluster may comprise NifB, NifH, NifD, NifK, NifE, NifN, NifX, hesa, and NifV. In some cases, the Nif cluster may comprise a subset of NifB, NifH, NifD, NifK, NifE, NifN, NifX, hesa, and NifV.

In some embodiments, the increase of nitrogen fixation and/or the production of 1% or more of the nitrogen in the plant are measured relative to control or reference plants, which have not been exposed to the bacteria of the present disclosure. All increases or decreases in bacteria are measured relative to control or reference bacteria. All increases or decreases in plants are measured relative to control or reference plants.

As used herein the term "plant" can include plant parts, tissue, leaves, roots, root hairs, rhizomes, stems, seeds, ovules, pollen, flowers, fruit, etc. Thus, when the disclosure discusses providing a plurality of corn plants to a particular locus, it is understood that this may entail planting a corn seed at a particular locus.

As used herein, when the disclosure discuses a particular microbial deposit by accession number, it is understood that the disclosure also contemplates a microbial strain having all of the identifying characteristics of said deposited microbe, and/or a mutant thereof.

The term "microbial consortia" or "microbial consortium" refers to a subset of a microbial community of individual microbial species, or strains of a species, which can be described as carrying out a common function, or can be described as participating in, or leading to, or correlating with, a recognizable parameter, such as a phenotypic trait of interest.

The term "microbial community" means a group of microbes comprising two or more species or strains. Unlike microbial consortia, a microbial community does not have to be carrying out a common function, or does not have to be participating in, or leading to, or correlating with, a recognizable parameter, such as a phenotypic trait of interest.

As used herein, "isolate," "isolated," "isolated microbe," and like terms, are intended to mean that the one or more microorganisms has been separated from at least one of the materials with which it is associated in a particular environment (for example soil, water, plant tissue, etc.). Thus, an "isolated microbe" does not exist in its naturally occurring environment; rather, it is through the various techniques described herein that the microbe has been removed from its natural setting and placed into a non-naturally occurring state of existence. Thus, the isolated strain or isolated microbe may exist as, for example, a biologically pure culture, or as spores (or other forms of the strain). In aspects, the isolated microbe may be in association with an acceptable carrier, which may be an agriculturally acceptable carrier.

In certain aspects of the disclosure, the isolated microbes exist as "isolated and biologically pure cultures." It will be appreciated by one of skill in the art, that an isolated and biologically pure culture of a particular microbe, denotes that said culture is substantially free of other living organisms and contains only the individual microbe in question. The culture can contain varying concentrations of said microbe. The present disclosure notes that isolated and biologically pure microbes often "necessarily differ from less pure or impure materials." See, e.g., In re *Bergstrom*, 427 F.2d 1394, (CCPA 1970) (discussing purified prostaglandins), see also, In re *Bergy*, 596 F.2d 952 (CCPA 1979) (discussing purified microbes), see also, *Parke-Davis & Co. v. H.K. Mulford & Co.*, 189 F. 95 (S.D.N.Y. 1911) (Learned Hand discussing purified adrenaline), aff'd in part, rev'd in part, 196 F. 496 (2d Cir. 1912), each of which are incorporated herein by reference. Furthermore, in some aspects, the disclosure provides for certain quantitative measures of the concentration, or purity limitations, that must be found within an isolated and biologically pure microbial culture. The presence of these purity values, in certain embodiments, is a further attribute that distinguishes the presently disclosed microbes from those microbes existing in a natural state. See, e.g., *Merck & Co. v. Olin Mathieson Chemical Corp.*, 253 F.2d 156 (4th Cir. 1958) (discussing purity limitations for vitamin B12 produced by microbes), incorporated herein by reference.

As used herein, "individual isolates" should be taken to mean a composition, or culture, comprising a predominance of a single genera, species, or strain, of microorganism, following separation from one or more other microorganisms.

As used herein the terms "microorganism" or "microbe" should be taken broadly. These terms, used interchangeably, include but are not limited to, the two prokaryotic domains, Bacteria and Archaea. The term may also encompass eukaryotic fungi and protists.

Microbes of the present disclosure may include spores and/or vegetative cells. In some embodiments, microbes of the present disclosure include microbes in a viable but non-culturable (VBNC) state. As used herein, "spore" or "spores" refer to structures produced by bacteria and fungi that are adapted for survival and dispersal. Spores are generally characterized as dormant structures; however, spores are capable of differentiation through the process of germination. Germination is the differentiation of spores into vegetative cells that are capable of metabolic activity, growth, and reproduction. The germination of a single spore results in a single fungal or bacterial vegetative cell. Fungal spores are units of asexual reproduction, and in some cases are necessary structures in fungal life cycles. Bacterial spores are structures for surviving conditions that may ordinarily be nonconducive to the survival or growth of vegetative cells.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The term "processor" should be interpreted broadly to encompass a general purpose processor, a central processing unit (CPU), a microprocessor, a digital signal processor (DSP), a controller, a microcontroller, a state machine and so forth. Under some circumstances, a "processor" may refer to an application specific integrated circuit (ASIC), a programmable logic device (PLD), a field programmable gate array (FPGA), etc. The term "processor" may refer to a combination of processing devices, e.g., a combination of a DSP and a microprocessor, a plurality of microprocessors, one or more microprocessors in conjunction with a DSP core or any other such configuration.

The term "memory" should be interpreted broadly to encompass any electronic component capable of storing electronic information. The term memory may refer to various types of processor-readable media such as random access memory (RAM), read-only memory (ROM), non-volatile random access memory (NVRAM), programmable read-only memory (PROM), erasable programmable read only memory (EPROM), electrically erasable PROM (EEPROM), flash memory, magnetic or optical data storage, registers, etc. Memory is said to be in electronic communication with a processor if the processor can read information from and/or write information to the memory. Memory that is integral to a processor is in electronic communication with the processor.

The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may comprise a single computer-readable statement or many computer-readable statements.

Some embodiments described herein relate to a computer storage product with a nontransitory computer-readable medium (also can be referred to as a non-transitory processor-readable medium) having instructions or computer code thereon for performing various computer-implemented operations. The computer-readable medium (or processor-readable medium) is nontransitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Introduction

Figure 1:
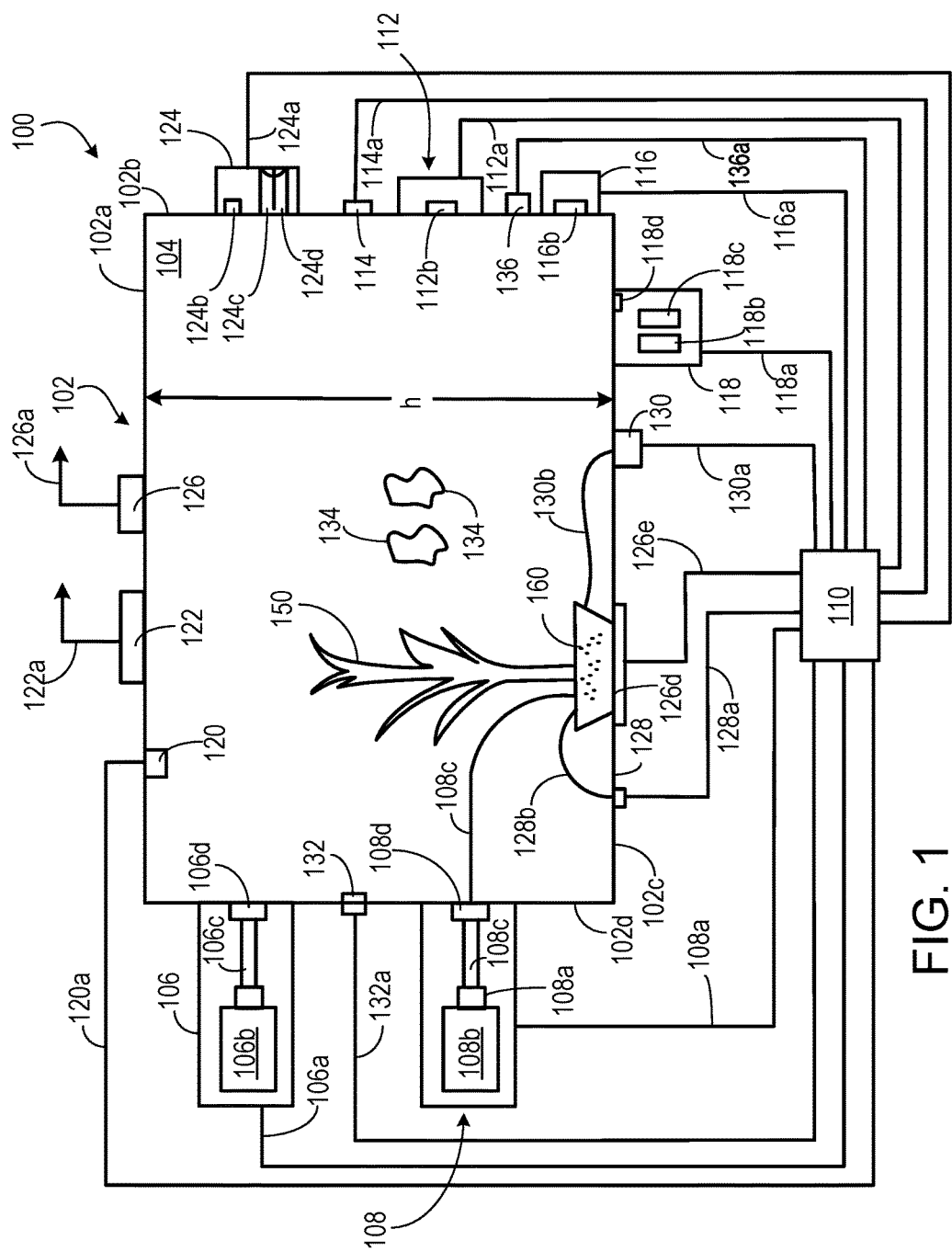
FIG. 1 is a schematic diagram of an example of a system for measuring nitrogen incorporation in plants.

Biological nitrogen fixation (BNF) is a process by which plant-associated microbes such as bacteria are believed to be able to provide nitrogen to host plants. Nitrogen is an important nutrient that influences plant growth. In particular, nitrogen is present in both amino acids and chlorophyll pigments, and a wide variety of biological processes, including plant-based protein synthesis and photosynthesis, therefore depend on the availability of nitrogen. When adequate soluble nitrogen is not available in a plant's growth medium, vegetative growth may be retarded and fruit production attenuated.

Typically, fixation of atmospheric nitrogen gas to yield soluble ammonia occurs via naturally occurring microbes such as bacteria. Nitrogenases present in the bacteria catalyze atmospheric nitrogen reduction. Significant research activity is currently directed to engineering improved microbes that enhance reductive conversion of atmospheric nitrogen to ammonia. An important aspect of this activity is measurement of nitrogen incorporation in plant tissues, and evaluation of engineered microbe strains for their nitrogen fixing activity.

Regulation of Nitrogen Fixation

In some cases, nitrogen fixation pathway may act as a target for genetic engineering and optimization. One trait that may be targeted for regulation is nitrogen fixation. Nitrogen fertilizer is the largest operational expense on a farm and the biggest driver of higher yields in row crops like corn and wheat. While some endophytes have the genetics necessary for fixing nitrogen in pure culture, the fundamental technical challenge is that wild-type endophytes of cereals and grasses stop fixing nitrogen in fertilized fields. The application of chemical fertilizers and residual nitrogen levels in field soils signal the microbe to shut down the biochemical pathway for nitrogen fixation.

Changes to the transcriptional and post-translational levels of components of the nitrogen fixation regulatory network may be beneficial to the development of a microbe capable of fixing and transferring nitrogen to corn in the presence of fertilizer.

In order to utilize elemental nitrogen (N) for chemical synthesis, life forms combine nitrogen gas ($N_2$) available in the atmosphere with hydrogen in a process known as nitrogen fixation. Because of the energy-intensive nature of biological nitrogen fixation, diazotrophs (bacteria and archaea that fix atmospheric nitrogen gas) have evolved sophisticated and tight regulation of the nif gene cluster in response to environmental oxygen and available nitrogen. Nif genes encode enzymes involved in nitrogen fixation (such as the nitrogenase complex) and proteins that regulate nitrogen fixation. Shamseldin (2013. Global J. Biotechnol. Biochem. 8(4):84-94) discloses detailed descriptions of nif genes and their products, and is incorporated herein by reference. Described herein are methods of producing a plant with an improved trait comprising isolating bacteria from a first plant, introducing a genetic variation into a gene of the isolated bacteria to increase nitrogen fixation, exposing a second plant to the variant bacteria, isolating bacteria from the second plant having an improved trait relative to the first plant, and repeating the steps with bacteria isolated from the second plant.

In Proteobacteria, regulation of nitrogen fixation centers around the σ54-dependent enhancer-binding protein NifA, the positive transcriptional regulator of the nif cluster. Intracellular levels of active NifA are controlled by two key factors: transcription of the nifLA operon, and inhibition of NifA activity by protein-protein interaction with NifL. Both of these processes are responsive to intracellular glutamine levels via the PII protein signaling cascade. This cascade is mediated by GlnD, which directly senses glutamine and catalyzes the uridylylation or deuridylylation of two PII regulatory proteins—GlnB and GlnK—in response the absence or presence, respectively, of bound glutamine. Under conditions of nitrogen excess, unmodified GlnB signals the deactivation of the nifLA promoter. However, under conditions of nitrogen limitation, GlnB is post-translationally modified, which inhibits its activity and leads to transcription of the nifLA operon. In this way, nifLA transcription is tightly controlled in response to environmental nitrogen via the PII protein signaling cascade. On the post-translational level of NifA regulation, GlnK inhibits the NifL/NifA interaction in a matter dependent on the overall level of free GlnK within the cell.

NifA is transcribed from the nifLA operon, whose promoter is activated by phosphorylated NtrC, another σ54-dependent regulator. The phosphorylation state of NtrC is mediated by the histidine kinase NtrB, which interacts with deuridylylated GlnB but not uridylylated GlnB. Under conditions of nitrogen excess, a high intracellular level of glutamine leads to deuridylylation of GlnB, which then interacts with NtrB to deactivate its phosphorylation activity and activate its phosphatase activity, resulting in dephosphorylation of NtrC and the deactivation of the nifLA promoter. However, under conditions of nitrogen limitation, a low level of intracellular glutamine results in uridylylation of GlnB, which inhibits its interaction with NtrB and allows the phosphorylation of NtrC and transcription of the nifLA operon. In this way, nifLA expression is tightly controlled in response to environmental nitrogen via the PII protein signaling cascade. nifA, ntrB, ntrC, and glnB, are all genes that can be mutated in the methods described herein. These processes may also be responsive to intracellular or extracellular levels of ammonia, urea or nitrates.

The activity of NifA is also regulated post-translationally in response to environmental nitrogen, most typically through NifL-mediated inhibition of NifA activity. In general, the interaction of NifL and NifA is influenced by the PII protein signaling cascade via GlnK, although the nature of the interactions between GlnK and NifL/NifA varies significantly between diazotrophs. In *Klebsiella pneumoniae*, both forms of GlnK inhibit the NifL/NifA interaction, and the interaction between GlnK and NifL/NifA is determined by the overall level of free GlnK within the cell. Under nitrogen-excess conditions, deuridylylated GlnK interacts with the ammonium transporter AmtB, which serves to both block ammonium uptake by AmtB and sequester GlnK to the membrane, allowing inhibition of NifA by NifL. On the other hand, in *Azotobacter vinelandii*, interaction with deuridylylated GlnK is required for the NifL/NifA interaction and NifA inhibition, while uridylylation of GlnK inhibits its interaction with NifL. In diazotrophs lacking the nifL gene, there is evidence that NifA activity is inhibited directly by interaction with the deuridylylated forms of both GlnK and GlnB under nitrogen-excess conditions. In some bacteria the Nif cluster may be regulated by glnR, and further in some cases this may comprise negative regulation.

Regardless of the mechanism, post-translational inhibition of NifA is an important regulator of the nif cluster in most known diazotrophs. Additionally, nifL, amtB, glnK, and glnR are genes that can be mutated in the methods described herein.

In addition to regulating the transcription of the nif gene cluster, many diazotrophs have evolved a mechanism for the direct post-translational modification and inhibition of the nitrogenase enzyme itself, known as nitrogenase shutoff. This is mediated by ADP-ribosylation of the Fe protein (NifH) under nitrogen-excess conditions, which disrupts its interaction with the MoFe protein complex (NifDK) and abolishes nitrogenase activity. DraT catalyzes the ADPribosylation of the Fe protein and shutoff of nitrogenase, while DraG catalyzes the removal of ADP-ribose and reactivation of nitrogenase. As with nifLA transcription and NifA inhibition, nitrogenase shutoff is also regulated via the PII protein signaling cascade. Under nitrogen-excess conditions, deuridylylated GlnB interacts with and activates DraT, while deuridylylated GlnK interacts with both DraG and AmtB to form a complex, sequestering DraG to the membrane. Under nitrogen-limiting conditions, the uridylylated forms of GlnB and GlnK do not interact with DraT and DraG, respectively, leading to the inactivation of DraT and the diffusion of DraG to the Fe protein, where it removes the ADP-ribose and activates nitrogenase. The methods described herein also contemplate introducing genetic variation into the nifH, nifD, nifK, and draT genes.

Although some endophytes have the ability to fix nitrogen in vitro, often the genetics are silenced in the field by high levels of exogenous chemical fertilizers. One can decouple the sensing of exogenous nitrogen from expression of the nitrogenase enzyme to facilitate field-based nitrogen fixation. Improving the integral of nitrogenase activity across time further serves to augment the production of nitrogen for utilization by the crop. Specific targets for genetic variation to facilitate field-based nitrogen fixation using the methods described herein include one or more genes selected from the group consisting of nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ.

An additional target for genetic variation to facilitate field-based nitrogen fixation using the methods described herein is the NifA protein. The NifA protein is typically the activator for expression of nitrogen fixation genes. Increasing the production of NifA (either constitutively or during high ammonia condition) circumvents the native ammonia-sensing pathway. In addition, reducing the production of NifL proteins, a known inhibitor of NifA, also leads to an increased level of freely active NifA. In addition, increasing the transcription level of the nifAL operon (either constitutively or during high ammonia condition) also leads to an overall higher level of NifA proteins. Elevated level of nifAL expression is achieved by altering the promoter itself or by reducing the expression of NtrB (part of ntrB and ntrC signaling cascade that originally would result in the shutoff of nifAL operon during high nitrogen condition). High level of NifA achieved by these or any other methods described herein increases the nitrogen fixation activity of the endophytes.

Another target for genetic variation to facilitate field-based nitrogen fixation using the methods described herein is the GlnD/GlnB/GlnK PII signaling cascade. The intracellular glutamine level is sensed through the GlnD/GlnB/GlnK PII signaling cascade. Active site mutations in GlnD that abolish the uridylyl-removing activity of GlnD disrupt the nitrogen-sensing cascade. In addition, reduction of the GlnB concentration short circuits the glutamine-sensing cascade. These mutations "trick" the cells into perceiving a nitrogen-limited state, thereby increasing the nitrogen fixation level activity. These processes may also be responsive to intracellular or extracellular levels of ammonia, urea or nitrates.

The amtB protein is also a target for genetic variation to facilitate field-based nitrogen fixation using the methods described herein. Ammonia uptake from the environment can be reduced by decreasing the expression level of amtB protein. Without intracellular ammonia, the endophyte is not able to sense the high level of ammonia, preventing the down-regulation of nitrogen fixation genes. Any ammonia that manages to get into the intracellular compartment is converted into glutamine. Intracellular glutamine level is the major currency of nitrogen sensing. Decreasing the intracellular glutamine level prevents the cells from sensing high ammonium levels in the environment. This effect can be achieved by increasing the expression level of glutaminase, an enzyme that converts glutamine into glutamate. In addition, intracellular glutamine can also be reduced by decreasing glutamine synthase (an enzyme that converts ammonia into glutamine). In diazotrophs, fixed ammonia is quickly assimilated into glutamine and glutamate to be used for cellular processes. Disruptions to ammonia assimilation may enable diversion of fixed nitrogen to be exported from the cell as ammonia. The fixed ammonia is predominantly assimilated into glutamine by glutamine synthetase (GS), encoded by glnA, and subsequently into glutamine by glutamine oxoglutarate aminotransferase (GOGAT). In some examples, glnS encodes a glutamine synthetase. GS is regulated post-translationally by GS adenylyl transferase (GlnE), a bi-functional enzyme encoded by glnE that catalyzes both the adenylylation and de-adenylylation of GS through activity of its adenylyl-transferase (AT) and adenylyl-removing (AR) domains, respectively. Under nitrogen limiting conditions, glnA is expressed, and GlnE's AR domain de-adynylylates GS, allowing it to be active. Under conditions of nitrogen excess, glnA expression is turned off, and GlnE's AT domain is activated allosterically by glutamine, causing the adenylylation and deactivation of GS.

Furthermore, the draT gene may also be a target for genetic variation to facilitate field-based nitrogen fixation using the methods described herein. Once nitrogen fixing enzymes are produced by the cell, nitrogenase shut-off represents another level in which cell downregulates fixation activity in high nitrogen condition. This shut-off could be removed by decreasing the expression level of DraT.

Methods for imparting new microbial phenotypes can be performed at the transcriptional, translational, and post-translational levels. The transcriptional level includes changes at the promoter (such as changing sigma factor affinity or binding sites for transcription factors, including deletion of all or a portion of the promoter) or changing transcription terminators and attenuators. The translational level includes changes at the ribosome binding sites and changing mRNA degradation signals. The post-translational level includes mutating an enzyme's active site and changing protein-protein interactions. These changes can be achieved in a multitude of ways. Reduction of expression level (or complete abolishment) can be achieved by swapping the native ribosome binding site (RBS) or promoter with another with lower strength/efficiency. ATG start sites can be swapped to a GTG, TTG, or CTG start codon, which results in reduction in translational activity of the coding region. Complete abolishment of expression can be done by knocking out (deleting) the coding region of a gene. Frame-shifting the open reading frame (ORF) likely will result in a premature stop codon along the ORF, thereby creating a non-functional truncated product. Insertion of in-frame stop codons will also similarly create a non-functional truncated product. Addition of a degradation tag at the N or C terminal can also be done to reduce the effective concentration of a particular gene.

Conversely, expression level of the genes described herein can be achieved by using a stronger promoter. To ensure high promoter activity during high nitrogen level condition (or any other condition), a transcription profile of the whole genome in a high nitrogen level condition could be obtained and active promoters with a desired transcription level can be chosen from that dataset to replace the weak promoter. Weak start codons can be swapped out with an ATG start codon for better translation initiation efficiency. Weak ribosomal binding sites (RBS) can also be swapped out with a different RBS with higher translation initiation efficiency. In addition, site-specific mutagenesis can also be performed to alter the activity of an enzyme.

Increasing the level of nitrogen fixation that occurs in a plant can lead to a reduction in the amount of chemical fertilizer needed for crop production and reduce greenhouse gas emissions (e.g., nitrous oxide).

Measurement of Nitrogen Incorporation

Most studies to date have relied on proxy or short term measurements to determine whether fixed nitrogen produced by plant-associated microbes is incorporated by plant tissues. Such techniques include, for example, $^{15}N$ dilution measurements in which $^{15}N$ depletion in nitrogen gas is measured and is adopted as a representation of nitrogen-reducing activity of particular microbes. These techniques also include acetylene reduction measurements, in which the rate of acetylene reduction to ethylene by particular microbes is adopted as a representation of the microbes' nitrogenase activity.

The present disclosure features systems and methods for measuring nitrogen incorporation by plant tissues. When the parent plants are inoculated with naturally-occurring or engineered nitrogen-fixing microbes, measurements of nitrogen incorporation can be used directly assess the nitrogen fixing activity of the microbes. In particular, the systems and methods described can adjust ratios of different nitrogen isotopes in the nitrogen gas environment of the plants, so that nitrogen present in plant tissues following a growth cycle can be attributed more directly to microbe-mediated nitrogen fixation. Further, the systems and methods can be used to investigate the provision of fixed nitrogen to different plant tissues, and can provide periodic measurements of nitrogen incorporation at different stages of a growth cycle.

Plant Growth and Measurement Systems

FIG. 1 shows an example of a system 100 for plant growth and measurement. System 100 includes a chamber 102 with walls 102a-102d that enclose a spatial volume 104 internal to chamber 102. System 100 also includes a gas delivery apparatus 106 and a nutrient delivery apparatus 108 connected to a controller 110 via control lines 106a and 108a, respectively. System 100 can optionally include a sampling apparatus 112.

Chamber 102 can include any number of walls suitable for enclosing spatial volume 104, and the wall(a)s can define any shape for chamber 102. In some embodiments, for example, the wall(s) define a cubic or rectangular prismatic shape for chamber 102. In certain embodiments, the wall(s) define a spherical or elliptical shape for chamber 102. More generally, the wall(s) can define any regular or irregular shape for chamber 102.

As shown in FIG. 1, at least one surface of at least one wall typically supports one or more plants 150 within the enclosed spatial volume 104. The height h of chamber 102 is the minimum distance between the plant-supporting surface (102c in FIG. 1) and a wall surface opposite the plant supporting surface. Upward plant growth generally occurs in a direction parallel to height h, and so the height can be selected to accommodate such growth for one or more different plant types. In some embodiments, h can be 0.5 m or more (e.g., 0.6 m or more, 0.7 m or more, 0.8 m or more, 0.9 m or more, 1.0 m or more, 1.5 m or more, 2.0 m or more, 2.5 m or more, 3.0 m or more, 3.5 m or more, 4.0 m or more, 4.5 m or more, 5.0 m or more, 5.5 m or more, 6.0 m or more, 6.5 m or more, 7.0 m or more, 7.5 m or more, 8.0 m or more, 8.5 m or more, 9.0 m or more, 9.5 m or more, 10.0 m or more, or even more).

In certain embodiments, as shown in FIG. 1, the height h is sufficiently large so that the entire plant 150 is positioned within the enclosed spatial volume 104. This provides an important advantage relative to measurement systems in which just the plant roots are enclosed. By placing the entire plant within the enclosed spatial volume, direct assessment of the fixation of nitrogen surrounding the entire plant—as is typical under field growing conditions—and subsequent incorporation of reduced nitrogen by plant tissues can be performed.

In general, the enclosed spatial volume 104 of chamber 102 can be selected as desired to accommodate one or more plants and gases delivered to the plants. In some embodiments, for example, the enclosed spatial volume can be 100 L or more (e.g., 200 L or more, 300 L or more, 400 L or more, 500 L or more, 600 L or more, 700 L or more, 800 L or more, 900 L or more, 1000 L or more, 1500 L or more, 2000 L or more, 2500 L or more, 3000 L or more, 4000 L or more, 5000 L or more, 7000 L or more, 10,000 L or more, 15,000 L or more, 20,000 L or more, 30,000 L or more, 50,000 L or more, or even more).

In some embodiments, chamber 102 is relatively airtight, such that a leakage rate of gases from chamber 102 is relatively small. For example, when chamber 102 is filled with a gas such as nitrogen at a pressure of 1.5 atmospheres (e.g., 152 kPa), a leakage rate of the gas from the chamber can be less than 0.5 L/day (e.g., less than 0.3 L/day, less than 0.1 L/day, less than 0.05 L/day, less than 0.01 L/day, less than 0.005 L/day, less than 0.001 L/day). More generally, when chamber 102 is filled with a gas such as nitrogen at a pressure p at a first time, the gas pressure within the chamber at a second time at least 7 days after the first time can be 0.70p or more (e.g., 0.80p or more, 0.85p or more, 0.90p or more, 0.95p or more, 0.98p or more, 0.99p or more, 0.999p or more, 0.9999p or more, or even more).

The walls of chamber 102 can generally be formed from a variety of materials including, but not limited to, various plastics and metals. Mating walls can be joined by bonding, welding, clamping, and other processes to form wall joints. A variety of structural supporting members can be used to reinforce the walls of chamber 102, and such members can be formed of the same or different materials than the walls.

During operation of system 100, controller 110 activates the gas delivery apparatus 106 to deliver one or more gases into the enclosed spatial volume 104 of chamber 102. Gas delivery apparatus 106 can be implemented in different ways. In some embodiments, gas delivery apparatus 106 is positioned within chamber 102. Alternatively, in certain embodiments, gas delivery apparatus 106 (or a portion thereof) is positioned external to chamber 102. Gas delivery apparatus 106 can include one or more gas sources 106b, one or more conduits 106c, and one or more valves 106d. As shown in FIG. 1, each of the valves 106d can optionally be connected to controller 110, which activates the valve(s) 106d to regulate gas delivery from the gas delivery apparatus 106.

Figure 2:
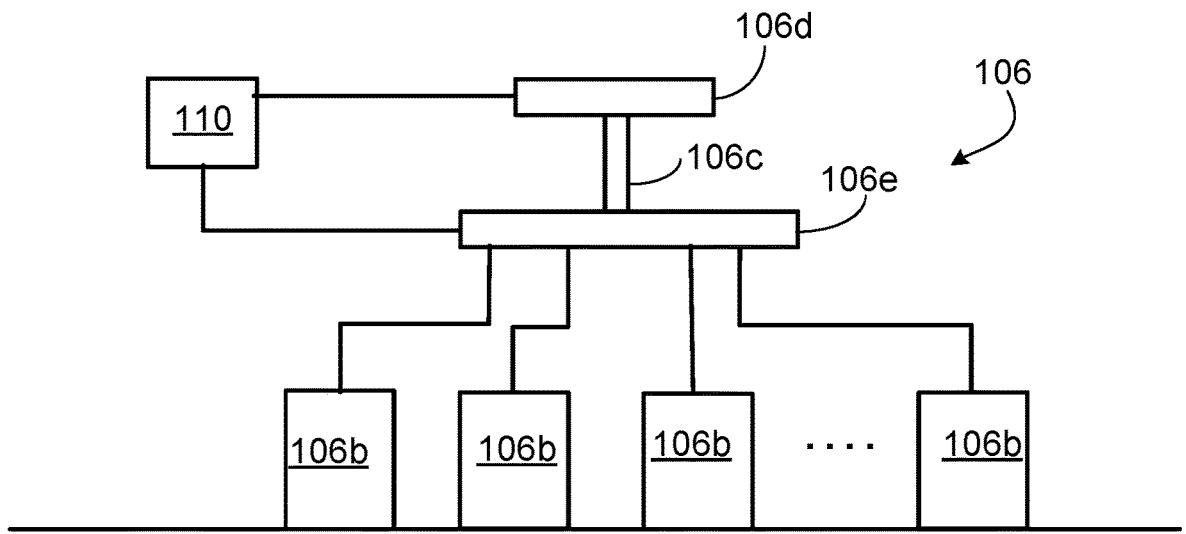
FIG. 2 is a schematic diagram of an example of a gas delivery apparatus.

FIG. 2 shows an example of a gas delivery apparatus 106 that includes multiple gas sources 106b. Conduits connect each of the gas sources 106b to a manifold 106e, which is connected to controller 110. The output port of manifold 106e is connected to valve 106d via conduit 106c, and valve 106d is connected to controller 110. Controller 110 can selectively deliver gases from any of the gas sources 106b into chamber 102 by activating manifold 106e to connect a selected gas source 106b to conduit 106c, and then activating valve 106d.

In general, gas delivery apparatus 106 can include any number of gas sources 106b (e.g., one or more gas sources, two or more gas sources, three or more gas sources, four or more gas sources, five or more gas sources, six or more gas sources, seven or more gas sources, eight or more gas sources, nine or more gas sources, ten or more gas sources, or even more gas sources).

In some embodiments, gas delivery apparatus 106 includes one or more sources of nitrogen gas. In certain embodiments, at least one nitrogen gas source delivers nitrogen gas for which a ratio of isotopes corresponds approximately to atmospheric nitrogen gas, to with 5% of the ideal value of the isotopic ratio for atmospheric nitrogen gas. In general, the nitrogen isotopes $^{15}N$ and $^{14}N$ are present in atmospheric nitrogen gas at relative percentages of 0.366% and 99.634%, and so the isotopic ratio $^{15}N/^{14}N$ for atmospheric nitrogen gas is 0.00367.

In some embodiments, at least one nitrogen gas source delivers nitrogen gas that is enriched in $^{15}N$ relative to $^{14}N$, such that the $^{15}N/^{14}N$ ratio for the nitrogen gas is greater than the $^{15}N/^{14}N$ ratio for atmospheric nitrogen gas. In some embodiments, for example, the $^{15}N/^{14}N$ ratio in the nitrogen gas can be 0.005 or more (e.g., 0.007 or more, 0.01 or more, 0.05 or more, 0.1 or more, 0.5 or more, 1.0 or more, 2.0 or more, 3.0 or more, 4.0 or more, 5.0 or more, 7.0 or more, 10.0 or more, 15.0 or more, 20.0 or more, 25.0 or more, 30.0 or more, 35.0 or more, 40.0 or more, 45.0 or more, 50.0 or more, or even more).

In certain embodiments, at least one nitrogen gas source delivers nitrogen gas that is enriched in $^{15}N$ relative to $^{14}N$, such that such that the abundance of $^{15}N$ in the nitrogen gas is at least 30 atom % or more (e.g., at least 40 atom % or more, at least 50 atom % or more, at least 60 atom % or more, at least 70 atom % or more, at least 80 atom % or more, at least 90 atom % or more, at least 95 atom % or more, at least 98 atom % or more, at least 99 atom % or more, at least 99.5 atom % or more, at least 99.9 atom % or more, at least 99.99 atom % or more).

In some embodiments, controller 110 can adjust an isotopic ratio of $^{15}N$ to $^{14}N$ in chamber 102 by activating the gas delivery apparatus 106 to deliver a mixture of nitrogen gases into chamber 102. The mixture can include, for example, atmospheric nitrogen gas and one or more nitrogen gases enriched in $^{15}N$ relative to $^{14}N$. Following delivery of the nitrogen gases into chamber 102, an abundance of $^{15}N$ in the gas mixture can be 0.05 atom % or more (e.g., 0.1 atom % or more, 0.2 atom % or more, 0.3 atom % or more, 0.5 atom % or more, 0.7 atom % or more, 1.0 atom % or more, 2.0 atom % or more, 3.0 atom % or more, 5.0 atom % or more, 7.0 atom % or more, 10.0 atom % or more, or even more).

In general, the nitrogen isotope $^{13}N$ is not present in atmospheric nitrogen gas, as it is unstable. Accordingly, the isotopic ratio $^{13}N/^{14}N$ for atmospheric nitrogen gas is 0. In some embodiments, at least one nitrogen gas source delivers nitrogen gas that is enriched in $^{13}N$ relative to $^{14}N$, such that the $^{13}N/^{14}N$ ratio for the nitrogen gas is greater than the $^{13}N/^{14}N$ ratio for atmospheric nitrogen gas (i.e., greater than zero). In some embodiments, for example, the $^{13}N/^{14}N$ ratio in the nitrogen gas can be 0.005 or more (e.g., 0.007 or more, 0.01 or more, 0.05 or more, 0.1 or more, 0.5 or more, 1.0 or more, 2.0 or more, 3.0 or more, 4.0 or more, 5.0 or more, 7.0 or more, 10.0 or more, 15.0 or more, 20.0 or more, 25.0 or more, 30.0 or more, 35.0 or more, 40.0 or more, 45.0 or more, 50.0 or more, or even more).

In certain embodiments, at least one nitrogen gas source delivers nitrogen gas that is enriched in $^{13}N$ relative to $^{14}N$, such that such that the abundance of $^{15}N$ in the nitrogen gas is at least 5 atom % or more (e.g., at least 10 atom % or more, at least 15 atom % or more, at least 20 atom % or more, at least 30 atom % or more, at least 40 atom % or more, at least 50 atom % or more, at least 60 atom % or more, at least 70 atom % or more, at least 80 atom % or more, at least 90 atom % or more, or even more).

In some embodiments, controller 110 can adjust an isotopic ratio of $^{13}N$ to $^{14}N$ in chamber 102 by activating the gas delivery apparatus 106 to deliver a mixture of nitrogen gases into chamber 102. The mixture can include, for example, atmospheric nitrogen gas and one or more nitrogen gases enriched in $^{13}N$ relative to $^{14}N$. Following delivery of the nitrogen gases into chamber 102, an abundance of $^{13}N$ in the gas mixture can be 0.05 atom % or more (e.g., 0.1 atom % or more, 0.2 atom % or more, 0.3 atom % or more, 0.5 atom % or more, 0.7 atom % or more, 1.0 atom % or more, 2.0 atom % or more, 3.0 atom % or more, 5.0 atom % or more, 7.0 atom % or more, 10.0 atom % or more, or even more).

In some embodiments, gas delivery apparatus 106 includes one or more sources of carbon dioxide gas. As carbon dioxide is an essential nutrient for plant growth, controller 110 can be configured to deliver carbon dioxide to the enclosed spatial volume 104 of chamber 102 by activating valve 106d. For a gas delivery apparatus 106 configured as shown in FIG. 2, controller 110 can also adjust manifold 106e so that a carbon dioxide gas source 106b is in fluid communication with conduit 106c through manifold 106e.

Returning to FIG. 1, during operation of system 100, controller 110 activates nutrient delivery apparatus 108 to deliver an aqueous growth medium to plant 150. In general, the nature, amount, and timing of delivery of the growth medium is part of reference information (e.g., a set of growth conditions) for plant 150. Controller 110 obtains the growth information (e.g., from a storage unit containing the information, or from direct entry of the information by a user of system 100) and adjusts the volume and delivery times of the growth medium by selective activation of nutrient delivery apparatus 108. If nutrient delivery apparatus 108 includes multiple reservoirs containing different growth media, controller 110 selectively delivers the proper growth medium from one or more corresponding reservoirs as well. In this manner, controller 110 is capable of implementing a complex program of delivery of the growth medium to plant 150.

In some embodiments, nutrient delivery apparatus 108 can be positioned within the enclosed spatial volume 104 of chamber 102. Alternatively, in certain embodiments, nutrient delivery apparatus 108 (or a portion thereof) is positioned external to chamber 102 and connected to a port formed in the one or more walls of chamber 102.

Nutrient delivery apparatus can include a variety of components. In some embodiments, for example, nutrient delivery apparatus includes one or more reservoirs 108b configured to store an aqueous growth medium. Nutrient delivery apparatus 108 can optionally include one or more conduits 108c for delivering the growth medium to plant 150 (e.g., to a soil 160 in which the roots of plant 150 are positioned). In certain embodiments, nutrient delivery apparatus 108 includes one or more valves 108d connected to controller 110. To regulate delivery of the growth medium from reservoir 108b to plant 150, controller 110 opens valve 108d, allowing the growth medium to flow from reservoir 108b through conduit(s) 108c.

In some embodiments, to facilitate flow of the growth medium, nutrient delivery apparatus 108 can include a flow mechanism 108e. Flow mechanism 108e can optionally be connected to controller 110, and controller 110 can activate flow mechanism 108e to deliver growth medium from reservoir 108b through conduit(s) 108c to plant 150. Flow mechanism 108e can be implemented in a variety of ways. In some embodiments, for example, flow mechanism 108e can include one or more of a wide variety of different types of pumps. In certain embodiments, flow mechanism 108e can include a pressure reducing device or apparatus, such as a reduced-pressure source (e.g., a vacuum source).

In general, nutrient delivery apparatus 108 can be configured to deliver a variety of different aqueous growth media. Examples of such media include, but are not limited to, modified Hoaglund's solutions at varying concentrations.

In some embodiments, one or more reservoirs in nutrient delivery apparatus 108 are configured to contain one or more additional nutrient media, and controller 110 can be configured to deliver to the one or more additional nutrient media to plant 150 in the same manner described above for the growth medium. Delivery of the nutrient media can also be performed by controller 110 according to reference information (e.g., a set of growth conditions) for plant 150.

In some embodiments, system 100 includes a gas detector 114 connected to controller 110 via a control line 114a. In general, gas detector 114 is configured to generate a measurement signal in response to the presence of one or more different gas species within chamber 102. Gas detector 114 can be configured to detect a single type of gas, multiple types of gases, and one or more different properties of the gas(es).

In certain embodiments, for example, gas detector 114 includes a detector configured to generate a measurement signal representing a ratio of abundances of different isotopes of nitrogen in chamber 102. For example, gas detector 114 can be configured to measure the abundances of one or more of $^{15}N$, $^{14}N$, and $^{13}N$ in chamber 102. Gas detector 114 can optionally be configured to generate measurement signals representing the measured abundances and/or measurement signals representing isotopic ratios of the abundances of nitrogen isotopes including, but not limited to, signals representing the isotopic ratios $^{15}N/^{14}N$ and/or $^{13}N/^{14}N$.

Controller 110 can be configured to regulate delivery of one or more gases (e.g., nitrogen gas(es)) into chamber 102 based on the measurement signals generated by gas detector 114. For example, if the measured $^{15}N/^{14}N$ ratio is too low relative to a reference value for this ratio, controller 110 activates gas delivery apparatus 106 to deliver one or more nitrogen gases that are enriched in $^{15}N$ relative to $^{14}N$, as discussed above. As another example, if the measured $^{13}N/^{14}N$ ratio is too low relative to a reference value for this ratio, controller 110 activates gas delivery apparatus 106 to deliver one or more nitrogen gases that are enriched in $^{13}N$ relative to $^{14}N$, as discussed above. If either of the measured values of these ratios are too larger relative to reference values for the ratios, controller 110 activates gas delivery apparatus 106 to deliver nitrogen gas that is relatively depleted in $^{15}N$ and/or $^{13}N$ (e.g., nitrogen gas with atmospheric relative isotope abundances).

Figure 3:
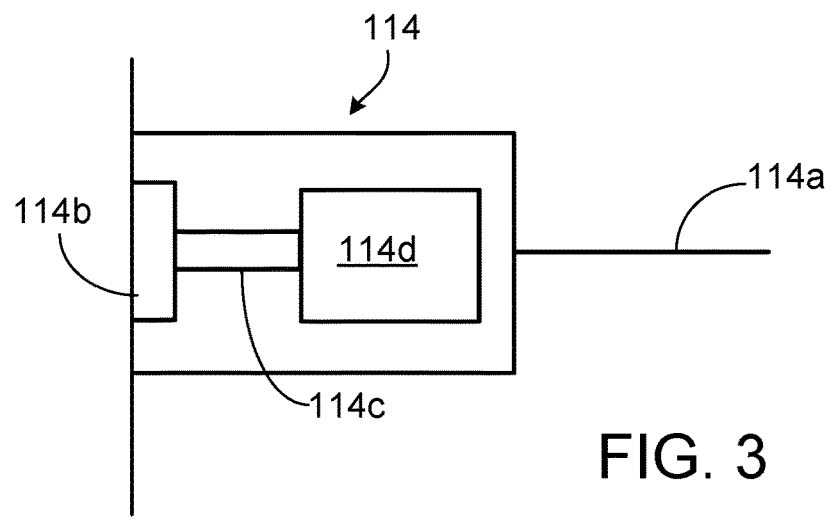
FIG. 3 is a schematic diagram of an example of a gas detector.

FIG. 3 shows an example of a gas detector 114. Gas detector 114 in FIG. 3 is implemented as a mass spectrometry apparatus, and includes a valve 114b, a conduit 114c, and a mass analyzer 114d. To analyze gases from chamber 102, controller 110 opens valve 114b, admitting gas from chamber 102 into conduit 114c. The admitted gas propagates through conduit 114c and enters mass analyzer 114d, where it is ionized and relative abundances of various components (e.g., atomic ions) are measured. Measurement signals comprising abundance and/or isotopic ratio information can be transmitted to controller 110 via control line 114a.

A wide variety of different mass analyzers 114d can be used in gas detector 114. Examples of such analyzers include, but are not limited to, isotope ratio mass spectrometry analyzers, as described for example in Rodrigues et al., Comprehensive Analytical Chemistry 60: 77-99 (2013), the entire contents of which are incorporated by reference herein.

In some embodiments, gas detector 114 can be implemented as an isotope ratio infrared spectrometry detector. Isotope ratio infrared spectrometry detectors typically include a light source (e.g., an infrared laser source) and a detector configured to measure absorption of the light generated by the source by a sample (e.g., a gas sample from chamber 102). Isotope ratio infrared spectrometry detectors are described for example in Hippler et al., "Mass and Isotope Selective Infrared Spectroscopy," *Handbook of High Resolution Spectroscopy*, Vol. 2, Chapter 28, pp. 1069-1118 (2011), the entire contents of which are incorporated herein by reference.

In some embodiments, gas detector 114 includes a detector configured to generate a measurement signal representing an amount or concentration of oxygen gas in chamber 102. Oxygen gas is produced as a by-product of the growth of plant 150 in chamber 102, and detection of oxygen gas can be important to ensure that suitable growth conditions are maintained during a growth cycle of plant 150.

Suitable detectors for oxygen include mass spectrometry detectors and infrared spectrometry detectors, as described above. A wide variety of additional detectors for oxygen can also be used, including potentiometric detectors, amperometric detectors, paramagnetic detectors, and spectroscopic detectors. Examples of such detectors are described in Shuk, "Oxygen Gas Sensising Technologies Application: A Comprehensive Review," *Sensors for Everyday Life*, pp. 81-107 (2016), the entire contents of which are incorporated herein by reference. Suitable oxygen detectors are available commercially from Honeywell Corp. (Charlotte, N.C.), for example.

In some embodiments, gas detector 114 includes a detector configured to generate a measurement signal representing an amount or concentration of carbon dioxide gas in chamber 102. Detection of carbon dioxide gas can be important to ensure that sufficient quantities of carbon dioxide are available to sustain the growth of plant 150. Typically, when the measured concentration of carbon dioxide in chamber 102 is less than a reference value for plant 150, controller 110 can activate gas delivery apparatus 106 to deliver additional carbon dioxide gas into chamber 102 to maintain a suitable growth environment for plant 150.

A variety of different carbon dioxide detectors can be used in gas detector 114. Examples of such detectors include, but are not limited to, infrared absorption detectors and chemical sensors. Various examples of suitable carbon dioxide detectors are described in Mills, "Optical Sensors for Carbon Dioxide and Their Applications," *Sensors for Environment, Health and Security*, pp. 347-370 (2009), the entire contents of which are incorporated herein by reference. Carbon dioxide sensors are available commercially from Mettler Toledo (Columbus, OH), for example.

In some embodiments, gas detector 114 includes a detector configured to generate a measurement signal representing an amount or concentration of nitrous oxide gas in chamber 102. Nitrous oxide generation can, in some circumstances, accompany nitrogen fixation by soil-based microbes, as described for example in Zhong et al., "Nitrous oxide emissions associated with nitrogen fixation by grain legumes," *Soil Biology and Biochemistry* 41(11): 2283-2291 (2009), the entire contents of which are incorporated herein by reference. Accordingly, measurements of nitrous oxide amounts or concentrations in chamber 102 can be used to determine whether microbes present in soil 160 are actively fixing nitrogen in chamber 102. In particular, controller 110 can receive one or more measurements of the amount or concentration of nitrous oxide in chamber 102, and determine (e.g., via comparison to reference information) an extent or rate of nitrogen fixation within the chamber. By measuring nitrous oxide amounts or concentrations associated with multiple plants in chamber 102, controller 110 can determine relative nitrogen fixation rates for microbes associated with each of the plants. Suitable nitrous oxide detectors for use in gas detector 114 include, but are not limited to, infrared spectrometric detectors, including non-dispersive infrared absorbance detectors. Nitrous oxide detectors are available commercially from Unisense A/S (Aarhus, Denmark).

Figure 5:
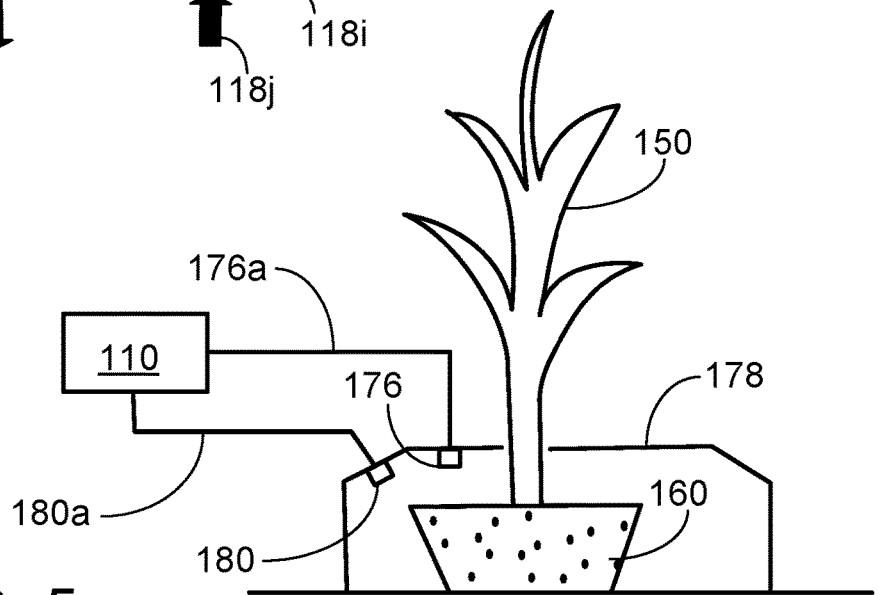
FIG. 5 is a schematic diagram of an example of a support structure for localizing detectors in proximity to plants within a chamber.

In some embodiments, nitrous oxide detectors can be mounted in proximity to plant 150 to measure an amount or concentration of nitrous oxide generated by microbes in soil 160. Mounting such detectors in this manner is particularly useful where chamber 102 includes multiple plants, and individual nitrous oxide amounts or concentrations are measured for the microbes associated with each plant. FIG. 5 shows an example of a nitrous oxide detector 176 mounted on a support structure 178 in proximity to plant 150. Detector 176 is connected to controller 110 via control line 176a, and generates a measurement signal that represents a nitrous oxide amount or concentration in the vicinity of detector 176.

In general, system 100 can include one or more (e.g., two or more, three or more, four or more, five or more, six or more, eight or more, ten or more, or even more) nitrous oxide detectors. In some embodiments, system 100 includes a nitrous oxide detector 176 on a support structure 178 associated with each plant 150 in chamber 102.

In some embodiments, gas detector 114 includes a detector configured to generate a measurement signal representing an amount or concentration of ammonia in chamber 102. Biological nitrogen fixation generates ammonia from gaseous nitrogen. Accordingly, measurements of ammonia amounts or concentrations in chamber 102 can be used to determine whether microbes present in soil 160 are actively fixing nitrogen in chamber 102. In particular, controller 110 can receive one or more measurements of the amount or concentration of ammonia in chamber 102, and determine (e.g., via comparison to reference information) an extent or rate of nitrogen fixation within the chamber. By measuring ammonia amounts or concentrations associated with multiple plants in chamber 102, controller 110 can determine relative nitrogen fixation rates for microbes associated with each of the plants. Suitable ammonia detectors for use in gas detector 114 include, but are not limited to, infrared spectrometric detectors and chemical detectors. Examples of such detectors are described in Timmer et al., "Ammonia sensors and their applications—a review," *Sensors and Actuators B: Chemical* 107(2): 666-677 (2005), the entire contents of which are incorporated herein by reference. Ammonia detectors are available commercially from Sensidyne, LP (St. Petersburg, FL), for example.

As discussed above in connection with nitrous oxide, in some embodiments, ammonia detectors can be mounted in proximity to plant 150 to measure an amount or concentration of ammonia generated by microbes in soil 160. Mounting such detectors in this manner is particularly useful where chamber 102 includes multiple plants, and individual ammonia amounts or concentrations are measured for the microbes associated with each plant. FIG. 5 shows an example of a nitrous oxide detector 180 mounted on support structure 178 in proximity to plant 150. Detector 180 is connected to controller 110 via control line 180a, and generates a measurement signal that represents an ammonia amount or concentration in the vicinity of detector 180.

In general, system 100 can include one or more (e.g., two or more, three or more, four or more, five or more, six or more, eight or more, ten or more, or even more) ammonia detectors. In some embodiments, system 100 includes an ammonia detector 180 on a support structure 178 associated with each plant 150 in chamber 102.

Returning to FIG. 1, in some embodiments, system 100 can optionally include a gas removal apparatus 116 connected to controller 110 via control line 116a. Controller 110 can activate gas removal apparatus 116, for example, to remove all or a portion of the gas from the enclosed spatial volume 104 in chamber 102, thereby adjusting the amounts or concentrations of one or more gases in chamber 102. For example, based on a measurement of one or more gases by gas detector 114, controller 110 can activate gas removal apparatus 116 to remove all or a portion of one or more measured gases from chamber 102.

In some embodiments, gas removal apparatus 116 is positioned within the enclosed spatial volume 104 of chamber 102. Alternatively, in certain embodiments, gas removal apparatus 116 is positioned external to chamber 102, and is connected to a port 116b formed in one or more walls of chamber 102.

Gas removal apparatus 116 can be implemented in various ways. In some embodiments, for example, gas removal apparatus 116 includes a pump with an inlet in fluid communication with port 116b, and an outlet that is not in fluid communication with chamber 102. Activation of the pump draws gas from chamber 102 into the pump through port 116b, and vents the gas through the pump outlet external to chamber 102.

In some embodiments, gas removal apparatus 116 includes one or more devices that are configured to specifically remove one or more certain types of gases from chamber 102. For example, in certain embodiments, gas removal apparatus 116 can be implemented as a gas exchanger, with one or more in-line gas scrubbing devices.

As described above, oxygen is a by-product of the growth of plant 150, and in some embodiments, gas removal apparatus 116 can include an oxygen scrubber. Controller 110 can selectively activate the oxygen scrubber to adjust the oxygen gas concentration in chamber 102, i.e., by removing some or all of the oxygen gas in the chamber. Suitable oxygen scrubbers are available commercially from Chromatography Research Supplies, Inc. (Louisville, KY).

In some embodiments, controller 110 activates gas removal apparatus 116 periodically to adjust the concentrations of one or more gases in chamber 102. Alternatively, or in addition, in certain embodiments, controller 110 activates gas removal apparatus 116 based on measurement signals from gas detector 114, e.g., when amounts or concentrations of one or more gases exceed corresponding reference values for plant 150.

In some embodiments, system 100 includes a temperature regulation apparatus 118 connected to controller 110 via control line 118a. The temperature regulation apparatus can include a temperature sensor 118d that generates a measurement signal representing a temperature within chamber 102.

Temperature regulation apparatus 118 can also include one or more heating elements 118b and one or more cooling elements 118c. Controller 110 can be configured to regulate the temperature within chamber 102 by selectively activating heating and/or cooling elements. Specifically, after receiving a measurement signal from temperature sensor 118d, controller 110 is configure to compare the measured temperature value to one or more reference temperature values for plant 150. If the measured temperature is too high based on the comparison, controller 110 activates one or more cooling elements 118c to reduce the chamber temperature. Alternatively, if the measured temperature is too low based on the comparison, controller 110 activates one or more heating elements 118b to increase the chamber temperature.

In some embodiments, the reference temperature values include representative daytime and nighttime temperature values, and controller 110 compares the measured temperature to appropriate daytime and nighttime temperature values, based on the time of the temperature measurement, before adjusting the chamber temperature. In this manner, controller 110 can implement both daytime and nighttime environmental conditions for plant 150.

The heating and cooling elements can be implemented in a variety of ways in temperature regulation apparatus 118. In some embodiments, for example, heating elements 118b can be implemented as resistive and/or infrared heating elements, activated by controller 110.

Figure 4:
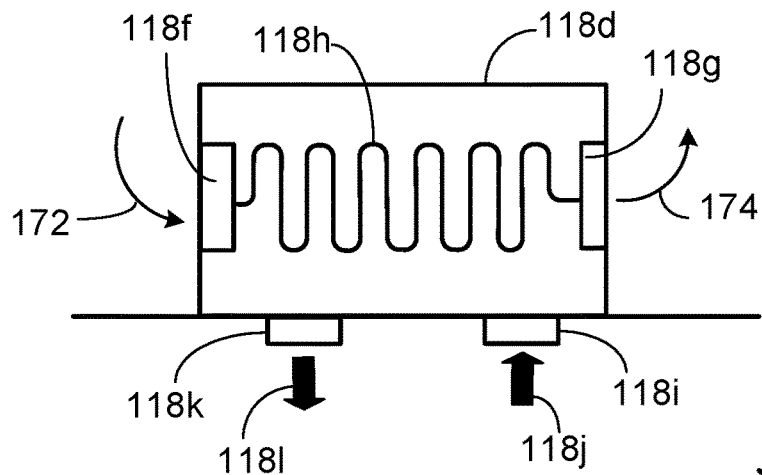
FIG. 4 is a schematic diagram of an example of a temperature regulation apparatus.

In certain embodiments, cooling elements 118c can be implemented as heat exchangers. FIG. 4 shows an example of a heat exchanging cooling element 118c. Cooling element 118c includes an inlet 118f, an exhaust fan 118g, and an enclosed gas flow path 118h extending between inlet 118f and exhaust fan 118g. A fan 118i draws in air 118j from outside chamber 102, circulates it over flow path 118h, and discharges the air 118l though port 118k.

During operation of cooling element 118c, chamber gas 172 enters inlet 118f, drawn in by fan 118g. The chamber gas 172 passes through gas flow path 118h and emerges as gas 174 from exhaust fan 118g. At the same time, fan 118i circulates external air 118j across the enclosed gas flow path 118h. As external air 118j is circulated, heat exchange occurs between external air 118j and chamber gas 172, transferring heat energy from chamber gas 172 to external air 118j. As a result, chamber gas 172 is cooled, and air 174 is returned to chamber 102 at a lower temperature than chamber gas 172. External air 118j is heated, and is exhausted through port 118k as waste air 118l.

Returning to FIG. 1, in some embodiments, system 100 includes an altitude sensor 120 connected to controller 110 via control line 120a. Altitude sensor 120 is configured to measure or obtain information about an altitude of chamber 102 (e.g., relative to a standard altitude such as sea level), and transmit the altitude information to controller 110. Altitude sensor 120 can be implemented, for example, as an altimeter that measures atmospheric gas pressure in the environment surrounding chamber 102 and compares the measured pressure to reference information to determine an altitude of chamber 102. Suitable altimeters for use in system 100 are widely available commercially.

In certain embodiments, controller 110 is configured to adjust the amounts of gas delivered to chamber 102 based on altitude measurements provided by altitude sensor 120. During operation of system 100, controller 110 delivers gases to chamber 102 according to reference information (e.g., a set of growth conditions) for plant 150. The reference information includes concentrations of gases such as nitrogen and carbon dioxide, and controller 110 activates gas delivery apparatus 106 and (if necessary) gas removal apparatus 116 to ensure that appropriate concentrations of these gases are maintained during the growth cycle of plant 150 in chamber 102. To account for growing conditions at different altitudes, however, controller 110 can adjust the amounts or concentrations of one or more gases in chamber 102 based on the measured altitude information described above.

Returning to FIG. 1, in some embodiments, system 100 includes a light source 122 connected to controller 110 via control line 122a and configured to generate light to stimulate growth of plant 150. Controller 110 can be configured to activate light source 122 for periods of time to simulate daytime growing conditions, and to de-activate light source 122 to simulate nighttime conditions. During operation of system 100, controller 110 delivers light to the plant(s) in chamber 102 for periodic intervals according to reference information (e.g., a set of growth conditions) for plant 150. The reference information typically includes the lengths of illumination periods and, in some embodiments, the illumination intensity. Controller 110 selectively activates light source 122 to provide light to plant(s) 150 for the prescribed time intervals, and in certain embodiments, at the prescribed light intensity levels.

Any of a wide variety of different light-generating elements can be used in light source 122. Suitable elements for use in light source 122 include, but are not limited to, metal halide light sources, halogen light sources, fluorescent sources, incandescent sources, and light-emitting diode (LED) sources.

In some embodiments, system 100 includes a humidity control apparatus 124 connected to controller 110 via control line 124*a*. Humidity control apparatus 124 includes a humidity sensor 124*b* configured to generate a measurement signal that represents a humidity within the enclosed spatial volume 104 of chamber 102. Humidity control apparatus 124 also optionally includes a humidifier 124*c* and/or a de-humidifier 124*d* connected to a port formed in the one or more walls of chamber 102. Controller 110 receives the humidity measurement signal from humidity sensor 124*b* and can selectively activate humidifier 124*c* and/or de-humidifier 124*d* if the chamber humidity is too low or too high, respectively, relative to a reference humidity value for plant 150. Typically, the reference humidity value is part of reference information (e.g., a set of growth conditions) for plant 150.

In some embodiments, system 100 includes a growth monitoring apparatus 126 connected to controller 110 via control line 126*a*. In general, growth monitoring apparatus 126 is configured to generate a measurement signal that includes information about the growth of plant 150 within chamber 102. Controller 110 receives the information and can execute a variety of control functions based on the information.

Figure 6:
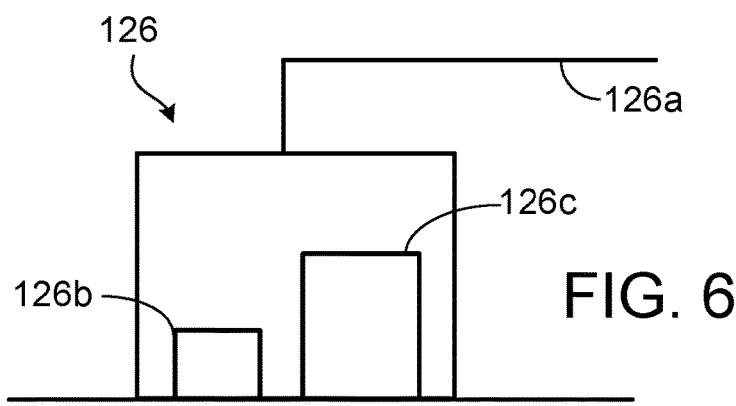
FIG. 6 is a schematic diagram of an example of a growth monitoring apparatus.

FIG. 6 shows an example of growth monitoring apparatus 126, which includes a radiation source 126*b* and a detector 126*c*. Radiation source 126*b* generates and directs illumination light to be incident on plant 150, and detector 126*c* detects light emitted from plant 150. The emitted light can be transmitted through or reflected from plant 150, for example. In some embodiments, detector 126*c* is an imaging detector configured to obtain one or more images of plant 150 (or portions thereof). In certain embodiments, detector 126*c* is a non-imaging detector. In some embodiments, detector 126*c* is a spectral detector, and measures emitted light as a function of wavelength or frequency. In certain embodiments, detector 126*c* includes detection elements of multiple types, including one or more of any of the foregoing detector types.

In some embodiments, detector 126*c* is configured to detect light emitted from plant 150 (or portions thereof) in three distinct spectral bands, the three bands having local maxima in the red (between 635 nm and 700 nm), green (between 520 nm and 560 nm), and blue (between 450 nm and 490 nm) regions of the electromagnetic spectrum. Controller 110 can use the detected light measurements to determine a measure of growth of plant 150.

More generally, detector 126*c* can be configured to detect light emitted from plant 150 (or portions thereof) in multiple distinct spectral bands, each having a different local maximum spectral wavelength. Light can be detected by detector 126 in three or more (e.g., four or more, five or more, six or more, seven or more, eight or more, ten or more, or even more) distinct spectral bands, and controller 110 can use the detected light measurements to determine a measure of growth of plant 150.

In some embodiments, detector 126*c* is configured to measure a hyperspectral image of plant 150 (or a portion thereof) by measuring the spectral intensity of the emitted light as a function of wavelength or frequency for multiple pixels within the image. Each wavelength of frequency of measurement in the hyperspectral image corresponds to a different wavelength band with a different local maximum wavelength or frequency. Controller 110 can use the hyperspectral image information to determine a measure of growth of plant 150.

In certain embodiments, detector 126*c* is configured to measure emitted light in one or more infrared spectral regions or bands. The regions can include the near-IR (e.g., 800 nm to 1400 nm) and/or the short-wavelength IR (e.g., 1400 nm to 3000 nm). Image and/or non-image information measured in one or more of the foregoing spectral regions can be used by controller 110 to determine a measure of growth of plant 150.

In some embodiments, detector 126*c* is configured to measure fluorescence emission from plant 150 (or a portion thereof). Detector 126*c* can obtain one or more fluorescence images of plant 150, or can measure fluorescence intensity in a non-spatially resolved manner. Controller 110 can use the fluorescence image information and/or the fluorescence measurements to determine a measure of growth of plant 150.

In certain embodiments, source 126*b* and detector 126*c* are implemented as a laser scanner that is configured to direct incident light to the surface of plant 150 (or portions thereof) and detect reflected light from plant 150 to obtain image information (e.g., a topographical map) of plant 150. For example, by projecting a pattern of structured light onto the surface of plant 150 and measuring images of the distorted patterns on the surfaces of plant 150, the topographical structure of the surfaces of plant 150 can be calculated by controller 110. Alternatively, the laser scanner can be used to track positions of one or more features of plant 150, including leaf features (e.g., tip positions and dimensions). Controller 110 can use the laser scanning information to determine a measure of growth of plant 150.

Returning to FIG. 1, in some embodiments, the growth monitoring apparatus can include a sensor 126*d* positioned on, or integrated into, the surface of chamber 102 (surface 102*c* in FIG. 1) that supports plant 150, and optionally connected to controller 110 via control line 126*e*. Sensor 126*d* is configured to obtain a measurement of the mass of plant 150, which controller 110 can use to determine a measure of growth of plant 150.

In certain embodiments, sensor 126*d* can be implemented as a scale. More generally, sensor 126*d* can be implemented as a touch-sensitive sensor that generates a measurement signal that includes information about the force applied to the sensor when plant 150 (or portions thereof) are in contact with the sensor.

In some embodiments, system 100 can include a soil moisture detector 128 connected to controller 110 via control line 128*a*. Soil moisture detector 128 is configured to generate a measurement signal that includes information about a percentage of water in soil 160 within chamber 102. Soil moisture detector 128 can be implemented in various ways. In some embodiments, soil moisture detector 128 includes a probe 128*b* that contacts soil 160, and generates a measurement signal. In certain embodiments, soil moisture detector 128 is implemented as a scale that generates a measurement signal representing the mass of soil 160, from which controller 110 can determine the percentage of water in soil 160.

In some embodiments, system 100 can include one or more auxiliary sensors 136 connected to controller 110 via control lines 136a. In general, the auxiliary sensors can be chemical sensors that each generate a measurement signal in response to the presence of one or more chemical species (e.g., analytes) in chamber 102. Each of the auxiliary sensors can correspond to any of the types of sensors described above, or to other types of sensors. Auxiliary sensors 136 can be dedicated to the detection of chemical species that include, but are not limited to, amounts or concentrations of ammonia, amounts of nitrate ions and/or nitrate salts, amounts or concentrations of nitrous oxide, and amounts or concentrations of carbon dioxide.

In certain embodiments, system 100 can include a fluid removal mechanism 130 connected to controller 110 via control line 130a. Fluid removal mechanism 130 includes a conduit 130b connected to or extending through a port formed in one or more walls of chamber 102. Controller 110 can activate fluid removal mechanism 130 to extract a variety of fluids from chamber 102, including gases and liquids.

Figure 7:
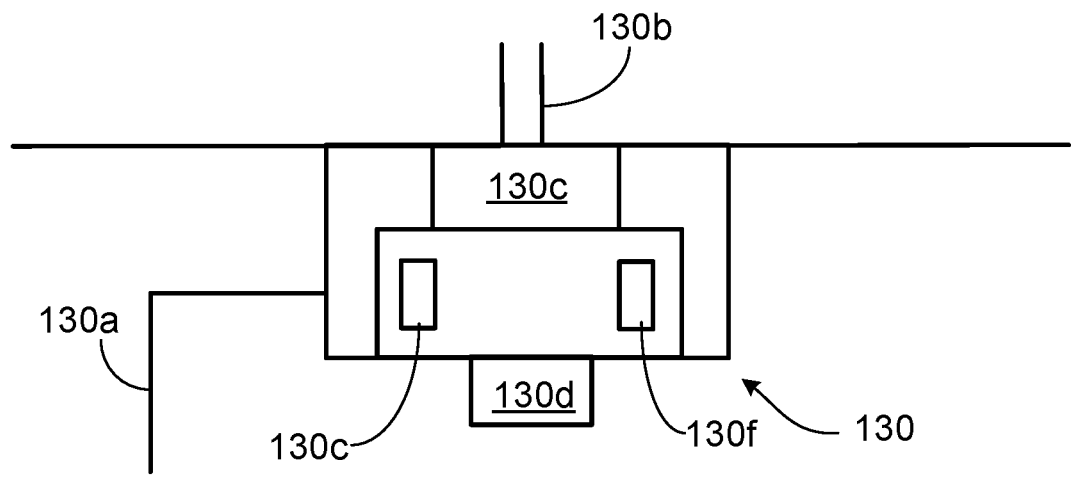
FIG. 7 is a schematic diagram of an example of a fluid removal mechanism.

FIG. 7 shows an example of a fluid removal mechanism 130. In addition to conduit 130b and control line 130a, fluid removal mechanism 130 can optionally include a fluid pump 130c that can be activated by controller 110 to facilitate fluid flow through fluid removal mechanism 130. Alternatively, or in addition, fluid removal mechanism can include a pressure-reducing device (such as a vacuum source) that draws fluid from chamber 102 into conduit 130b and out of chamber 102.

In some embodiments, conduit 130b is configured to extract a fluid directly from plant 150. For example, conduit 130b can be terminated with a syringe that penetrates a tissue of plant 150 to extract a fluid from the tissue. In some embodiments, conduit 130b is configured to extract a fluid directly from soil 160. For example, conduit 130b can be positioned directly in soil 160 to capture a portion of the growth medium delivered to plant 150 by the nutrient delivery apparatus.

In certain embodiments, fluid removal mechanism 130 can include, or can be connected to, a fluid analysis apparatus. The fluid analysis apparatus can be implemented in various ways. For example, the fluid analysis apparatus can optionally include a mass spectrometry detector 130d that analyzes components of the fluid extracted through conduit 130b. Alternatively, or in addition, the fluid analysis apparatus can optionally include a light source 130e and a detector 130f configured to detect light emitted from the extracted fluid in response to illumination light generated by light source 130e. Information obtained from the fluid analysis apparatus can be transmitted to controller 110.

Returning to FIG. 1, sampling apparatus 112 can generally be implemented in a variety of ways. In some embodiments, sampling apparatus 112 includes an auxiliary chamber 112a connected to chamber 102 via a sealing mechanism 112b. Various sealing mechanisms 112b can be used, including gaskets, flanged vacuum connectors, and mechanical engagement mechanisms. In some embodiments, the sealing mechanism 112b can be deployed and retracted. When deployed, the sealing mechanism disconnects the interior volume of auxiliary chamber 112a from the enclosed spatial volume 104 of chamber 102. When retracted, the interior volume of auxiliary chamber 112a and the enclosed spatial volume 104 of chamber 102 are in fluid communication.

As an alternative sampling apparatus 112, in some embodiments, sampling apparatus 112 can be implemented as a cover connected through a sealing mechanism to a port formed in one or more walls of chamber 102. Any of the above sealing mechanisms can generally be used to connect the cover to the port, as can other sealing mechanisms such as fasteners, hinges, magnetic couplers, and electrostatic fasteners.

In some embodiments, system 100 includes one or more gloves 134 connected through sealing members to one or more ports formed in the walls of chamber 102. A user of system 100 can insert his or her hands into gloves 134, allowing the user to manipulate plants and other objects within chamber 102, without opening chamber 102. The sealing members used to connected gloves 134 to ports in the walls of chamber 102 can include any of the different types of sealing members discussed above.

In some embodiments, sampling apparatus can be used to perform one or more assays on the tissue of plant 150. For example, plant tissue can be extracted from chamber 102 via sampling apparatus 112 for purposes of evaluating the colonization ability of microbes with which the plant was inoculated. To test for the colonization ability of the microbes, the extracted plant tissue is assayed to test for the presence of nucleic acids in the plant tissue that are characteristic of the microbes. By extracting and testing a variety of plant tissues, the colonization ability of the microbes can be assessed.

As an alternative to the foregoing procedure, the colonization ability of the microbes can be determined without excising plant tissue using the growth monitoring apparatus 126. For example, for microbes that express a fluorophore (such as a fluorescence protein), the growth monitoring apparatus 126 can be used to detect fluorescence emission from the fluorophore. By imaging fluorescence emission from a variety of plant tissues within chamber 102, the colonization ability of the microbes can be assessed.

In some embodiments, system 100 can include an inoculation mechanism 132 connected to controller 110 via control line 132a. Inoculation mechanism 132 is configured to deliver an inoculation composition to plant 150 within the enclosed spatial volume 104 of chamber 102.

Figure 8:
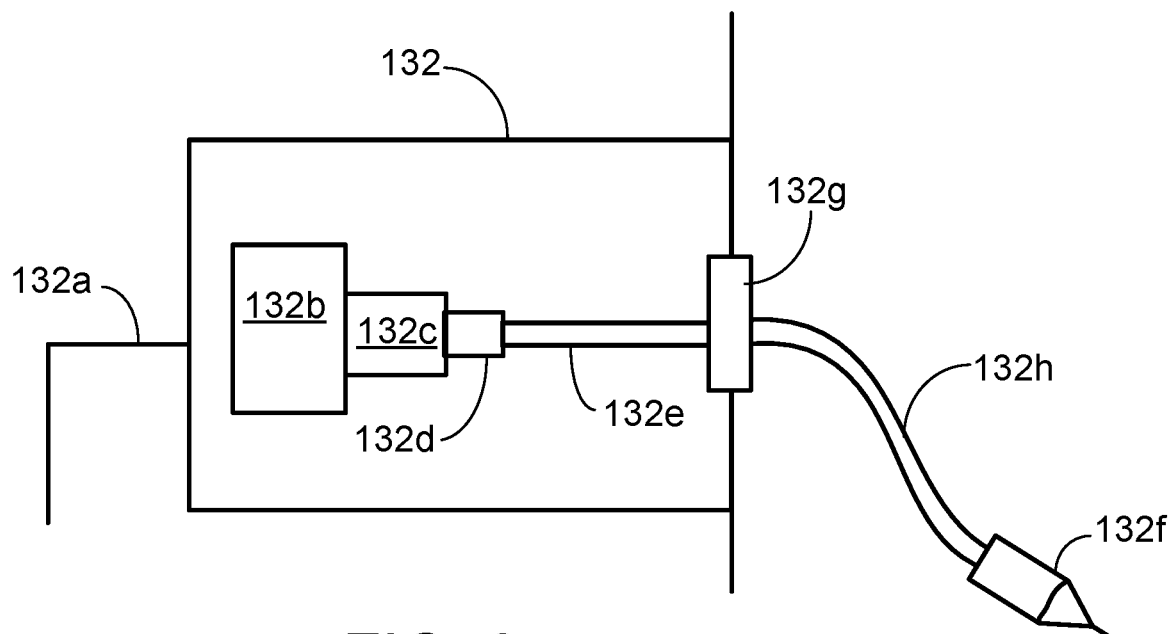
FIG. 8 is a schematic diagram of an example of an inoculation mechanism.

FIG. 8 shows an example of an inoculation mechanism 132. Mechanism 132 includes a reservoir 132b for storing an inoculation composition that includes one or more microbes, a metering mechanism that can be activated by controller 110 and includes a pump 132c and a valve 132d, and a conduit that connects reservoir 132b to a port 132g in a wall of chamber 132. A second conduit 132h connects port 132g to a syringe 132f for delivery of the inoculation composition to plant 150.

During operation, controller 110 activates pump 132c and valve 132d of the metering mechanism to deliver a metered volume of the inoculation composition into conduit 132e. Port 132g is generally configured to be selectively opened and closed to connect conduits 132e and 132h. Controller 110 activates port 132g to selectively open the port and allow the metered volume of inoculation composition to flow through conduit 132 and out of syringe 132f, delivering the inoculation composition to plant 150.

In some embodiments, system 100 is configured to perform an acetylene reduction assay to assess the nitrogen-fixing ability of microbes associated with plant 150. Gas delivery apparatus 106 can include a source of acetylene gas 106b, and system 100 can include an auxiliary sensor 136 configured to detect ethylene gas by generating a measurement signal representing an amount or concentration of ethylene gas in proximity to the sensor.

To perform the acetylene reduction assay, controller 110 activates the gas delivery apparatus 106 to deliver a quantity of acetylene gas to soil 160 in which plant 150 is positioned. After a measurement time elapses, controller 110 activates the auxiliary ethylene sensor 136 to measure an amount of ethylene generated by the microbes in soil 160. Controller 110 then determines the rate of acetylene reduction based on the amount of ethylene generated and the elapsed measurement time.

As discussed above in connection with nitrous oxide measurements, acetylene reduction assays can be performed in parallel for multiple plants 150 in chamber 102 by activating multiple ethylene sensors 136 in chamber 102, where each of the ethylene sensors 136 is associated with a different plant. To associate individual sensors with specific plants, the sensors can be positioned on support structures (e.g., support structures 178, as shown in FIG. 5) such that the sensors are in proximity to specific plants.

Figure 12:
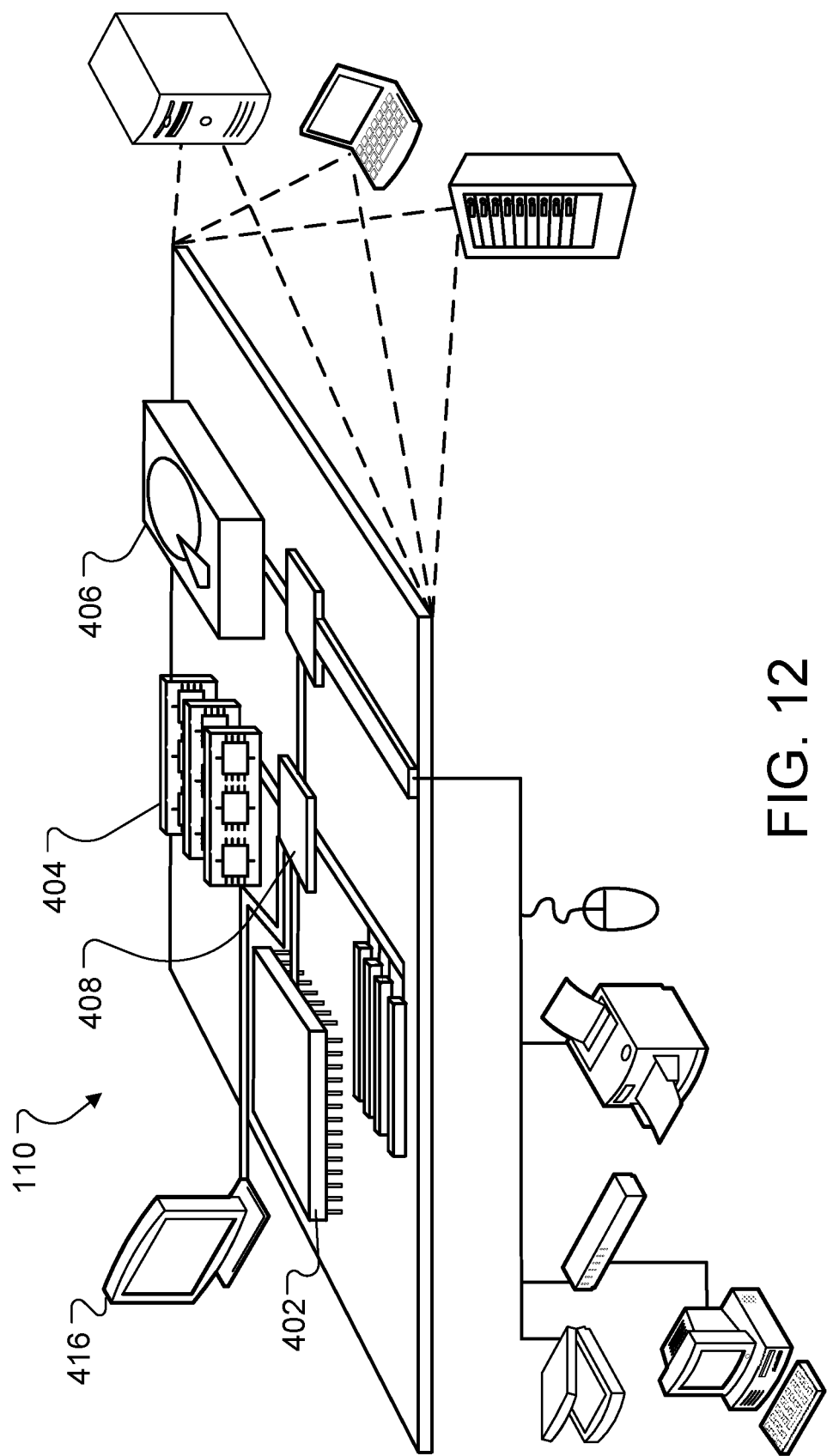
FIG. 12 is a schematic diagram of an example of a controller.

FIG. 12 shows an example of controller 110, which may be used with the systems and methods disclosed herein. Controller 110 can include one or more processors 402, memory 404, a storage device 406 and interfaces 408 for interconnection. The processor 402 can process instructions for execution within the controller, including instructions stored in the memory 404 or on the storage device 406. For example, the instructions can instruct the processor 402 to perform any of the analysis and control steps disclosed herein.

The memory 404 can store executable instructions for processor 402, information about parameters of the system such as excitation and detection wavelengths, and measured spectral image information. The storage device 406 can be a computer-readable medium, such as a floppy disk device, a hard disk device, an optical disk device, or a tape device, a flash memory or other similar solid state memory device, or an array of devices, including devices in a storage area network or other configurations. The storage device 406 can store instructions that can be executed by processor 402 described above, and any of the other information that can be stored by memory 404.

In some embodiments, controller 110 can include a graphics processing unit to display graphical information (e.g., using a GUI or text interface) on an external input/output device, such as display 416. The graphical information can be displayed by a display device (e.g., a CRT (cathode ray tube) or LCD (liquid crystal display) monitor) for displaying any of the information, such as measured and calculated spectra and images, disclosed herein. A user can use input devices (e.g., keyboard, pointing device, touch screen, speech recognition device) to provide input to controller 110.

A user of system 100 can provide a variety of different types of instructions and information to controller 110 via input devices. The instructions and information can include, for example, reference information such as: growth conditions for plant(s) 150; reference information and values for quantities such as isotope abundances in plant tissues to which controller 110 can compare measured values; reference values and ranges for various environmental parameters and conditions in chamber 102 that are maintained by controller 110 such as, but not limited to, temperatures, humidities, soil moisture percentages, nutrient and growth medium delivery schedules, gas concentrations, altitude-based calibrations and adjustments, and illumination schedules; and calibration information and reference values associated with various assays, including reference concentrations of any of the species described herein in connection with extracted fluids, calibration information for performing any of the assays described herein, and calibration information used by controller 110 to calibrate any of the detectors and sensors described herein. Controller 110 can use any of these various types of information to perform the methods and functions described herein. It should also be noted that any of these types of information can be stored (e.g., in storage device 406) and recalled when needed by controller 110.

The methods disclosed herein can be implemented by controller 110 by executing instructions in one or more computer programs that are executable and/or interpretable by the controller 110. These computer programs (also known as programs, software, software applications or code) include machine instructions for a programmable processor, and can be implemented in a high-level procedural and/or object-oriented programming language, and/or in assembly/machine language. For example, computer programs can contain the instructions that can be stored in memory 404, in storage unit 406, and/or on a tangible, computer-readable medium, and executed by processor 402 as described above. As used herein, the term "computer-readable medium" refers to any computer program product, apparatus and/or device (e.g., magnetic discs, optical disks, memory, Programmable Logic Devices (PLDs), ASICs, and electronic circuitry) used to provide machine instructions and/or data to a programmable processor, including a machine-readable medium that receives machine instructions.

Detecting Nitrogen Incorporation and Identifying Nitrogen-Fixing Microbes

Figure 9:
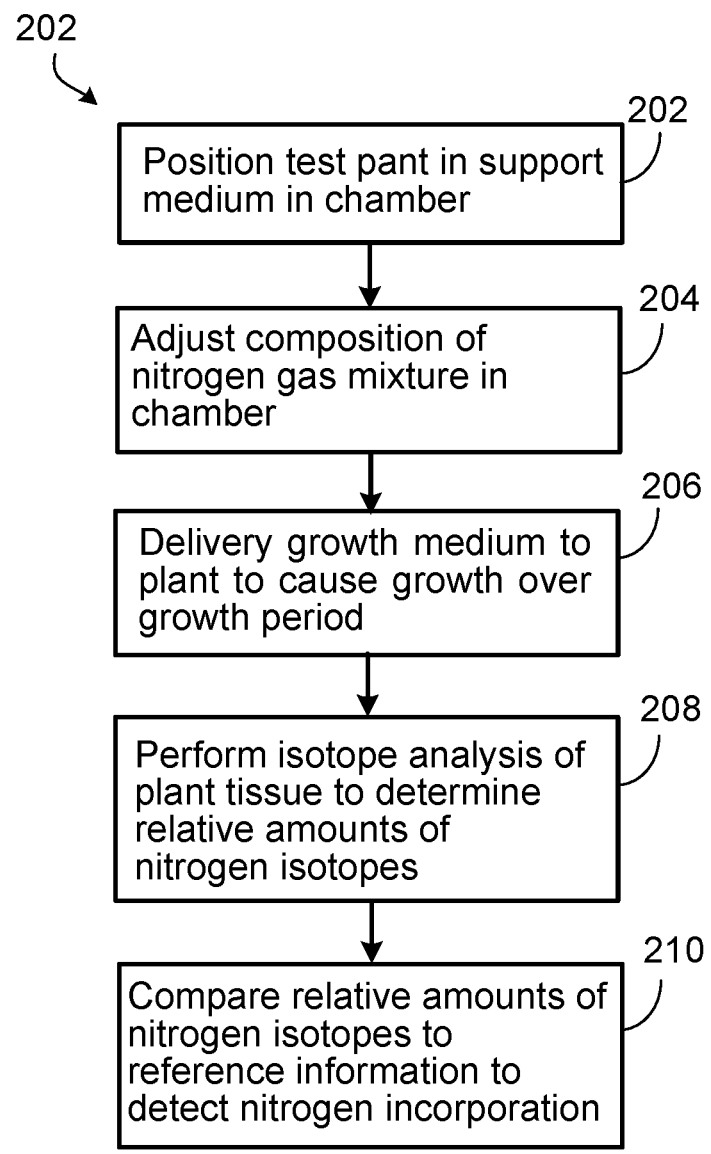
FIG. 9 is a flow chart showing a series of example steps for performing an assay to detect nitrogen incorporation in plant tissue.

The systems described herein can be used to perform a variety of assays and determinations in semi-automated or fully automated fashion. For example, in some embodiments, the systems can be used to detect nitrogen incorporation in a plant. FIG. 9 is a flow chart 200 that includes a series of example steps for performing an assay to detect nitrogen incorporation in plant tissue.

In a first step 202, a test plant (e.g., plant 150) is positioned in a support medium (e.g., soil 160) within the enclosed spatial volume 104 of chamber 102. Next, as described above, controller 110 activates the gas delivery apparatus 106 to adjust a composition of a nitrogen gas mixture within chamber 102 so that the abundance ratio of at least two nitrogen isotopes is different from the naturally occurring atmospheric ratio of the two isotopes (i.e., the ratio of the isotopes in atmospheric nitrogen gas). As discussed previously, the nitrogen isotopes can be, for example, $^{15}N$ and $^{14}N$, or $^{13}N$ and $^{14}N$, or $^{15}N$ and $^{13}N$ and $^{14}N$, and the adjustment can include increasing the relative abundance of either $^{15}N$ or $^{13}N$, as these nitrogen isotopes are effectives used to label plant tissues in which nitrogen incorporation occurs.

After adjustment of the nitrogen gas composition, controller 110 actives the nutrient delivery apparatus 108 to deliver an aqueous growth medium to the test plant to cause growth of the test plant over a growth period. Controller 110 can also maintain suitable growth conditions for the test plant (e.g., defined in reference information for the test plant) by selectively activating the gas delivery apparatus 106, gas removal apparatus 116, temperature regulation apparatus 118, light source 122, and humidity control apparatus 124 in response to corresponding measurements of various conditions within chamber 102 discussed previously.

In general, the growth period can be selected as desired. For example, in some embodiments, the growth period is at least 7 days (e.g., at least 8 days, at least 9 days, at least 10 days, at least 11 days, at least 12 days, at least 13 days, at least 14 days, at least 15 days, at least 16 days, at least 17 days, at least 18 days, at least 21 days, at least 24 days, at least 27 days, at least 30 days). In certain embodiments, the growth period is 50 days or less (e.g., 45 days or less, 40 days or less, 35 days or less, 30 days or less, 25 days or less, 20 days or less, 18 days or less, 16 days or less, 14 days or less, 12 days or less, 10 days or less).

Next, in step 208, an isotope analysis of test plant tissue is performed to determine relative amounts of the at least two nitrogen isotopes from step 204 in the test plant tissue. The isotope analysis can be performed in various ways. In some embodiments, for example, the isotope analysis is performed by harvesting plant tissue, drying the harvested plant tissue, grinding the dried tissue into a powder, and performing a mass spectrometric analysis of the power to determine relative abundances of the at least two isotopes.

Alternatively, in some embodiments, the isotope analysis of the test plant tissue is performed within chamber 102, without harvesting the test plant tissue. As discussed above, system 100 can include a gas detector 114 that includes an isotope ratio infrared spectrometry detector, which can detect amounts or concentrations of different nitrogen isotopes via infrared absorption measurements directly on intact tissue. The isotope ratio infrared spectrometry detector yields measurements of the relative amounts (e.g., abundances) of each of the nitrogen isotopes in the test plant tissue.

Performing isotope analysis via isotope ratio infrared spectroscopy generally does not damage plant tissue or interrupt growth cycles, and as a result, can be advantageous for performing periodic assessment of nitrogen incorporation in plant tissue. That is, isotope analysis can be performed repeatedly, at specific periodic intervals or at irregular times, to assay nitrogen incorporation as a function of time during the test plant's growth cycle. Between repeated measurements, controller 110 can selectively activate gas delivery apparatus 106 to adjust the composition of the nitrogen gas mixture in the chamber, e.g., to maintain the initial adjusted composition.

Next, in step 210, controller 110 compares the relative amounts of the nitrogen isotopes in the test plant tissue to reference information to determine whether nitrogen incorporation has occurred in the test plant tissue as a result of biological nitrogen fixation. Typically, the reference information corresponds to an expected ratio of the isotope abundances in the test plant tissue in the absence of biological nitrogen fixation by microbes in soil 160. When an increase in the abundance of the lower abundance isotope is measured (relative to the expected abundance), controller 110 determines that nitrogen incorporation has been enhanced due to the nitrogen-fixing activity of soil microbes.

As an example, when controller 110 adjusts the nitrogen gas mixture in chamber 102 to enrich the mixture in $^{15}N$ relative to $^{14}N$, the abundances of $^{15}N$ and $^{14}N$ in the plant tissue are compared to reference information for the expected abundances of $^{15}N$ and $^{14}N$ in the plant tissue. If the measured abundance of $^{15}N$ in the plant tissue is larger than the expected abundance of $^{15}N$ in the plant tissue, controller 110 determines that nitrogen incorporation has occurred, and has been enhanced via biological nitrogen fixation by the microbes associated with the test plant relative to the extent of nitrogen incorporation that would occur in the absence of the microbes.

A variety of different plant tissues can be assayed using the methods described above. For example, plant tissues that can be examined to assess nitrogen incorporation include root tissue, newly emerged whorl tissue, top-collared leaf tissue, and other plant tissue.

In some embodiments, controller 110 obtains the reference isotope abundance information (i.e., the expected isotope abundances) from a storage unit containing previously measured reference information. Alternatively, in certain embodiments, the reference isotope abundance information is measured in chamber 102 during the assay. For example, a reference plant that has not been inoculated with a microbe composition can be placed in a support medium within chamber 102, and an aqueous growth medium delivered to the reference plant (i.e., the same growth medium delivered to the test plant) as described above in connection with steps 202 and 206. Isotope analysis is also performed on tissue(s) of the reference plant to determine relative abundances of nitrogen isotopes in the reference plant tissues in step 208. These isotope abundances for the reference plant tissues correspond to the reference information (i.e., the expected isotope abundances) that are used in step 210.

To assay the increase in nitrogen incorporation resulting from particular microbes, in some embodiments, the test plant (or a seed precursor of the test plant) can be inoculated with a composition that includes a bacterial suspension. The bacterial suspension can include, for example, one or more nitrogen-fixing bacteria. In general, inoculation can occur before or after the test plant (or a seed precursor of the test plant) is placed in chamber 102, and before or after the reference plant is placed in chamber 102. Various modes of inoculation can be used, and following inoculation, the nitrogen-fixing bacteria can be present in the support medium (e.g., soil 160) and/or in the tissues of the test plant.

It should also be noted that any of the other measurements or assays described herein can also be performed as part of the methods represented in FIG. 9.

Figure 10:
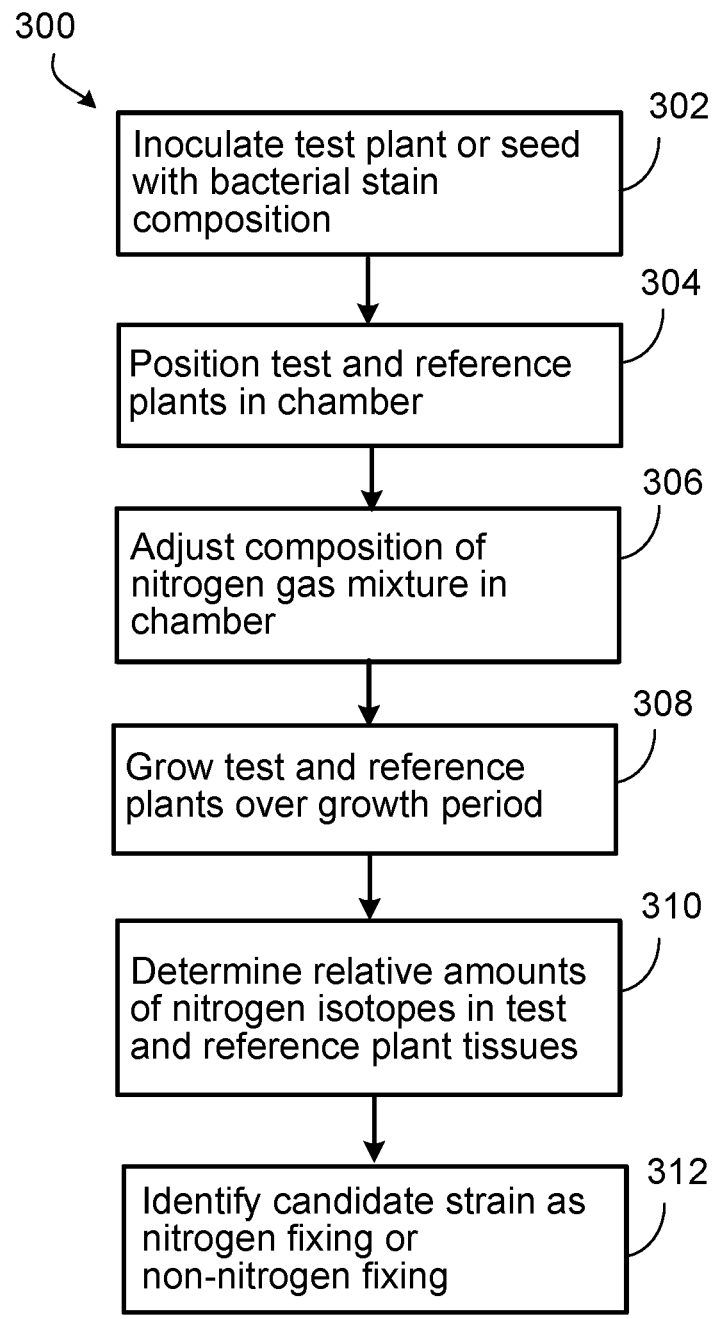
FIG. 10 is a flow chart showing a series of example steps for identifying bacterial strains that perform biological nitrogen fixation.

In some embodiments, the systems described herein can be used to identify a nitrogen-fixing bacterial strain. FIG. 10 is a flow chart 300 that shows a series of example steps for identifying bacterial strains that perform biological nitrogen fixation. In a first step 302, a test plant or a seed precursor of a test plant is inoculated with a composition that includes at least one bacterium of a candidate bacterial strain. Inoculation typically involves contacting a portion of the test plant (e.g., the roots) or its precursor seed with an aqueous suspension of the candidate bacterial strain. It should be noted that a reference plant used in this assay is not inoculated with the candidate bacterial strain.

Next, in step 304, the test and reference plants are positioned in support media within chamber 102, and in step 306, controller 110 adjusts the composition of the nitrogen gas mixture in chamber 102 so that a ratio of at least two nitrogen isotopes in the gas differs from the naturally occurring atmospheric ratio of the isotopes (i.e., their abundance ratio in atmospheric nitrogen gas). This step is performed in a manner similar to step 204 discussed above.

Then, in step 308, the test and reference plants are grown in chamber 102 over a growth period. To grow the test and reference plants, controller 110 activates nutrient delivery system 108 to deliver growth media to the plants, and adjusts various environmental growth conditions in the manner discussed above.

In general, the growth period can be selected as desired. For example, in some embodiments, the growth period is at least 7 days (e.g., at least 8 days, at least 9 days, at least 10 days, at least 11 days, at least 12 days, at least 13 days, at least 14 days, at least 15 days, at least 16 days, at least 17 days, at least 18 days, at least 21 days, at least 24 days, at least 27 days, at least 30 days). In certain embodiments, the growth period is 50 days or less (e.g., 45 days or less, 40 days or less, 35 days or less, 30 days or less, 25 days or less, 20 days or less, 18 days or less, 16 days or less, 14 days or less, 12 days or less, 10 days or less).

In step 310, after the growth period, controller 110 determines relative amounts of nitrogen isotopes in test and reference plant tissues. This isotope analysis can be performed according to any of the methods described above. In particular, in some embodiments, test and reference plant tissues are harvested, dried, ground into powders, and the powders are analyzed by mass spectrometry to determine nitrogen isotope abundances in the tissues.

In certain embodiments, as discussed above, system 100 can include a gas detector 114 that includes an isotope ratio infrared spectrometry detector, which can detect amounts or concentrations of different nitrogen isotopes via infrared absorption measurements directly on intact tissue. The isotope ratio infrared spectrometry detector yields measurements of the relative amounts (e.g., abundances) of each of the nitrogen isotopes in the test and reference plant tissues. Using a detector of this type allows isotope abundance measurements to be made at periodic or regulator intervals, so that the ability of the candidate bacterial strain to perform nitrogen fixation can be assessed as a function of time, and under changing environmental conditions.

In step 312, controller compares the relative amounts of the nitrogen isotopes in the test and reference plant tissues. If the lower abundance isotope in the adjusted chamber nitrogen gas mixture (e.g., $^{15}N$ or $^{13}N$) from step 306 is present at higher relative abundance in the test plant tissue than in the reference plant tissue, controller 110 identifies the candidate strain as a nitrogen-fixing bacterial strain. If the lower abundance isotope in the adjusted chamber nitrogen gas mixture (e.g., $^{15}N$ or $^{13}N$) from step 306 is present at the same or lower relative abundance in the test plant tissue than in the reference plant tissue, controller 110 identifies the candidate strain as a non-nitrogen-fixing bacterial strain.

A variety of different test and reference plant tissues can be assayed using the methods described above. For example, the test and reference plant tissues that are analyzed can include root tissue, newly emerged whorl tissue, top-collared leaf tissue, and other plant tissue.

In some embodiments, as described above, a seed precursor of the test plant is inoculated with the candidate bacterial strain. In these circumstances, germination of the seed can be carried out external to chamber 102 to yield a test plant which is then positioned within chamber 102. To germinate the inoculated seed, the seed can be deposited in a support medium to induce germination, yielding the test plant. Following germination of the seed, growth medium can be withheld from the test plant for a period of 3 days or more (e.g., 5 days or more, 7 days or more, 10 days or more, 12 days or more, 14 days or more), and then delivered to the test plant following this initial period.

The time at which the test plant is positioned within chamber 102 following germination can generally be selected based on factors such as the size of the plant and the point(s) in the plant's growth cycle during which assessment of the nitrogen-fixing effectiveness of candidate bacterial strains is of interest. In some embodiments, for example, the test plant can be positioned within chamber 102 at least 10 days (e.g., at least 14 days, at least 16 days, at least 18 days, at least 21 days, at least 24 days, at least 27 days, at least 30 days) following germination of its precursor seed.

Genetic Regulation of Nitrogen Fixation
(1) NifA

In proteobacteria, regulation of nitrogen fixation centers on the σ54-dependent enhancer-binding protein NifA, the positive transcriptional regulator of the nif cluster. NifA upregulates the nif gene complex and drives nitrogen fixation when there is insufficient fixed nitrogen available to the microbe. NifL inhibits NifA when there is sufficient fixed N available to the microbe. Intracellular levels of active NifA are controlled by two key factors: transcription of the nifLA operon, and inhibition of NifA activity by protein-protein interaction with NifL. Both of these processes are responsive to intracelluar glutamine levels via the PII protein signaling cascade. This cascade is mediated by GlnD, which directly senses glutamine and catalyzes the uridylylation or deuridylylation of two PII regulatory proteins—GlnB and GlnK—in response the absence or presence, respectively, of bound glutamine. Under conditions of nitrogen excess, unmodified GlnB signals the deactivation of the nifLA promoter. However, under conditions of nitrogen limitation, GlnB is post-translationally modified, which inhibits its activity and leads to transcription of the nifLA operon. In this way, nifLA transcription is tightly controlled in response to environmental nitrogen via the PII protein signaling cascade. On the post-translational level of NifA regulation, GlnK inhibits the NifL/NifA interaction in a matter dependent on the overall level of free GlnK within the cell.

NifA is transcribed from the nifLA operon, whose promoter is activated by phosphorylated NtrC, another σ54-dependent regulator. The phosphorylation state of NtrC is mediated by the histidine kinase NtrB, which interacts with deuridylylated GlnB but not uridylylated GlnB. Under conditions of nitrogen excess, a high intracellular level of glutamine leads to deuridylylation of GlnB, which then interacts with NtrB to deactivate its phosphorylation activity and activate its phosphatase activity, resulting in dephosphorylation of NtrC and the deactivation of the nifLA promoter. However, under conditions of nitrogen limitation, a low level of intracellular glutamine results in uridylylation of GlnB, which inhibits its interaction with NtrB and allows the phosphorylation of NtrC and transcription of the nifLA operon. In this way, nifLA expression is tightly controlled in response to environmental nitrogen via the PII protein signaling cascade. nifA, ntrB, ntrC, and glnB, are all genes that can be mutated in the methods described herein. These processes can also be responsive to intracellular levels of ammonia, urea or nitrates.

The activity of NifA is also regulated post-translationally in response to environmental nitrogen, most typically through NifL-mediated inhibition of NifA activity. In general, the interaction of NifL and NifA is influenced by the PII protein signaling cascade via GlnK, although the nature of the interactions between GlnK and NifL/NifA varies significantly between diazotrophs. In *Klebsiella pneumoniae*, both forms of GlnK inhibit the NifL/NifA interaction, and the interaction between GlnK and NifL/NifA is determined by the overall level of free GlnK within the cell. Under nitrogen-excess conditions, deuridylylated GlnK interacts with the ammonium transporter AmtB, which serves to both block ammonium uptake by AmtB and sequester GlnK to the membrane, allowing inhibition of NifA by NifL. On the other hand, in *Azotobacter vinelandii*, interaction with deuridylylated GlnK is required for the NifL/NifA interaction and NifA inhibition, while uridylylation of GlnK inhibits its interaction with NifL. In diazotrophs lacking the nifL gene, there is evidence that NifA activity is inhibited directly by interaction with the deuridylylated forms of both GlnK and GlnB under nitrogen-excess conditions. In some bacteria the Nif cluster can be regulated by glnR, which can comprise negative regulation. Regardless of the mechanism, post-translational inhibition of NifA is an important regulator of the nif cluster in most known diazotrophs. In some embodiments, one or more of nifL, amtB, glnK, and glnR can be mutated in the bacterial strains described herein.

Loss of NifL function can remove repression of NifA in nitrogen-limiting conditions. In some embodiments, at least one modification in a gene regulating nitrogen fixation or assimilation results in decreased expression of nifL. In some embodiments, at least one modification in a gene regulating nitrogen fixation or assimilation comprises a deletion of all or a portion of the coding sequence of the nifL gene. In some embodiments, at least one modification in a gene regulating nitrogen fixation or assimilation comprises a deletion of a portion of the coding sequence of the nifL gene. For example, a middle portion of the coding sequence of the nifL gene can be deleted. In some embodiments, the first 30 base pairs and the last 83 base pairs of the nifL coding sequence can be retained and the remaining base pairs can be deleted. In some embodiments, the deleted portion of the nifL coding sequence is replaced by a promoter, e.g., any of the promoters as described herein. For example, the promoter can be the infC gene promoter (PinfC, SEQ ID NO:1), the cspE gene promoter (SEQ ID NO:2 and SEQ ID NO:3), or the ompX gene promoter (Prm5; SEQ ID NO:4). For additional promoters see International Publication No. WO/2019/084059, which is incorporated herein by reference in its entirety. In some embodiments, the promoter has at least about 70%, about 75%, about 80%, about 85%, about 90%, about 95%, about 97%, about 98%, about 99%, or about 100% sequence identity to any one of SEQ ID Nos: 1-4.

| Description | SEQ ID NO | Sequence |
|---|---|---|
| PinfC | 1 | AGCGTCAGGTACCGGTCATGATTCACCGTGCGATTCTCGGTTCCCTGGAGCG CTTCATTGGCATCCTGACCGAAGAGTTCGCTGGCTTCTTCCCAACCTGGATTG CACCAGTGCAGGTAGTGGTCATGAATATTACCGATTCTCAGGCTGAATACGT TAACGAATTGACGCGTAAACTACAAAATGCGGGCATTCGTGTAAAAGCAGA CTTGAGAAATGAGAAGATTGGCTTTAAAATCCGCGAGCACACTTTACGTCGT GTCCCGTATATGTTGGTCTGTGGCGACAAAGAAGTCGAAGCCGGCAAAGTG GCCGTGCGCACCCGTCGCGGGAAAGACCTCGGCAGCATGGACGTAAGTGAA GTGATTGAGAAGCTGCAACAAGAGATTCGCAGCCGCAGTCTTCAACAACTG GAGGAATAAGGTATTAAAGGCGGAAAACGAGTTCAAACGGCACGTCCGAAT CGTATCAATGGCGAGATTCGCGCCCTGGAAGTTCGC |
| cspE promoter | 2 | GCCCGCTGACCGACCAGAACTTCCACCTTGGACTCGGCTATACCCTTGGCGT GACGGCGCGCGATAACTGGGACTACATCCCCATTCCGGTGATCTTACCATTG GCGTCAATAGGTTACGGTCCGGCGACTTTCCAGATGACCTATATTCCCGGCA CCTACAATAACGGTAACGTTTACTTCGCCTGGGCTCGTATACAGTTTTAATTC GCTAAGTCTTAGCAATAAATGAGATAAGCGGTGTGTCTTGTGGAAAAACAA GGACTAAAGCGTTACCCACTAAAAAAGATAGCGACTTTTATCACTTTTTAGC AAAGTTGCACTGGACAAAAGGTACCACAATTGGTGTACTGATACTCGACAC AGCATTAGTGTCGATTTTTCATATAAAGGTAATTTTG |
| cspE promoter | 3 | GCCCGCTGACCGACCAGAACTTCCACCTTGGACTCGGCTATACCCTTGGCGT GACGGCGCGCGATAACTGGGACTACATCCCCATTCCGGTGATCTTACCATTG GCGTCAATAGGTTACGGTCCGGCGACTTTCCAGATGACCTATATTCCCGGCA CCTACAATAACGGTAACGTTTACTTCGCCTGGGCTCGTATACAGTTTTAATTC GCTAAGTCTTAGCAATAAATGAGATAAGCGGTGTGTCTTGTGGAAAAACAA GGACTAAAGCGTTACCCACTAAAAAAGATAGCGACTTTTATCACTTTTTAGC AAAGTTGCACTGGACAAAAGGTACCACAATTGGTGTACTGATACTCGACAC AGCATTAGTGTCGATTTTTCATATAAAGGTAATTTTG |
| Prm5 | 4 | GGACATCATCGCGACAAACAATATTAATACCGGCAACCACACCGGCAATTT ACGAGACTGCGCAGGCATCCTTTCTCCCGTCAATTTCTGTCAAATAAAGTAA AAGAGGCAGTCTACTTGAATTACCCCCGGCTGGTTGAGCGTTTGTTGAAAAA AAGTAACTGAAAAATCCGTAGAATAGCGCCACTCTGATGGTTAATTAACCTA TTCAATTAAGAATTATCTGGATGAATGTGCCATTAAATGCGCAGCATAATGG TGCGTTGTGCGGGAAAACTGCTTTTTTTTGAAAGGGTTGGTCAGTAGCGGAA AC |
| ΔnifL::Prm5 | | ATGACCCTGAATATGATGATGGATGCCGGCGGACATCATCGCGACAAACAA TATTAATACCGGCAACCACACCGGCAATTTACGAGACTGCGCAGGCATCCTT TCTCCCGTCAATTTCTGTCAAATAAAGTAAAGAGGCAGTCTACTTGAATTA CCCCCGGCTGGTTGAGCGTTTGTTGAAAAAAAGTAACTGAAAAATCCGTAG AATAGCGCCACTCTGATGGTTAATTAACCTATTCAATTAAGAATTATCTGGA TGAATGTGCCATTAAATGCGCAGCATAATGGTGCGTTGTGCGGGAAAACTGC TTTTTTTTGAAAGGGTTGGTCAGTAGCGGAAACAACTCACTTCACACCCCGA AGGGGGAAGTTGCCTGACCCTACGATTCCCGCTATTTCATTCACTGACCGGA GGTTCAAAATGACCCAGCGAACCGAGTCGGGTAATACCGTCTGGCGCTTCG ATTTGTCCCAGCAGTTCACTGCGATGCAGCGCATAAGCGTGGTACTCAGCCG GGCGACCGAGGTCGATCAGACGCTCCAGCAAGTGCTGTGCGTATTGCACAA TGACGCCTTTTTGCAGCACGGCATGATCTGTCTGTACGACAGCCAGCAGGCG ATTTTGAATATTGAAGCGTTGCAGGAAGCCGATCAGCAGTTAATCCCCGGCA GCTCGCAAATCCGCTATCGTCCGGGCGAAGGGCTGGTCGGGACGGTGCTTTC GCAGGGCCAATCATTAGTGCTGGCGCGCGTTGCTGACGATCAGCGCTTTCTT GACCGGCTCGGGTTGTATGATTACAACCTGCCGTTTATCGCCGTGCCGCTGA TAGGGCCAGATGCGCAGACTTTCGGTGTGCTGACGGCACAACCCATGGCGC GTTACGAAGAGCGATTACCCGCCTGCACCCGCTTTCTGGAAACGGTCGCTAA CCTGGTCGCGCAAACCGTGCGTTTGATGGCACCACCGGCAGTGCGCCCTTCC CCGCGCGCCGCCATAACACAGGCCGCCAGCCCGAAATCCTGCACGGCCTCA CGCGCATTTGGTTTTGAAAATATGGTCGGTAACAGTCCGGCGATGCGCCAGA CCATGGAGATTATCCGTCAGGTTTCGCGCTGGGACACCACCGTTCTGGTACG |

| Description | SEQ ID NO | Sequence |
|---|---|---|
| | | CGGCGAGAGTGGCACCGGCAAGGAGCTGATTGCCAACGCCATCCACCACCA<br>TTCGCCGCGTGCCGGTGCGCCATTTGTGAAATTCAACTGTGCGGCGCTGCCG<br>GACACACTGCTGGAAAGCGAATTGTTCGGTCACGAGAAAGGGGCATTTACC<br>GGCGCGGTACGCCAGCGTAAAGGCCGTTTTGAGCTGGCCGATGGCGGCACG<br>CTGTTTCTTGACGAGATCGGCGAGAGTAGCGCCTCGTTTCAGGCTAAGCTGC<br>TGCGCATTTTGCAGGAAGGCGAAATGGAACGCGTCGGCGGCGACGAGACAT<br>TGCAAGTGAATGTGCGCATTATTGCCGCGACGAACCGCAATCTTGAAGATGA<br>AGTCCGGCTGGGGCACTTTCGCGAAGATCTCTATTATCGCCTGAATGTGATG<br>CCCATCGCCCTGCCGCCACTACGCGAACGCCAGGAGGACATTGCCGAGCTG<br>GCGCACTTTCTGGTGCGTAAAATCGCCCATAACCAGAGCCGTACGCTGCGCA<br>TTAGCGAGGGCGCTATCCGCCTGCTGATGAGCTACAACTGGCCCGGTAATGT<br>GCGCGAACTGGAAAACTGCCTTGAGCGCTCAGCGGTGATGTCGGAGAACGG<br>TCTGATCGATCGGGATGTGATTTTGTTTAATCATCGCGACCAGCCAGCCAAA<br>CCGCCAGTTATCAGCGTCTCGCATGATGATAACTGGCTCGATAACAACCTTG<br>ACGAGCGCCAGCGGCTGATTGCGGCGCTGGAAAAAGCGGGATGGGTACAAG<br>CCAAAGCCGCGCGCTTGCTGGGGATGACGCCGCGCCAGGTCGCCTATCGTAT<br>TCAGACGATGGATATAACCCTGCCAAGGCTATAA |

(2) GlnE

Decreasing the intracellular glutamine level can prevent the cells from sensing high ammonium levels in the environment. This effect can be achieved by increasing the expression level of glutaminase, an enzyme that converts glutamine into glutamate. In addition, intracellular glutamine can also be reduced by decreasing glutamine synthase (an enzyme that converts ammonia into glutamine). In diazotrophs, fixed ammonia is quickly assimilated into glutamine and glutamate to be used for cellular processes. Disruptions to ammonia assimilation can enable diversion of fixed nitrogen to be exported from the cell as ammonia. The fixed ammonia is predominantly assimilated into glutamine by glutamine synthetase (GS), encoded by glnA, and subsequently into glutamine by glutamine oxoglutarate aminotransferase (GOGAT). In some examples, glnS encodes a glutamine synthetase. GS is regulated post-translationally by GS adenylyl transferase (GlnE), a bi-functional enzyme encoded by glnE that catalyzes both the adenylylation and de-adenylylation of GS through activity of its adenylyltransferase (AT) and adenylyl-removing (AR) domains, respectively. Under nitrogen limiting conditions, glnA is expressed, and GlnE's AR domain de-adenylylates GS, allowing it to be active. Under conditions of nitrogen excess, glnA expression is turned off, and GlnE's AT domain is activated allosterically by glutamine, causing the adenylylation and deactivation of GS.

In some embodiments, modification of glnE can increase ammonium excretion. In some embodiments, a conserved aspartate-amino acid-aspartate (DXD) motif on AR domain of glnE can be changed. In some embodiments, changing a conserved DXD residue on AR domain of glnE can be used to remove de-adenylylation activity from glnE. In some embodiments, a D residue can be replaced on a DXD motif in the AR region of glnE. In some embodiments, the replacement of a D residue on a DXD motif in the AR region of glnE can leave the GlnB binding site intact so as to allow for regulation of adenylation activity while decreasing or preventing AR activity. In some embodiments, strains that can be utilized in this process of increasing ammonium excretion can include, but are not limited to, *Rahnella aquatilis*, *Kosakonia sacchari*, and *Klebsiella variicola* strains.

In some embodiments, at least one modification in a gene regulating nitrogen fixation or assimilation results in decreased adenylyl-removing activity of GlnE. In some embodiments, a modification in a gene regulating nitrogen fixation or assimilation comprises a deletion of a portion of the coding sequence of the glnE gene. For example, in some embodiments, 1290 base pairs following the ATG start codon of the glnE gene are deleted. In some embodiments, a deletion of a portion of the coding sequence of the glnE gene results in decreased adenylyl-removing activity of GlnE. In some embodiments, a modification in a gene regulating nitrogen fixation or assimilation results in a truncated GlnE protein lacking an adenylyl-removing (AR) domain. In some embodiments, the GlnE protein lacking the AR domain has a functional ATase domain.

(3) NtrC

In some embodiments, modification of glnA can be beneficial in increasing ammonium excretion. In some embodiments, modification of NtrC can be beneficial in modifying the level of GlnA protein in the cell. NtrC is the member of the two-component regulatory system NtrB/NtrC, which controls expression of the nitrogen-regulated (ntr) genes in response to nitrogen limitation. Under nitrogen limited conditions, PII signaling proteins initiate a phosphorylation cascade that leads to the phosphorylation of the aspartate (D54) residue of NtrC. The phosphorylated form of NtrC binds upstream of multiple nitrogen metabolism genes it regulates and activates their transcription. Changing aspartate residue to a more negatively charged amino acid residue, glutamate (D54E), led NtrC to behave like phosphorylated and constitutively activated the transcription of its downstream target genes (Klose et al 1993). On the other hand, changing aspartate to alanine (D54A), prohibited phosphorylation of this residue, and hence activation of NtrC, resulting in lack of transcriptional response even under nitrogen limited conditions. In some embodiments, modification of NtrC can be beneficial by preventing the phosphorylization of NtrC. Phosphorylated NtrC can lead to transcriptional activation of glnA. As such, modification of ntrC so as to prevent the phosphorylization of ntrC can be beneficial in decreasing transcription of glnA. In some embodiments, modification of NtrC can be achieved by replacing asparate 54.

In some embodiments of the genetically engineered bacteria described herein, the NtrC binding site upstream of nifA is replaced by a constitutive promoter. This can remove NtrC for transcriptional activation of nifA. In some embodiments, the at least one modification in a gene regulating nitrogen fixation or assimilation comprises a mutation in the coding sequence of the ntrC gene. In some embodiments, at least one modification in a gene regulating nitrogen fixation or assimilation comprises changing the 161st nucleotide of the ntrC coding sequence from A to C (SEQ ID NO:6). In some embodiments, the mutation in the coding sequence of the ntrC gene encode NtrC protein comprising a D54A amino acid substitution. In some embodiments, the mutation in NtrcC results in increased ammonium excretion. In some embodiments, strains that can be utilized in this process of increasing ammonium excretion can include, but are not limited to, *Rahnella aquatilis, Kosakonia sacchari*, and *Klebsiella variicola* strains.

least 400 isolates can be collected in a round of harvest. Soil and plant types reveal the plant phenotype as well as the conditions, which allow for the downstream enrichment of certain phenotypes.

Microbes can be isolated from plant tissues to assess microbial traits. The parameters for processing tissue samples may be varied to isolate different types of associative microbes, such as rhizospheric bacteria, epiphytes, or endophytes. The isolates can be cultured in nitrogen-free media to enrich for bacteria that perform nitrogen fixation. Alternatively, microbes can be obtained from global strain banks.

In planta analytics are performed to assess microbial traits. In some embodiments, the plant tissue can be pro- NtrC Sequence

| Description | SEQ ID NO | Sequence |
| --- | --- | --- |
| Mutated NtrC | 6 | ATGCAACGAGGGATAGCCTGGATCGTTGATGACGATAGCTCCATCCGCTGGGT GCTTGAACGCGCGCTCACCGGAGCCGGCTTGAGCTGCACAACGTTCGAAAGC GGCAATGAGGTGCTAGATGCCCTCACCACCAAAACCCGGATGTACTGCTGTC AGCTATCCGTATGCCGGGAATGGATGGTCTGGCGCTGCTCAAACAGATTAAGC AGCGTCATCCAATGCTTCCGGTCATCATAATGACCGCACATTCCGATCTGGAC GCTGCGGTCAGCGCTTATCAGCAAGGCGCGTTTGATTATCTGCCCAAACCTTT TGATATTGATGAAGCCGTCGCCCTGGTCGACCGGGCGATAAGCCACTATCAGG AGCAGCAACAGCCGCGAAATGCGCCAATAAGCAGCCCAACTGCCGACATCAT CGGCGAAGCGCCGGCAATGCAGGATGTCTTTCGCATTATTGGCCGTTTGTCGC GATCATCCATCAGCGTGCTGATTAATGGCGAATCCGGTACCGGTAAAGAGCTC GTCGCTCACGCCCTGCATCGTCATAGCCCACGTTCAAAAGCGCCGTTTATCGC ACTGAATATGGCGGCAATACCCAAAGACCTGATTGAGTCCGAGCTGTTCGGGC ATGAAAAAGGGGCCTTTACCGGCGCCAATACCGTCCGCCAGGGACGCTTCGA ACAGGCTGACGGCGGCACGCTATTCCTGGATGAAATTGGCGATATGCCGCTTG ATGTCCAGACTCGTCTGCTGCGCGTGCTGGCGGATGGCCAGTTTTATCGCGTG GGCGGTTACGCGCCGGTGAAGGTCGATGTGCGGATCATCGCCGCCACCCACC AGAACCTGGAACAGCGCGTGCAGGAGGGGAAATTCCGTGAAGATTTGTTCCA CCGCCTGAACGTGATCCGGGTGCATTTACCGCCGCTGCGCGAGCGCCGGGAA GATATTCCACGCCTGGCCCGCCATTTTCTGCAGATAGCCGCCCGCGAGCTCGG TGTTGAAGCCAAACAGCTGCATCCGGAAACGGAGACAGCGCTGACACGCCTG GCGTGGCCTGGCAACGTCCGTCAGCTGGAAAACACCTGTCGCTGGCTCACCGT CATGGCCGCCGGCCAGGAGGTACTGACGCAGGATCTGCCGAGCGAACTGTTT GAGACTACGGTTCCGGACAGCCCGACGCAGATGCAGCCCGACAGCTGGGCGA CGCTGCTGGGTCAGTGGGCCGATCGGGCGTTGCGATCCGGTCATCAAAACCTG CTCTCAGAAGCGCAACCCGAAATGGAGCGCACGCTGCTGACGACCGCCCTGC GCCATACCCAGGGGCACAAGCAGGAGGCTGCGCGTCTGCTGGGATGGGGTCG TAATACCCTGACGCGTAAGCTAAAAGAGCTGGGAATGGAGTAG |

Generation of Microbe Populations

Microbes useful in methods and compositions disclosed herein can be obtained by extracting microbes from surfaces or tissues of native plants. Microbes can be obtained by grinding seeds to isolate microbes. Microbes can be obtained by planting seeds in diverse soil samples and recovering microbes from tissues. Additionally, microbes can be obtained by inoculating plants with exogenous microbes and determining which microbes appear in plant tissues. Non-limiting examples of plant tissues may include a seed, seedling, leaf, cutting, plant, bulb, or tuber.

A method of obtaining microbes may be through the isolation of bacteria from soils. Bacteria may be collected from various soil types. In some example, the soil can be characterized by traits such as high or low fertility, levels of moisture, levels of minerals, and various cropping practices. For example, the soil may be involved in a crop rotation where different crops are planted in the same soil in successive planting seasons. The sequential growth of different crops on the same soil may prevent disproportionate depletion of certain minerals. The bacteria can be isolated from the plants growing in the selected soils. The seedling plants can be harvested at 2-6 weeks of growth. For example, at cessed for screening by high throughput processing for DNA and RNA. Additionally, non-invasive measurements can be used to assess plant characteristics, such as colonization. Measurements on wild microbes can be obtained on a plant-by-plant basis. Measurements on wild microbes can also be obtained in the field using medium throughput methods. Measurements can be done successively over time. Model plant system can be used including, but not limited to, *Setaria*.

Microbes in a plant system can be screened via transcriptional profiling of a microbe in a plant system. Examples of screening through transcriptional profiling are using methods of quantitative polymerase chain reaction (qPCR), molecular barcodes for transcript detection, Next Generation Sequencing, and microbe tagging with fluorescent markers. Impact factors can be measured to assess colonization in the greenhouse including, but not limited to, microbiome, abiotic factors, soil conditions, oxygen, moisture, temperature, inoculum conditions, and root localization. Nitrogen fixation can be assessed in bacteria by measuring $^{15}N$ gas/fertilizer (dilution) with IRMS or NanoSIMS as described herein NanoSIMS is high-resolution secondary ion mass spectrometry. The NanoSIMS technique is a way to investigate chemical activity from biological samples. The catalysis of reduction of oxidation reactions that drive the metabolism of microorganisms can be investigated at the cellular, subcellular, molecular and elemental level. NanoSIMS can provide high spatial resolution of greater than 0.1 μm. NanoSIMS can detect the use of isotope tracers such as $^{13}C$, $^{15}N$, and $^{18}O$. Therefore, NanoSIMS can be used to the chemical activity nitrogen in the cell.

One way of enriching a microbe population is according to genotype. For example, a polymerase chain reaction (PCR) assay with a targeted primer or specific primer. Primers designed for the nifH gene can be used to identity diazotrophs because diazotrophs express the nifH gene in the process of nitrogen fixation. A microbial population can also be enriched via single-cell culture-independent approaches and chemotaxis-guided isolation approaches. Alternatively, targeted isolation of microbes can be performed by culturing the microbes on selection media. Premeditated approaches to enriching microbial populations for desired traits can be guided by bioinformatics data and are described herein.

Enriching for Microbes with Nitrogen Fixation Capabilities Using Bioinformatics

Bioinformatic tools can be used to identify and isolate plant growth promoting *rhizobacteria* (PGPRs), which are selected based on their ability to perform nitrogen fixation. Microbes with high nitrogen fixing ability can promote favorable traits in plants. Bioinformatic modes of analysis for the identification of PGPRs include, but are not limited to, genomics, metagenomics, targeted isolation, gene sequencing, transcriptome sequencing, and modeling.

Genomics analysis can be used to identify PGPRs and confirm the presence of mutations with methods of Next Generation Sequencing as described herein and microbe version control.

Metagenomics can be used to identify and isolate PGPR using a prediction algorithm for colonization. Metadata can also be used to identify the presence of an engineered strain in environmental and greenhouse samples.

Transcriptomic sequencing can be used to predict genotypes leading to PGPR phenotypes. Additionally, transcriptomic data is used to identify promoters for altering gene expression. Transcriptomic data can be analyzed in conjunction with the Whole Genome Sequence (WGS) to generate models of metabolism and gene regulatory networks.

Domestication of Microbes

Microbes isolated from nature can undergo a domestication process wherein the microbes are converted to a form that is genetically trackable and identifiable. One way to domesticate a microbe is to engineer it with antibiotic resistance. The process of engineering antibiotic resistance can begin by determining the antibiotic sensitivity in the wild type microbial strain. If the bacteria are sensitive to the antibiotic, then the antibiotic can be a good candidate for antibiotic resistance engineering. Subsequently, an antibiotic resistant gene or a counterselectable suicide vector can be incorporated into the genome of a microbe using recombineering methods. A counterselectable suicide vector may consist of a deletion of the gene of interest, a selectable marker, and the counterselectable marker sacB. Counterselection can be used to exchange native microbial DNA sequences with antibiotic resistant genes. A medium throughput method can be used to evaluate multiple microbes simultaneously allowing for parallel domestication.

Alternative methods of domestication include the use of homing nucleases to prevent the suicide vector sequences from looping out or from obtaining intervening vector sequences.

DNA vectors can be introduced into bacteria via several methods including electroporation and chemical transformations. A standard library of vectors can be used for transformations. An example of a method of gene editing is CRISPR preceded by Cas9 testing to ensure activity of Cas9 in the microbes.

Non-Transgenic Engineering of Microbes

A microbial population with favorable traits can be obtained via directed evolution. Direct evolution is an approach wherein the process of natural selection is mimicked to evolve proteins or nucleic acids towards a user-defined goal. An example of direct evolution is when random mutations are introduced into a microbial population, the microbes with the most favorable traits are selected, and the growth of the selected microbes is continued. The most favorable traits in growth promoting *rhizobacteria* (PGPRs) may be in nitrogen fixation. The method of directed evolution may be iterative and adaptive based on the selection process after each iteration.

Plant growth promoting *rhizobacteria* (PGPRs) with high capability of nitrogen fixation can be generated. The evolution of PGPRs can be carried out via the introduction of genetic variation. Genetic variation can be introduced via polymerase chain reaction mutagenesis, oligonucleotide-directed mutagenesis, saturation mutagenesis, fragment shuffling mutagenesis, homologous recombination, CRISPR/Cas9 systems, chemical mutagenesis, and combinations thereof. These approaches can introduce random mutations into the microbial population. For example, mutants can be generated using synthetic DNA or RNA via oligonucleotide-directed mutagenesis. Mutants can be generated using tools contained on plasmids, which are later cured.

Genes of interest can be identified using libraries from other species with improved traits including, but not limited to, improved PGPR properties, improved colonization of cereals, increased oxygen sensitivity, increased nitrogen fixation, and increased ammonia excretion.

Intrageneric genes can be designed based on these libraries using software such as Geneious or Platypus design software. Mutations can be designed with the aid of machine learning. Mutations can be designed with the aid of a metabolic model. Automated design of the mutation can be done using a la Platypus and will guide RNAs for Cas-directed mutagenesis.

The intra-generic genes can be transferred into the host microbe. Additionally, reporter systems can also be transferred to the microbe. The reporter systems characterize promoters, determine the transformation success, screen mutants, and act as negative screening tools.

The microbes carrying the mutation can be cultured via serial passaging. A microbial colony contains a single variant of the microbe. Microbial colonies are screened with the aid of an automated colony picker and liquid handler. Mutants with gene duplication and increased copy number express a higher genotype of the desired trait.

Selection of Plant Growth Promoting Microbes based on Nitrogen Fixation

The microbial colonies can be screened using various assays to assess nitrogen fixation. One way to measure nitrogen fixation is via a single fermentative assay, which measures nitrogen excretion. An alternative method is the acetylene reduction assay (ARA) with in-line sampling over time. ARA can be performed in high throughput plates of microtube arrays. ARA can be performed with live plants and plant tissues. The media formulation and media oxygen concentration can be varied in ARA assays. Another method of screening microbial variants is by using biosensors. The use of NanoSIMS and Raman microspectroscopy can be used to investigate the activity of the microbes. In some cases, bacteria can also be cultured and expanded using methods of fermentation in bioreactors. The bioreactors are designed to improve robustness of bacteria growth and to decrease the sensitivity of bacteria to oxygen. Medium to high TP plate-based microfermentors are used to evaluate oxygen sensitivity, nutritional needs, nitrogen fixation, and nitrogen excretion. The bacteria can also be co-cultured with competitive or beneficial microbes to elucidate cryptic pathways. Flow cytometry can be used to screen for bacteria that produce high levels of nitrogen using chemical, colorimetric, or fluorescent indicators. The bacteria may be cultured in the presence or absence of a nitrogen source. For example, the bacteria may be cultured with glutamine, ammonia, urea or nitrates.

Guided Microbial Remodeling

Guided microbial remodeling is a method to systematically identify and improve the role of species within the crop microbiome. In some aspects, and according to a particular methodology of grouping/categorization, the method comprises three steps: 1) selection of candidate species by mapping plant-microbe interactions and predicting regulatory networks linked to a particular phenotype, 2) pragmatic and predictable improvement of microbial phenotypes through intra-species crossing of regulatory networks and gene clusters within a microbe's genome, and 3) screening and selection of new microbial genotypes that produce desired crop phenotypes.

To systematically assess the improvement of strains, a model is created that links colonization dynamics of the microbial community to genetic activity by key species. The model is used to predict genetic targets for non-intergeneric genetic remodeling (i.e. engineering the genetic architecture of the microbe in a non-transgenic fashion).

Rational improvement of the crop microbiome may be used to increase soil biodiversity, tune impact of keystone species, and/or alter timing and expression of important metabolic pathways.

To this end, the inventors have developed a platform to identify and improve the role of strains within the crop microbiome. In some aspects, the inventors call this process microbial breeding.

The aforementioned "Guided Microbial Remodeling" process will be further elaborated upon in the Examples, for instance in Example 1, entitled: "Guided Microbial Remodeling—A Platform for the Rational Improvement of Microbial Species for Agriculture."

Serial Passage

Production of bacteria to improve plant traits (e.g., nitrogen fixation) can be achieved through serial passage. The production of these bacteria can be done by selecting plants, which have a particular improved trait that is influenced by the microbial flora, in addition to identifying bacteria and/or compositions that are capable of imparting one or more improved traits to one or more plants. One method of producing a bacteria to improve a plant trait includes the steps of: (a) isolating bacteria from tissue or soil of a first plant; (b) introducing a genetic variation into one or more of the bacteria to produce one or more variant bacteria; (c) exposing a plurality of plants to the variant bacteria; (d) isolating bacteria from tissue or soil of one of the plurality of plants, wherein the plant from which the bacteria is isolated has an improved trait relative to other plants in the plurality of plants; and (e) repeating steps (b) to (d) with bacteria isolated from the plant with an improved trait (step (d)). Steps (b) to (d) can be repeated any number of times (e.g., once, twice, three times, four times, five times, ten times, or more) until the improved trait in a plant reaches a desired level. Further, the plurality of plants can be more than two plants, such as 10 to 20 plants, or 20 or more, 50 or more, 100 or more, 300 or more, 500 or more, or 1000 or more plants.

In addition to obtaining a plant with an improved trait, a bacterial population comprising bacteria comprising one or more genetic variations introduced into one or more genes (e.g., genes regulating nitrogen fixation) is obtained. By repeating the steps described above, a population of bacteria can be obtained that include the most appropriate members of the population that correlate with a plant trait of interest. The bacteria in this population can be identified and their beneficial properties determined, such as by genetic and/or phenotypic analysis. Genetic analysis may occur of isolated bacteria in step (a). Phenotypic and/or genotypic information may be obtained using techniques including: high through-put screening of chemical components of plant origin, sequencing techniques including high throughput sequencing of genetic material, differential display techniques (including DDRT-PCR, and DD-PCR), nucleic acid microarray techniques, RNA-sequencing (Whole Transcriptome Shotgun Sequencing), and qRT-PCR (quantitative real time PCR). Information gained can be used to obtain community profiling information on the identity and activity of bacteria present, such as phylogenetic analysis or microarray-based screening of nucleic acids coding for components of rRNA operons or other taxonomically informative loci. Examples of taxonomically informative loci include 16S rRNA gene, 23S rRNA gene, 5S rRNA gene, 5.8S rRNA gene, 12S rRNA gene, 18S rRNA gene, 28S rRNA gene, gyrB gene, rpoB gene, fusA gene, recA gene, coxl gene, nifD gene. Example processes of taxonomic profiling to determine taxa present in a population are described in US 2014/0155283. Bacterial identification may comprise characterizing activity of one or more genes or one or more signaling pathways, such as genes associated with the nitrogen fixation pathway. Synergistic interactions (where two components, by virtue of their combination, increase a desired effect by more than an additive amount) between different bacterial species may also be present in the bacterial populations.

Genetic Variation—Locations and Sources of Genomic Alteration

The genetic variation may be a gene selected from the group consisting of: nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ. The genetic variation may be a variation in a gene encoding a protein with functionality selected from the group consisting of: glutamine synthetase, glutaminase, glutamine synthetase adenylyltransferase, transcriptional activator, antitranscriptional activator, pyruvate flavodoxin oxidoreductase, flavodoxin, and NAD+-dinitrogenreductase aDP-D-ribosyltransferase. The genetic variation may be a mutation that results in one or more of: increased expression or activity of NifA or glutaminase; decreased expression or activity of NifL, NtrB, glutamine synthetase, GlnB, GlnK, DraT, AmtB; decreased adenylylremoving activity of GlnE; or decreased uridylyl-removing activity of GlnD. The genetic variation may be a variation in a gene selected from the group consisting of: bcsii, bcsiii, yjbE, fhaB, pehA, otsB, treZ, glsA2, and combinations thereof. In some embodiments, a genetic variation may be a variation in any of the genes described throughout this disclosure.

Introducing a genetic variation may comprise insertion and/or deletion of one or more nucleotides at a target site, such as 1, 2, 3, 4, 5, 10, 25, 50, 100, 250, 500, or more nucleotides. The genetic variation introduced into one or more bacteria of the methods disclosed herein may be a knock-out mutation (e.g. deletion of a promoter, insertion or deletion to produce a premature stop codon, deletion of an entire gene), or it may be elimination or abolishment of activity of a protein domain (e.g. point mutation affecting an active site, or deletion of a portion of a gene encoding the relevant portion of the protein product), or it may alter or abolish a regulatory sequence of a target gene. One or more regulatory sequences may also be inserted, including heterologous regulatory sequences and regulatory sequences found within a genome of a bacterial species or genus corresponding to the bacteria into which the genetic variation is introduced.

Moreover, regulatory sequences may be selected based on the expression level of a gene in a bacterial culture or within a plant tissue. The genetic variation may be a pre-determined genetic variation that is specifically introduced to a target site. The genetic variation may be a random mutation within the target site. The genetic variation may be an insertion or deletion of one or more nucleotides. In some cases, a plurality of different genetic variations (e.g. 2, 3, 4, 5, 10, or more) are introduced into one or more of the isolated bacteria before exposing the bacteria to plants for assessing trait improvement. The plurality of genetic variations can be any of the above types, the same or different types, and in any combination. In some cases, a plurality of different genetic variations are introduced serially, introducing a first genetic variation after a first isolation step, a second genetic variation after a second isolation step, and so forth so as to accumulate a plurality of genetic variations in bacteria imparting progressively improved traits on the associated plants.

Genetic Variation—Methods of Introducing Genomic Alteration

In general, the term "genetic variation" refers to any change introduced into a polynucleotide sequence relative to a reference polynucleotide, such as a reference genome or portion thereof, or reference gene or portion thereof. A genetic variation may be referred to as a "mutation," and a sequence or organism comprising a genetic variation may be referred to as a "genetic variant" or "mutant". Genetic variations can have any number of effects, such as the increase or decrease of some biological activity, including gene expression, metabolism, and cell signaling. Genetic variations can be specifically introduced to a target site, or introduced randomly. A variety of molecular tools and methods are available for introducing genetic variation. For example, genetic variation can be introduced via polymerase chain reaction mutagenesis, oligonucleotide-directed mutagenesis, saturation mutagenesis, fragment shuffling mutagenesis, homologous recombination, recombineering, lambda red mediated recombination, CRISPR/Cas9 systems, chemical mutagenesis, and combinations thereof. Chemical methods of introducing genetic variation include exposure of DNA to a chemical mutagen, e.g., ethyl methanesulfonate (EMS), methyl methanesulfonate (MMS), N-nitrosourea (EN U), N-methyl-N-nitro-N'-nitrosoguanidine, 4-nitroquinoline N-oxide, diethylsulfate, benzopyrene, cyclophosphamide, bleomycin, triethylmelamine, acrylamide monomer, nitrogen mustard, vincristine, diepoxyalkanes (for example, diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, γ-irradiation, X-rays, and fast neutron bombardment. Genetic variation can also be introduced into a nucleic acid using, e.g., trimethylpsoralen with ultraviolet light. Random or targeted insertion of a mobile DNA element, e.g., a transposable element, is another suitable method for generating genetic variation. Genetic variations can be introduced into a nucleic acid during amplification in a cell-free in vitro system, e.g., using a polymerase chain reaction (PCR) technique such as error-prone PCR. Genetic variations can be introduced into a nucleic acid in vitro using DNA shuffling techniques (e.g., exon shuffling, domain swapping, and the like). Genetic variations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 1 6, PMS 1 2, MLH 1, GTBP, ERCC-1, and the like). Example descriptions of various methods for introducing genetic variations are provided in e.g., Stemple (2004) Nature 5:1-7; Chiang et al. (1993) PCR Methods Appl 2(3): 210-217; Stemmer (1994) Proc. Natl. Acad. Sci. USA 91:10747-10751; and U.S. Pat. Nos. 6,033,861, and 6,773,900.

Genetic variations introduced into microbes may be classified as transgenic, cisgenic, intragenomic, intrageneric, intergeneric, synthetic, evolved, rearranged, or SNPs.

Genetic variation may be introduced into numerous metabolic pathways within microbes to elicit improvements in the traits described above. Representative pathways include sulfur uptake pathways, glycogen biosynthesis, the glutamine regulation pathway, the molybdenum uptake pathway, the nitrogen fixation pathway, ammonia assimilation, ammonia excretion or secretion, Nitrogen uptake, glutamine biosynthesis, colonization pathways, annamox, phosphate solubilization, organic acid transport, organic acid production, agglutinins production, reactive oxygen radical scavenging genes, Indole Acetic Acid biosynthesis, trehalose biosynthesis, plant cell wall degrading enzymes or pathways, root attachment genes, exopolysaccharide secretion, glutamate synthase pathway, iron uptake pathways, siderophore pathway, chitinase pathway, ACC deaminase, glutathione biosynthesis, phosphorous signaling genes, quorum quenching pathway, cytochrome pathways, hemoglobin pathway, bacterial hemoglobin-like pathway, small RNA rsmZ, rhizobitoxine biosynthesis, lapA adhesion protein, AHL quorum sensing pathway, phenazine biosynthesis, cyclic lipopeptide biosynthesis, and antibiotic production.

CRISPR/Cas9 (Clustered regularly interspaced short palindromic repeats)/CRISPRassociated (Cas) systems can be used to introduce desired mutations. CRISPR/Cas9 provide bacteria and archaea with adaptive immunity against viruses and plasmids by using CRISPR RNAs (crRNAs) to guide the silencing of invading nucleic acids. The Cas9 protein (or functional equivalent and/or variant thereof, i.e., Cas9-like protein) naturally contains DNA endonuclease activity that depends on the association of the protein with two naturally occurring or synthetic RNA molecules called crRNA and tracrRNA (also called guide RNAs). In some cases, the two molecules are covalently link to form a single molecule (also called a single guide RNA ("sgRNA"). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence. If the Cas9 or Cas9-like protein retains its natural enzymatic function, it will cleave target DNA to create a double-stranded break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Further exemplary descriptions of CRISPR systems for introducing genetic variation can be found in, e.g. U.S. Pat. No. 8,795,965.

As a cyclic amplification technique, polymerase chain reaction (PCR) mutagenesis uses mutagenic primers to introduce desired mutations. PCR is performed by cycles of denaturation, annealing, and extension. After amplification by PCR, selection of mutated DNA and removal of parental plasmid DNA can be accomplished by: 1) replacement of dCTP by hydroxymethylated-dCTP during PCR, followed by digestion with restriction enzymes to remove non-hydroxymethylated parent DNA only; 2) simultaneous mutagenesis of both an antibiotic resistance gene and the studied gene changing the plasmid to a different antibiotic resistance, the new antibiotic resistance facilitating the selection of the desired mutation thereafter; 3) after introducing a desired mutation, digestion of the parent methylated template DNA by restriction enzyme Dpn1 which cleaves only methylated DNA, by which the mutagenized unmethylated chains are recovered; or 4) circularization of the mutated PCR products in an additional ligation reaction to increase the transformation efficiency of mutated DNA. Further description of exemplary methods can be found in e.g. U.S. Pat. Nos. 7,132,265, 6,713,285, 6,673,610, 6,391,548, 5,789,166, 5,780,270, 5,354,670, 5,071,743, and US 2010/0267147.

Oligonucleotide-directed mutagenesis, also called site-directed mutagenesis, typically utilizes a synthetic DNA primer. This synthetic primer contains the desired mutation and is complementary to the template DNA around the mutation site so that it can hybridize with the DNA in the gene of interest. The mutation may be a single base change (a point mutation), multiple base changes, deletion, or insertion, or a combination of these. The single-strand primer is then extended using a DNA polymerase, which copies the rest of the gene. The gene thus copied contains the mutated site, and may then be introduced into a host cell as a vector and cloned. Finally, mutants can be selected by DNA sequencing to check that they contain the desired mutation.

Genetic variations can be introduced using error-prone PCR. In this technique the gene of interest is amplified using a DNA polymerase under conditions that are deficient in the fidelity of replication of sequence. The result is that the amplification products contain at least one error in the sequence. When a gene is amplified and the resulting product(s) of the reaction contain one or more alterations in sequence when compared to the template molecule, the resulting products are mutagenized as compared to the template. Another means of introducing random mutations is exposing cells to a chemical mutagen, such as nitrosoguanidine or ethyl methanesulfonate (Nestmann, Mutat Res 1975 June; 28(3):323-30), and the vector containing the gene is then isolated from the host.

Saturation mutagenesis is another form of random mutagenesis, in which one tries to generate all or nearly all possible mutations at a specific site, or narrow region of a gene. In a general sense, saturation mutagenesis is comprised of mutagenizing a complete set of mutagenic cassettes (wherein each cassette is, for example, 1-500 bases in length) in defined polynucleotide sequence to be mutagenized (wherein the sequence to be mutagenized is, for example, from 15 to 100,000 bases in length). Therefore, a group of mutations (e.g. ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Fragment shuffling mutagenesis, also called DNA shuffling, is a way to rapidly propagate beneficial mutations. In an example of a shuffling process, DNAse is used to fragment a set of parent genes into pieces of e.g. about 50-100 bp in length. This is then followed by a polymerase chain reaction (PCR) without primers—DNA fragments with sufficient overlapping homologous sequence will anneal to each other and are then be extended by DNA polymerase. Several rounds of this PCR extension are allowed to occur, after some of the DNA molecules reach the size of the parental genes. These genes can then be amplified with another PCR, this time with the addition of primers that are designed to complement the ends of the strands. The primers may have additional sequences added to their 5' ends, such as sequences for restriction enzyme recognition sites needed for ligation into a cloning vector. Further examples of shuffling techniques are provided in US 2005/0266541.

Homologous recombination mutagenesis involves recombination between an exogenous DNA fragment and the targeted polynucleotide sequence. After a double-stranded break occurs, sections of DNA around the 5' ends of the break are cut away in a process called resection. In the strand invasion step that follows, an overhanging 3' end of the broken DNA molecule then "invades" a similar or identical DNA molecule that is not broken. The method can be used to delete a gene, remove exons, add a gene, and introduce point mutations. Homologous recombination mutagenesis can be permanent or conditional.

Typically, a recombination template is also provided. A recombination template may be a component of another vector, contained in a separate vector, or provided as a separate polynucleotide. In some embodiments, a recombination template is designed to serve as a template in homologous recombination, such as within or near a target sequence nicked or cleaved by a site-specific nuclease. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence.

When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence. Non-limiting examples of site-directed nucleases useful in methods of homologous recombination include zinc finger nucleases, CRISPR nucleases, TALE nucleases, and meganuclease. For a further description of the use of such nucleases, see e.g. U.S. Pat. No. 8,795,965 and US 2014/0301990.

Mutagens that create primarily point mutations and short deletions, insertions, transversions, and/or transitions, including chemical mutagens or radiation, may be used to create genetic variations. Mutagens include, but are not limited to, ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)amino-propylamino]acridine dihydrochloride and formaldehyde.

Introducing genetic variation may be an incomplete process, such that some bacteria in a treated population of bacteria carry a desired mutation while others do not. In some cases, it is desirable to apply a selection pressure so as to enrich for bacteria carrying a desired genetic variation. Traditionally, selection for successful genetic variants involved selection for or against some functionality imparted or abolished by the genetic variation, such as in the case of inserting antibiotic resistance gene or abolishing a metabolic activity capable of converting a non-lethal compound into a lethal metabolite. It is also possible to apply a selection pressure based on a polynucleotide sequence itself, such that only a desired genetic variation need be introduced (e.g., without also requiring a selectable marker). In this case, the selection pressure can comprise cleaving genomes lacking the genetic variation introduced to a target site, such that selection is effectively directed against the reference sequence into which the genetic variation is sought to be introduced. Typically, cleavage occurs within 100 nucleotides of the target site (e.g. within 75, 50, 25, 10, or fewer nucleotides from the target site, including cleavage at or within the target site).

Cleaving may be directed by a site-specific nuclease selected from the group consisting of a Zinc Finger nuclease, a CRISPR nuclease, a TALE nuclease (TALEN), and a meganuclease. Such a process is similar to processes for enhancing homologous recombination at a target site, except that no template for homologous recombination is provided. As a result, bacteria lacking the desired genetic variation are more likely to undergo cleavage that, left unrepaired, results in cell death. Bacteria surviving selection may then be isolated for use in exposing to plants for assessing conferral of an improved trait.

A CRISPR nuclease may be used as the site-specific nuclease to direct cleavage to a target site. An improved selection of mutated microbes can be obtained by using Cas9 to kill nonmutated cells. Plants are then inoculated with the mutated microbes to re-confirm symbiosis and create evolutionary pressure to select for efficient symbionts. Microbes can then be re-isolated from plant tissues. CRISPR nuclease systems employed for selection against non-variants can employ similar elements to those described above with respect to introducing genetic variation, except that no template for homologous recombination is provided. Cleavage directed to the target site thus enhances death of affected cells.

Other options for specifically inducing cleavage at a target site are available, such as zinc finger nucleases, TALE nuclease (TALEN) systems, and meganuclease. Zinc-finger nucleases (ZFNs) are artificial DNA endonucleases generated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double stranded breaks. Transcription activator-like effector nucleases (TALENs) are artificial DNA endonucleases generated by fusing a TAL (Transcription activator-like) effector DNA binding domain to a DNA cleavage domain. TALENS can be quickly engineered to bind practically any desired DNA sequence and when introduced into a cell, TALENs can be used to edit target DNA in the cell (e.g., the cell's genome) by inducing double strand breaks. Meganucleases (homing endonuclease) are endodeoxyribonucleases characterized by a large recognition site (doublestranded DNA sequences of 12 to 40 base pairs. Meganucleases can be used to replace, eliminate or modify sequences in a highly targeted way. By modifying their recognition sequence through protein engineering, the targeted sequence can be changed.

Genetic Variation—Methods of Identification

The microbes of the present disclosure may be identified by one or more genetic modifications or alterations, which have been introduced into said microbe. One method by which said genetic modification or alteration can be identified is via reference to a SEQ ID NO that contains a portion of the microbe's genomic sequence that is sufficient to identify the genetic modification or alteration.

Further, in the case of microbes that have not had a genetic modification or alteration (e.g. a wild type, WT) introduced into their genomes, the disclosure can utilize 16S nucleic acid sequences to identify said microbes. A 16S nucleic acid sequence is an example of a "molecular marker" or "genetic marker," which refers to an indicator that is used in methods for visualizing differences in characteristics of nucleic acid sequences. Examples of other such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Markers further include polynucleotide sequences encoding 16S or 18S rRNA, and internal transcribed spacer (ITS) sequences, which are sequences found between small-subunit and large-subunit rRNA genes that have proven to be especially useful in elucidating relationships or distinctions when compared against one another. Furthermore, the disclosure utilizes unique sequences found in genes of interest (e.g. nifH,D,K,L,A, glnE, amtB, etc.) to identify microbes disclosed herein.

Improvement of Traits

Methods of the present disclosure may be employed to introduce or improve one or more of a variety of desirable traits. Examples of traits that may introduced or improved include: root biomass, root length, height, shoot length, leaf number, water use efficiency, overall biomass, yield, fruit size, grain size, photosynthesis rate, tolerance to drought, heat tolerance, salt tolerance, resistance to nematode stress, resistance to a fungal pathogen, resistance to a bacterial pathogen, resistance to a viral pathogen, level of a metabolite, and proteome expression. The desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the improved traits) grown under identical conditions.

A preferred trait to be introduced or improved is nitrogen fixation, as described herein. A second preferred trait to be introduced or improved is colonization potential, as described herein. In some cases, a plant resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference agricultural plant grown under the same conditions in the soil. In additional examples, a plant resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least about 100%, at least about 200%, at least about 300%, at least about 400% or greater than a reference agricultural plant grown under similar conditions in the soil.

The trait to be improved may be assessed under conditions including the application of one or more biotic or abiotic stressors. Examples of stressors include abiotic stresses (such as heat stress, salt stress, drought stress, cold stress, and low nutrient stress) and biotic stresses (such as nematode stress, insect herbivory stress, fungal pathogen stress, bacterial pathogen stress, and viral pathogen stress).

The trait improved by methods and compositions of the present disclosure may be nitrogen fixation, including in a plant not previously capable of nitrogen fixation. In some cases, bacteria isolated according to a method described herein produce 1% or more (e.g. 2%, 3%, 4%, 5%, 6%, 7%, 8%, 9%, 10%, 15%, 20%, or more) of a plant's nitrogen, which may represent an increase in nitrogen fixation capability of at least 2-fold (e.g. 3-fold, 4-fold, 5-fold, 6-fold, 7-fold, 8-fold, 9-fold, 10-fold, 20-fold, 50-fold, 100-fold, 1000-fold, or more) as compared to bacteria isolated from the first plant before introducing any genetic variation. In some cases, the bacteria produce 5% or more of a plant's nitrogen. The desired level of nitrogen fixation may be achieved after repeating the steps of introducing genetic variation, exposure to a plurality of plants, and isolating bacteria from plants with an improved trait one or more times (e.g. 1, 2, 3, 4, 5, 10, 15, 25, or more times). In some cases, enhanced levels of nitrogen fixation are achieved in the presence of fertilizer supplemented with glutamine, ammonia, or other chemical source of nitrogen. Methods for assessing degree of nitrogen fixation are known, examples of which are described herein.

Microbe breeding is a method to systematically identify and improve the role of species within the crop microbiome. The method comprises three steps: 1) selection of candidate species by mapping plant-microbe interactions and predicting regulatory networks linked to a particular phenotype, 2) pragmatic and predictable improvement of microbial phenotypes through intraspecies crossing of regulatory networks and gene clusters, and 3) screening and selection of new microbial genotypes that produce desired crop phenotypes. To systematically assess the improvement of strains, a model is created that links colonization dynamics of the microbial community to genetic activity by key species. The model is used to predict genetic targets for breeding and improve the frequency of selecting improvements in microbiome-encoded traits of agronomic relevance.

Bacterial Species

Microbes useful in the methods and compositions disclosed herein may be obtained from any source. In some cases, microbes may be bacteria, archaea, protozoa or fungi. The microbes of this disclosure may be nitrogen fixing microbes, for example a nitrogen fixing bacteria, nitrogen fixing archaea, nitrogen fixing fungi, nitrogen fixing yeast, or nitrogen fixing protozoa. Microbes useful in the methods and compositions disclosed herein may be spore forming microbes, for example spore forming bacteria. In some cases, bacteria useful in the methods and compositions disclosed herein may be Gram positive bacteria or Gram negative bacteria. In some cases, the bacteria may be an endospore forming bacteria of the Firmicute phylum. In some cases, the bacteria may be a diazotroph. In some cases, the bacteria may not be a diazotroph.

The methods and compositions of this disclosure may be used with an archaea, such as, for example, *Methanothermobacter thermoautotrophicus*.

In some cases, bacteria which may be useful include, but are not limited to, *Agrobacterium radiobacter, Bacillus acidocaldarius, Bacillus acidoterrestris, Bacillus agri, Bacillus aizawai, Bacillus albolactis, Bacillus alcalophilus, Bacillus alvei, Bacillus aminoglucosidicus, Bacillus aminovorans, Bacillus amylolyticus* (also known as *Paenibacillus amylolyticus*) *Bacillus amyloliquefaciens, Bacillus aneurinolyticus, Bacillus atrophaeus, Bacillus azotoformans, Bacillus badius, Bacillus cereus* (synonyms: *Bacillus endorhythmos, Bacillus medusa*), *Bacillus chitinosporus, Bacillus circulans, Bacillus coagulans, Bacillus endoparasiticus Bacillus fastidiosus, Bacillus firmus, Bacillus kurstaki, Bacillus lacticola, Bacillus lactimorbus, Bacillus lactis, Bacillus laterosporus* (also known as *Brevibacillus laterosporus*), *Bacillus lautus, Bacillus lentimorbus, Bacillus lentus, Bacillus licheniformis, Bacillus maroccanus, Bacillus megaterium, Bacillus metiens, Bacillus mycoides, Bacillus natto, Bacillus nematocida, Bacillus nigrificans, Bacillus nigrum, Bacillus pantothenticus, Bacillus popillae, Bacillus psychrosaccharolyticus, Bacillus pumilus, Bacillus siamensis, Bacillus smithii, Bacillus sphaericus, Bacillus subtilis, Bacillus thuringiensis, Bacillus uniflagellatus, Bradyrhizobium japonicum, Brevibacillus brevis Brevibacillus laterosporus* (formerly *Bacillus laterosporus*), *Chromobacterium subtsugae, Delftia acidovorans, Lactobacillus acidophilus, Lysobacter antibioticus, Lysobacter enzymogenes, Paenibacillus alvei, Paenibacillus polymyxa, Paenibacillus popilliae* (formerly *Bacillus popilliae*), *Pantoea agglomerans, Pasteuria penetrans* (formerly *Bacillus penetrans*), *Pasteuria usgae, Pectobacterium carotovorum* (formerly *Erwinia carotovora*), *Pseudomonas aeruginosa, Pseudomonas aureofaciens, Pseudomonas cepacia* (formerly known as *Burkholderia cepacia*), *Pseudomonas chlororaphis,*

*Pseudomonas fluorescens, Pseudomonas proradix, Pseudomonas putida, Pseudomonas syringae, Serratia entomophila, Serratia marcescens, Streptomyces colombiensis, Streptomyces galbus, Streptomyces goshikiensis, Streptomyces griseoviridis, Streptomyces lavendulae, Streptomyces prasinus, Streptomyces saraceticus, Streptomyces venezuelae, Xanthomonas campestris, Xenorhabdus luminescens, Xenorhabdus nematophila, Rhodococcus globerulus* AQ719 (NRRL Accession No. B-21663), *Bacillus* sp. AQ175 (ATCC Accession No. 55608), *Bacillus* sp. AQ 177 (ATCC Accession No. 55609), *Bacillus* sp. AQ178 (ATCC Accession No. 53522), and *Streptomyces* sp. strain NRRL Accession No. B-30145. In some cases the bacterium may be *Azotobacter chroococcum, Methanosarcina barkeri, Klesiella pneumoniae, Azotobacter vinelandii, Rhodobacter spharoides, Rhodobacter capsulatus, Rhodobcter palustris, Rhodosporillum rubrum, Rhizobium leguminosarum* or *Rhizobium etli.*

In some cases the bacterium may be a species of *Clostridium*, for example *Clostridium pasteurianum, Clostridium beijerinckii, Clostridium perfringens, Clostridium tetani, Clostridium acetobutylicum.*

In some cases, bacteria used with the methods and compositions of the present disclosure may be cyanobacteria. Examples of cyanobacterial genuses include *Anabaena* (for example *Anagaena* sp. PCC7120), *Nostoc* (for example *Nostoc punctiforme*), or *Synechocystis* (for example *Synechocystis* sp. PCC6803).

In some cases, bacteria used with the methods and compositions of the present disclosure may belong to the phylum Chlorobi, for example *Chlorobium tepidum.*

In some cases, microbes used with the methods and compositions of the present disclosure may comprise a gene homologous to a known NifH gene. Sequences of known NifH genes may be found in, for example, the Zehr lab NifH database, (wwwzehr.pmc.ucsc.edu/nifH_Database_Public/, Apr. 4, 2014), or the Buckley lab NifH database (www.css.cornell.edu/faculty/buckley/nifh.htm, and Gaby, John Christian, and Daniel H. Buckley. "A comprehensive aligned nifH gene database: a multipurpose tool for studies of nitrogen-fixing bacteria." *Database* 2014 (2014): bau001). In some cases, microbes used with the methods and compositions of the present disclosure may comprise a sequence which encodes a polypeptide with at least 60%, 70%, 80%, 85%, 90%, 95%, 96%, 96%, 98%, 99% or more than 99% sequence identity to a sequence from the Zehr lab NifH database, (wwwzehr.pmc.ucsc.edu/nifH_Database_Public/, Apr. 4, 2014). In some cases, microbes used with the methods and compositions of the present disclosure may comprise a sequence which encodes a polypeptide with at least 60%, 70%, 80%, 85%, 90%, 95%, 96%, 96%, 98%, 99% or more than 99% sequence identity to a sequence from the Buckley lab NifH database, (Gaby, John Christian, and Daniel H. Buckley. "A comprehensive aligned nifH gene database: a multipurpose tool for studies of nitrogen-fixing bacteria." *Database* 2014 (2014): bau001).

Microbes useful in the methods and compositions disclosed herein can be obtained by extracting microbes from surfaces or tissues of native plants; grinding seeds to isolate microbes; planting seeds in diverse soil samples and recovering microbes from tissues; or inoculating plants with exogenous microbes and determining which microbes appear in plant tissues. Non-limiting examples of plant tissues include a seed, seedling, leaf, cutting, plant, bulb, tuber, root, and rhizomes. In some cases, bacteria are isolated from a seed. The parameters for processing samples may be varied to isolate different types of associative microbes, such as rhizospheric, epiphytes, or endophytes. Bacteria may also be sourced from a repository, such as environmental strain collections, instead of initially isolating from a first plant. The microbes can be genotyped and phenotyped, via sequencing the genomes of isolated microbes; profiling the composition of communities in planta; characterizing the transcriptomic functionality of communities or isolated microbes; or screening microbial features using selective or phenotypic media (e.g., nitrogen fixation or phosphate solubilization phenotypes). Selected candidate strains or populations can be obtained via sequence data; phenotype data; plant data (e.g., genome, phenotype, and/or yield data); soil data (e.g., pH, N/P/K content, and/or bulk soil biotic communities); or any combination of these.

The bacteria and methods of producing bacteria described herein may apply to bacteria able to self-propagate efficiently on the leaf surface, root surface, or inside plant tissues without inducing a damaging plant defense reaction, or bacteria that are resistant to plant defense responses. The bacteria described herein may be isolated by culturing a plant tissue extract or leaf surface wash in a medium with no added nitrogen. However, the bacteria may be unculturable, that is, not known to be culturable or difficult to culture using standard methods known in the art. The bacteria described herein may be an endophyte or an epiphyte or a bacterium inhabiting the plant rhizosphere (rhizospheric bacteria). The bacteria obtained after repeating the steps of introducing genetic variation, exposure to a plurality of plants, and isolating bacteria from plants with an improved trait one or more times (e.g. 1, 2, 3, 4, 5, 10, 15, 25, or more times) may be endophytic, epiphytic, or rhizospheric. Endophytes are organisms that enter the interior of plants without causing disease symptoms or eliciting the formation of symbiotic structures, and are of agronomic interest because they can enhance plant growth and improve the nutrition of plants (e.g., through nitrogen fixation). The bacteria can be a seed-borne endophyte. Seed-borne endophytes include bacteria associated with or derived from the seed of a grass or plant, such as a seed-borne bacterial endophyte found in mature, dry, undamaged (e.g., no cracks, visible fungal infection, or prematurely germinated) seeds. The seed-borne bacterial endophyte can be associated with or derived from the surface of the seed; alternatively, or in addition, it can be associated with or derived from the interior seed compartment (e.g., of a surface-sterilized seed). In some cases, a seed-borne bacterial endophyte is capable of replicating within the plant tissue, for example, the interior of the seed. Also, in some cases, the seed-borne bacterial endophyte is capable of surviving desiccation.

The bacterial isolated according to methods of the disclosure, or used in methods or compositions of the disclosure, can comprise a plurality of different bacterial taxa in combination. By way of example, the bacteria may include Proteobacteria (such as *Pseudomonas, Enterobacter, Stenotrophomonas, Burkholderia, Rhizobium, Herbaspirillum, Pantoea, Serratia, Rahnella, Azospirillum, Azorhizobium, Azotobacter, Duganella, Delftia, Bradyrhizobiun, Sinorhizobium* and *Halomonas*), Firmicutes (such as *Bacillus, Paenibacillus, Lactobacillus, Mycoplasma*, and *Acetabacterium*), and Actinobacteria (such as *Streptomyces, Rhodacoccus, Microbacterium*, and *Curtobacterium*). The bacteria used in methods and compositions of this disclosure may include nitrogen fixing bacterial consortia of two or more species. In some cases, one or more bacterial species of the bacterial consortia may be capable of fixing nitrogen. In some cases, one or more species of the bacterial consortia may facilitate or enhance the ability of other bacteria to fix nitrogen. The bacteria which fix nitrogen and the bacteria which enhance the ability of other bacteria to fix nitrogen may be the same or different. In some examples, a bacterial strain may be able to fix nitrogen when in combination with a different bacterial strain, or in a certain bacterial consortia, but may be unable to fix nitrogen in a monoculture. Examples of bacterial genuses which may be found in a nitrogen fixing bacterial consortia include, but are not limited to, *Herbaspirillum, Azospirillum, Enterobacter*, and *Bacillus*.

Bacteria that can be produced by the methods disclosed herein include *Azotobacter* sp., *Bradyrhizobium* sp., *Klebsiella* sp., and *Sinorhizobium* sp. In some cases, the bacteria may be selected from the group consisting of: *Azotobacter vinelandii, Bradyrhizobium japonicum, Klebsiella pneumoniae*, and *Sinorhizobium meliloti*. In some cases, the bacteria may be of the genus *Enterobacter* or *Rahnella*. In some cases, the bacteria may be of the genus *Frankia*, or *Clostridium*. Examples of bacteria of the genus *Clostridium* include, but are not limited to, *Clostridium acetobutilicum, Clostridium pasteurianum, Clostridium beijerinckii, Clostridium perfringens*, and *Clostridium tetani*. In some cases, the bacteria may be of the genus *Paenibacillus*, for example *Paenibacillus azotofixans, Paenibacillus borealis, Paenibacillus durus, Paenibacillus macerans, Paenibacillus polymyxa, Paenibacillus alvei, Paenibacillus amylolyticus, Paenibacillus campinasensis, Paenibacillus chibensis, Paenibacillus glucanolyticus, Paenibacillus illinoisensis, Paenibacillus larvae* subsp. *Larvae, Paenibacillus larvae* subsp. *Pulvifaciens, Paenibacillus lautus, Paenibacillus macerans, Paenibacillus macquariensis, Paenibacillus macquariensis, Paenibacillus pabuli, Paenibacillus peoriae*, or *Paenibacillus polymyxa*.

In some examples, bacteria isolated according to methods of the disclosure can be a member of one or more of the following taxa: *Achromobacter, Acidithiobacillus, Acidovorax, Acidovoraz, Acinetobacter, Actinoplanes, Adlercreutzia, Aerococcus, Aeromonas, Afipia, Agromyces, Ancylobacter, Arthrobacter, Atopostipes, Azospirillum, Bacillus, Bdellovibrio, Beijerinckia, Bosea, Bradyrhizobium, Brevibacillus, Brevundimonas, Burkholderia, Candidatus Haloredivivus, Caulobacter, Cellulomonas, Cellvibrio, Chryseobacterium, Citrobacter, Clostridium, Coraliomargarita, Corynebacterium, Cupriavidus, Curtobacterium, Curvibacter, Deinococcus, Delftia, Desemzia, Devosia, Dokdonella, Dyella, Enhydrobacter, Enterobacter, Enterococcus, Erwinia, Escherichia, Escherichia/Shigella, Exiguobacterium, Ferroglobus, Filimonas, Finegoldia, Flavisolibacter, Flavobacterium, Frigoribacterium, Gluconacetobacter, Hafnia, Halobaculum, Halomonas, Halosimplex, Herbaspirillum, Hymenobacter, Klebsiella, Kocuria, Kosakonia, Lactobacillus, Leclercia, Lentzea, Luteibacter, Luteimonas, Massilia, Mesorhizobium, Methylobacterium, Microbacterium, Micrococcus, Microvirga, Mycobacterium, Neisseria, Nocardia, Oceanibaculum, Ochrobactrum, Okibacterium, Oligotropha, Oryzihumus, Oxalophagus, Paenibacillus, Panteoa, Pantoea, Pelomonas, Perlucidibaca, Plantibacter, Polynucleobacter, Propionibacterium, Propioniciclava, Pseudoclavibacter, Pseudomonas, Pseudonocardia, Pseudoxanthomonas, Psychrobacter, Rahnella, Ralstonia, Rheinheimera, Rhizobium, Rhodococcus, Rhodopseudomonas, Roseateles, Ruminococcus, Sebaldella, Sediminibacillus, Sediminibacterium, Serratia, Shigella, Shinella, Sinorhizobium, Sinosporangium, Sphingobacterium, Sphingomonas, Sphingopyxis, Sphingosinicella, Staphylococcus, 25 Stenotrophomonas, Strenotrophomonas, Streptococcus, Streptomyces, Stygiolobus, Sulfurisphaera, Tatumella, Tepidimonas, Thermomonas, Thiobacillus, Variovorax*, WPS-2 genera incertae *sedis, Xanthomonas*, and *Zimmermannella*.

In some cases, a bacterial species selected from at least one of the following genera are utilized: *Enterobacter, Klebsiella, Kosakonia*, and *Rahnella*. In some cases, a combination of bacterial species from the following genera are utilized: *Enterobacter, Klebsiella, Kosakonia*, and *Rahnella*. In some cases, the species utilized can be one or more of: *Enterobacter sacchari, Klebsiella variicola, Kosakonia sacchari*, and *Rahnella aquatilis*.

In some cases, a Gram positive microbe may have a Molybdenum-Iron nitrogenase system comprising: nifH, nifD, nifK, nifB, nifE, nifty, nifX, hesA, nifV, nifW, nifU, nifS, nifI1, and nifI2. In some cases, a Gram positive microbe may have a vanadium nitrogenase system comprising: vnfDG, vnfK, vnfE, vnfN, vupC, vupB, vupA, vnfr, vnfR1, vnfH, vnfR2, vnfA (transcriptional regulator). In some cases, a Gram positive microbe may have an iron-only nitrogenase system comprising: anfK, anfG, anfD, anfH, anfA (transcriptional regulator). In some cases, a Gram positive microbe may have a nitrogenase system comprising glnB, and glnK (nitrogen signaling proteins). Some examples of enzymes involved in nitrogen metabolism in Gram positive microbes include glnA (glutamine synthetase), gdh (glutamate dehydrogenase), bdh (3-hydroxybutyrate dehydrogenase), glutaminase, gltAB/gltB/gltS (glutamate synthase), asnA/asnB (aspartate-ammonia ligase/asparagine synthetase), and ansA/ansZ (asparaginase).

Some examples of proteins involved in nitrogen transport in Gram positive microbes include amtB (ammonium transporter), glnK (regulator of ammonium transport), glnPHQ/glnQHMP (ATPdependent glutamine/glutamate transporters), glnT/alsT/yrbD/yflA (glutamine-like proton symport transporters), and gltP/gltT/yhcl/nqt (glutamate-like proton symport transporters).

Examples of Gram positive microbes which may be of particular interest include *Paenibacillus polymixa, Paenibacillus riograndensis, Paenibacillus* sp., *Frankia* sp., *Heliobacterium* sp., *Heliobacterium chlorum, Heliobacillus* sp., *Heliophilum* sp., *Heliorestis* sp., *Clostridium acetobutylicum, Clostridium* sp., *Mycobacterium flaum, Mycobacterium* sp., *Arthrobacter* sp., *Agromyces* sp., *Corynebacterium autitrophicum, Corynebacterium* sp., *Micromonspora* sp., *Propionibacteria* sp., *Streptomyces* sp., and *Microbacterium* sp.

Some examples of genetic alterations which may be made in Gram positive microbes include: deleting glnR to remove negative regulation of BNF in the presence of environmental nitrogen, inserting different promoters directly upstream of the nif cluster to eliminate regulation by GlnR in response to environmental nitrogen, mutating glnA to reduce the rate of ammonium assimilation by the GS-GOGAT pathway, deleting amtB to reduce uptake of ammonium from the media, mutating glnA so it is constitutively in the feedback-inhibited (FBI-GS) state, to reduce ammonium assimilation by the GS-GOGAT pathway.

In some cases, glnR is the main regulator of N metabolism and fixation in *Paenibacillus* species. In some cases, the genome of a *Paenibacillus* species may not contain a gene to produce glnR. In some cases, the genome of a *Paenibacillus* species may not contain a gene to produce glnE or glnD. In some cases, the genome of a *Paenibacillus* species may contain a gene to produce glnB or glnK. For example, *Paenibacillus* sp. WLY78 doesn't contain a gene for glnB, or its homologs found in the archaeon *Methanococcus maripaludis*, nifI1 and nifI2. In some cases, the genomes of

*Paenibacillus* species may be variable. For example, *Paenibacillus polymixa* E681 lacks glnK and gdh, has several nitrogen compound transporters, but only amtB appears to be controlled by GlnR. In another example, *Paenibacillus* sp. JDR2 has glnK, gdh and most other central nitrogen metabolism genes, has many fewer nitrogen compound transporters, but does have glnPHQ controlled by GlnR. *Paenibacillus riograndensis* SBR5 contains a standard glnRA operon, an fdx gene, a main nif operon, a secondary nif operon, and an anf operon (encoding irononly nitrogenase). Putative glnR/tnrA sites were found upstream of each of these operons. GlnR may regulate all of the above operons, except the anf operon. GlnR may bind to each of these regulatory sequences as a dimer.

*Paenibacillus* N-fixing strains may fall into two subgroups: Subgroup I, which contains only a minimal nif gene cluster and subgroup II, which contains a minimal cluster, plus an uncharacterized gene between nifX and hesA, and often other clusters duplicating some of the nif genes, such as nifH, nifHDK, nifBEN, or clusters encoding vanadaium nitrogenase (vnf) or irononly nitrogenase (anf) genes.

In some cases, the genome of a *Paenibacillus* species may not contain a gene to produce glnB or glnK. In some cases, the genome of a *Paenibacillus* species may contain a minimal nif cluster with 9 genes transcribed from a sigma-70 promoter. In some cases, a *Paenibacillus* nif cluster may be negatively regulated by nitrogen or oxygen. In some cases, the genome of a *Paenibacillus* species may not contain a gene to produce sigma-54. For example, *Paenibacillus* sp. WLY78 does not contain a gene for sigma-54. In some cases, a nif cluster may be regulated by glnR, and/or TnrA. In some cases, activity of a nif cluster may be altered by altering activity of glnR, and/or TnrA.

In Bacilli, glutamine synthetase (GS) is feedback-inhibited by high concentrations of intracellular glutamine, causing a shift in confirmation (referred to as FBI-GS). Nif clusters contain distinct binding sites for the regulators GlnR and TnrA in several Bacilli species. GlnR binds and represses gene expression in the presence of excess intracellular glutamine and AMP. A role of GlnR may be to prevent the influx and intracellular production of glutamine and ammonium under conditions of high nitrogen availability. TnrA may bind and/or activate (or repress) gene expression in the presence of limiting intracellular glutamine, and/or in the presence of FBI-GS. In some cases, the activity of a Bacilli nif cluster may be altered by altering the activity of GlnR.

Feedback-inhibited glutamine synthetase (FBI-GS) may bind GlnR and stabilize binding of GlnR to recognition sequences. Several bacterial species have a GlnR/TnrA binding site upstream of the nif cluster. Altering the binding of FBI-GS and GlnR may alter the activity of the nif pathway.

Sources of Microbes

The bacteria (or any microbe according to the disclosure) may be obtained from any general terrestrial environment, including its soils, plants, fungi, animals (including invertebrates) and other biota, including the sediments, water and biota of lakes and rivers; from the marine environment, its biota and sediments (for example, sea water, marine muds, marine plants, marine invertebrates (for example, sponges), marine vertebrates (for example, fish)); the terrestrial and marine geosphere (regolith and rock, for example, crushed subterranean rocks, sand and clays); the cryosphere and its meltwater; the atmosphere (for example, filtered aerial dusts, cloud and rain droplets); urban, industrial and other man-made environments (for example, accumulated organic and mineral matter on concrete, roadside gutters, roof surfaces, and road surfaces).

The plants from which the bacteria (or any microbe according to the disclosure) are obtained may be a plant having one or more desirable traits, for example a plant which naturally grows in a particular environment or under certain conditions of interest. By way of example, a certain plant may naturally grow in sandy soil or sand of high salinity, or under extreme temperatures, or with little water, or it may be resistant to certain pests or disease present in the environment, and it may be desirable for a commercial crop to be grown in such conditions, particularly if they are, for example, the only conditions available in a particular geographic location. By way of further example, the bacteria may be collected from commercial crops grown in such environments, or more specifically from individual crop plants best displaying a trait of interest amongst a crop grown in any specific environment: for example the fastest-growing plants amongst a crop grown in saline-limiting soils, or the least damaged plants in crops exposed to severe insect damage or disease epidemic, or plants having desired quantities of certain metabolites and other compounds, including fiber content, oil content, and the like, or plants displaying desirable colors, taste or smell. The bacteria may be collected from a plant of interest or any material occurring in the environment of interest, including fungi and other animal and plant biota, soil, water, sediments, and other elements of the environment as referred to previously.

The bacteria (or any microbe according to the disclosure) may be isolated from plant tissue. This isolation can occur from any appropriate tissue in the plant, including for example root, stem and leaves, and plant reproductive tissues. By way of example, conventional methods for isolation from plants typically include the sterile excision of the plant material of interest (e.g., root or stem lengths, leaves), surface sterilization with an appropriate solution (e.g. 2% sodium hypochlorite), after which the plant material is placed on nutrient medium for microbial growth.

Alternatively, the surface-sterilized plant material can be crushed in a sterile liquid (usually water) and the liquid suspension, including small pieces of the crushed plant material spread over the surface of a suitable solid agar medium, or media, which may or may not be selective (e.g. contain only phytic acid as a source of phosphorus). This approach is especially useful for bacteria which form isolated colonies and can be picked off individually to separate plates of nutrient medium, and further purified to a single species by well-known methods. Alternatively, the plant root or foliage samples may not be surface sterilized but only washed gently thus including surface dwelling epiphytic microorganisms in the isolation process, or the epiphytic microbes can be isolated separately, by imprinting and lifting off pieces of plant roots, stem or leaves onto the surface of an agar medium and then isolating individual colonies as above. This approach is especially useful for bacteria, for example. Alternatively, the roots may be processed without washing off small quantities of soil attached to the roots, thus including microbes that colonize the plant rhizosphere. Otherwise, soil adhering to the roots can be removed, diluted and spread out onto agar of suitable selective and non-selective media to isolate individual colonies of rhizospheric bacteria.

Agricultural Compositions

Compositions comprising bacteria or bacterial populations produced according to methods described herein and/or having characteristics as described herein can be in the form of a liquid, a foam, or a dry product. Compositions comprising bacteria or bacterial populations produced according to methods described herein and/or having characteristics as described herein may also be used to improve plant traits. In some examples, a composition comprising bacterial populations may be in the form of a dry powder, a slurry of powder and water, or a flowable seed treatment. The compositions comprising bacterial populations may be coated on a surface of a seed, and may be in liquid form.

The composition can be fabricated in bioreactors such as continuous stirred tank reactors, batch reactors, and on the farm. In some examples, compositions can be stored in a container, such as a jug or in mini bulk. In some examples, compositions may be stored within an object selected from the group consisting of a bottle, jar, ampule, package, vessel, bag, box, bin, envelope, carton, container, silo, shipping container, truck bed, and case.

Compositions may also be used to improve plant traits. In some examples, one or more compositions may be coated onto a seed. In some examples, one or more compositions may be coated onto a seedling. In some examples, one or more compositions may be coated onto a surface of a seed. In some examples, one or more compositions may be coated as a layer above a surface of a seed. In some examples, a composition that is coated onto a seed may be in liquid form, in dry product form, in foam form, in a form of a slurry of powder and water, or in a flowable seed treatment. In some examples, one or more compositions may be applied to a seed and/or seedling by spraying, immersing, coating, encapsulating, and/or dusting the seed and/or seedling with the one or more compositions. In some examples, multiple bacteria or bacterial populations can be coated onto a seed and/or a seedling of the plant. In some examples, at least two, at least three, at least four, at least five, at least six, at least seven, at least eight, at least nine, at least ten, or more than ten bacteria of a bacterial combination can be selected from one of the following genera: Acidovorax, *Agrobacterium*, *Bacillus*, *Burkholderia*, *Chryseobacterium*, *Curtobacterium*, *Enterobacter*, *Escherichia*, *Methylobacterium*, *Paenibacillus*, *Pantoea*, *Pseudomonas*, *Ralstonia*, *Saccharibacillus*, *Sphingomonas*, and *Stenotrophomonas*.

Examples of compositions may include seed coatings for commercially important agricultural crops, for example, *sorghum*, canola, tomato, strawberry, barley, rice, maize, and wheat. Examples of compositions can also include seed coatings for corn, soybean, canola, *sorghum*, potato, rice, vegetables, cereals, and oilseeds. Seeds as provided herein can be genetically modified organisms (GMO), non-GMO, organic, or conventional. In some examples, compositions may be sprayed on the plant aerial parts, or applied to the roots by inserting into furrows in which the plant seeds are planted, watering to the soil, or dipping the roots in a suspension of the composition. In some examples, compositions may be dehydrated in a suitable manner that maintains cell viability and the ability to artificially inoculate and colonize host plants. The bacterial species may be present in compositions at a concentration of between 108 to 1010 CFU/ml. In some examples, compositions may be supplemented with trace metal ions, such as molybdenum ions, iron ions, manganese ions, or combinations of these ions. The concentration of ions in examples of compositions as described herein may between about 0.1 mM and about 50 mM. Some examples of compositions may also be formulated with a carrier, such as beta-glucan, carboxylmethyl cellulose (CMC), bacterial extracellular polymeric substance (EPS), sugar, animal milk, or other suitable carriers. In some examples, peat or planting materials can be used as a carrier, or biopolymers in which a composition is entrapped in the biopolymer can be used as a carrier. The compositions comprising the bacterial populations described herein can improve plant traits, such as promoting plant growth, maintaining high chlorophyll content in leaves, increasing fruit or seed numbers, and increasing fruit or seed unit weight.

The compositions comprising the bacterial populations described herein may be coated onto the surface of a seed. As such, compositions comprising a seed coated with one or more bacteria described herein are also contemplated. The seed coating can be formed by mixing the bacterial population with a porous, chemically inert granular carrier. Alternatively, the compositions may be inserted directly into the furrows into which the seed is planted or sprayed onto the plant leaves or applied by dipping the roots into a suspension of the composition. An effective amount of the composition can be used to populate the sub-soil region adjacent to the roots of the plant with viable bacterial growth, or populate the leaves of the plant with viable bacterial growth. In general, an effective amount is an amount sufficient to result in plants with improved traits (e.g. a desired level of nitrogen fixation).

Bacterial compositions described herein can be formulated using an agriculturally acceptable carrier. The formulation useful for these embodiments may include at least one member selected from the group consisting of a tackifier, a microbial stabilizer, a fungicide, an antibacterial agent, a preservative, a stabilizer, a surfactant, an anti-complex agent, an herbicide, a nematicide, an insecticide, a plant growth regulator, a fertilizer, a rodenticide, a dessicant, a bactericide, a nutrient, and any combination thereof. In some examples, compositions may be shelf-stable. For example, any of the compositions described herein can include an agriculturally acceptable carrier (e.g., one or more of a fertilizer such as a non-naturally occurring fertilizer, an adhesion agent such as a non-naturally occurring adhesion agent, and a pesticide such as a non-naturally occurring pesticide). A non-naturally occurring adhesion agent can be, for example, a polymer, copolymer, or synthetic wax. For example, any of the coated seeds, seedlings, or plants described herein can contain such an agriculturally acceptable carrier in the seed coating. In any of the compositions or methods described herein, an agriculturally acceptable carrier can be or can include a non-naturally occurring compound (e.g., a non-naturally occurring fertilizer, a non-naturally occurring adhesion agent such as a polymer, copolymer, or synthetic wax, or a non-naturally occurring pesticide). Non-limiting examples of agriculturally acceptable carriers are described below. Additional examples of agriculturally acceptable carriers are known in the art.

In some cases, bacteria are mixed with an agriculturally acceptable carrier. The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in the composition. Water-in-oil emulsions can also be used to formulate a composition that includes the isolated bacteria (see, for example, U.S. Pat. No. 7,485,451).

Suitable formulations that may be prepared include wettable powders, granules, gels, agar strips or pellets, thickeners, and the like, microencapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or a plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the bacteria, such as barley, rice, or other biological materials such as seed, plant parts, sugar cane bagasse, hulls or stalks from grain processing, ground plant material or wood from building site refuse, sawdust or small fibers from recycling of paper, fabric, or wood.

For example, a fertilizer can be used to help promote the growth or provide nutrients to a seed, seedling, or plant. Non-limiting examples of fertilizers include nitrogen, phosphorous, potassium, calcium, sulfur, magnesium, boron, chloride, manganese, iron, zinc, copper, molybdenum, and selenium (or a salt thereof). Additional examples of fertilizers include one or more amino acids, salts, carbohydrates, vitamins, glucose, NaCl, yeast extract, $NH_4H_2PO_4$, $(NH_4)_2SO_4$, glycerol, valine, L-leucine, lactic acid, propionic acid, succinic acid, malic acid, citric acid, KH tartrate, xylose, lyxose, and lecithin. In one embodiment, the formulation can include a tackifier or adherent (referred to as an adhesive agent) to help bind other active agents to a substance (e.g., a surface of a seed). Such agents are useful for combining bacteria with carriers that can contain other compounds (e.g., control agents that are not biologic), to yield a coating composition. Such compositions help create coatings around the plant or seed to maintain contact between the microbe and other agents with the plant or plant part. In one embodiment, adhesives are selected from the group consisting of: alginate, gums, starches, lecithins, formononetin, polyvinyl alcohol, alkali formononetinate, hesperetin, polyvinyl acetate, cephalins, Gum Arabic, Xanthan Gum, Mineral Oil, Polyethylene Glycol (PEG), Polyvinyl pyrrolidone (PVP), Arabinogalactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers.

In some embodiments, the adhesives can be, e.g. a wax such as carnauba wax, beeswax, Chinese wax, shellac wax, spermaceti wax, candelilla wax, castor wax, ouricury wax, and rice bran wax, a polysaccharide (e.g., starch, dextrins, maltodextrins, alginate, and chitosans), a fat, oil, a protein (e.g., gelatin and zeins), gum arables, and shellacs. Adhesive agents can be non-naturally occurring compounds, e.g., polymers, copolymers, and waxes. For example, non-limiting examples of polymers that can be used as an adhesive agent include: polyvinyl acetates, polyvinyl acetate copolymers, ethylene vinyl acetate (EVA) copolymers, polyvinyl alcohols, polyvinyl alcohol copolymers, celluloses (e.g., ethylcelluloses, methylcelluloses, hydroxymethylcelluloses, hydroxypropylcelluloses, and carboxymethylcelluloses), polyvinylpyrolidones, vinyl chloride, vinylidene chloride copolymers, calcium lignosulfonates, acrylic copolymers, polyvinylacrylates, polyethylene oxide, acylamide polymers and copolymers, polyhydroxyethyl acrylate, methylacrylamide monomers, and polychloroprene.

In some examples, one or more of the adhesion agents, anti-fungal agents, growth regulation agents, and pesticides (e.g., insecticide) are non-naturally occurring compounds (e.g., in any combination). Additional examples of agriculturally acceptable carriers include dispersants (e.g., polyvinylpyrrolidone/vinyl acetate PVPIVA S-630), surfactants, binders, and filler agents.

The formulation can also contain a surfactant. Non-limiting examples of surfactants include nitrogen-surfactant blends such as Prefer 28 (Cenex), Surf-N(US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision). In one embodiment, the surfactant is present at a concentration of between 0.01% v/v to 10% v/v. In another embodiment, the surfactant is present at a concentration of between 0.1% v/v to 1% v/v.

In certain cases, the formulation includes a microbial stabilizer. Such an agent can include a desiccant, which can include any compound or mixture of compounds that can be classified as a desiccant regardless of whether the compound or compounds are used in such concentrations that they in fact have a desiccating effect on a liquid inoculant. Such desiccants are ideally compatible with the bacterial population used, and should promote the ability of the microbial population to survive application on the seeds and to survive desiccation. Examples of suitable desiccants include one or more of trehalose, sucrose, glycerol, and methylene glycol. Other suitable desiccants include, but are not limited to, non-reducing sugars and sugar alcohols (e.g., mannitol or sorbitol). The amount of desiccant introduced into the formulation can range from about 5% to about 50% by weight/volume, for example, between about 10% to about 40%, between about 15% to about 35%, or between about 20% to about 30%. In some cases, it is advantageous for the formulation to contain agents such as a fungicide, an antibacterial agent, an herbicide, a nematicide, an insecticide, a plant growth regulator, a rodenticide, bactericide, or a nutrient. In some examples, agents may include protectants that provide protection against seed surface-borne pathogens. In some examples, protectants may provide some level of control of soil-borne pathogens. In some examples, protectants may be effective predominantly on a seed surface.

In some examples, a fungicide may include a compound or agent, whether chemical or biological, that can inhibit the growth of a fungus or kill a fungus. In some examples, a fungicide may include compounds that may be fungistatic or fungicidal. In some examples, fungicide can be a protectant, or agents that are effective predominantly on the seed surface, providing protection against seed surface-borne pathogens and providing some level of control of soil-borne pathogens. Non-limiting examples of protectant fungicides include captan, maneb, thiram, or fludioxonil.

In some examples, fungicide can be a systemic fungicide, which can be absorbed into the emerging seedling and inhibit or kill the fungus inside host plant tissues. Systemic fungicides used for seed treatment include, but are not limited to the following: azoxystrobin, carboxin, mefenoxam, metalaxyl, thiabendazole, trifloxystrobin, and various triazole fungicides, including difenoconazole, ipconazole, tebuconazole, and triticonazole. Mefenoxam and metalaxyl are primarily used to target the water mold fungi *Pythium* and *Phytophthora*. Some fungicides are preferred over others, depending on the plant species, either because of subtle differences in sensitivity of the pathogenic fungal species, or because of the differences in the fungicide distribution or sensitivity of the plants. In some examples, fungicide can be a biological control agent, such as a bacterium or fungus. Such organisms may be parasitic to the pathogenic fungi, or secrete toxins or other substances which can kill or otherwise prevent the growth of fungi. Any type of fungicide, particularly ones that are commonly used on plants, can be used as a control agent in a seed composition.

In some examples, the seed coating composition comprises a control agent which has antibacterial properties. In one embodiment, the control agent with antibacterial properties is selected from the compounds described herein elsewhere. In another embodiment, the compound is Streptomycin, oxytetracycline, oxolinic acid, or gentamicin. Other examples of antibacterial compounds which can be used as part of a seed coating composition include those based on dichlorophene and benzylalcohol hemi formal (Proxel® from ICI or Acticide® RS from Thor Chemie and Kathon® MK 25 from Rohm & Haas) and isothiazolinone derivatives such as alkylisothiazolinones and benzisothiazolinones (Acticide® MBS from Thor Chemie).

In some examples, growth regulator is selected from the group consisting of: Abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione phosphorotrithioate, 2,3,5-tri-iodobenzoic acid, trinexapac-ethyl and uniconazole. Additional non-limiting examples of growth regulators include brassinosteroids, cytokinines (e.g., kinetin and zeatin), auxins (e.g., indolylacetic acid and indolylacetyl aspartate), flavonoids and isoflavanoids (e.g., formononetin and diosmetin), phytoaixins (e.g., glyceolline), and phytoalexin-inducing oligosaccharides (e.g., pectin, chitin, chitosan, polygalacuronic acid, and oligogalacturonic acid), and gibellerins. Such agents are ideally compatible with the agricultural seed or seedling onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

Some examples of nematode-antagonistic biocontrol agents include ARF18; 30 *Arthrobotrys* spp.; *Chaetomium* spp.; *Cylindrocarpon* spp.; *Exophilia* spp.; *Fusarium* spp.; *Gliocladium* spp.; *Hirsutella* spp.; *Lecanicillium* spp.; *Monacrosporium* spp.; *Myrothecium* spp.; *Neocosmospora* spp.; *Paecilomyces* spp.; *Pochonia* spp.; *Stagonospora* spp.; vesicular-arbuscular mycorrhizal fungi, *Burkholderia* spp.; *Pasteuria* spp., *Brevibacillus* spp.; *Pseudomonas* spp.; and *Rhizobacteria*. Particularly preferred nematode-antagonistic biocontrol agents include ARF18, *Arthrobotrys oligospora, Arthrobotrys dactyloides, Chaetomium globosum, Cylindrocarpon heteronema, Exophilia jeanselmei, Exophilia pisciphila, Fusarium aspergilus, Fusarium solani, Gliocladium catenulatum, Gliocladium roseum, Gliocladium vixens, Hirsutella rhossiliensis, Hirsutella minnesotensis, Lecanicillium lecanii, Monacrosporium drechsleri, Monacrosporium gephyropagum, Myrotehcium verrucaria, Neocosmospora vasinfecta, Paecilomyces lilacinus, Pochonia chlamydosporia, Stagonospora heteroderae, Stagonospora phaseoli,* vesiculararbuscular mycorrhizal fungi, *Burkholderia cepacia, Pasteuria penetrans, Pasteuria thornei, Pasteuria nishizawae, Pasteuria ramosa, Pastrueia usage, Brevibacillus laterosporus* strain G4, *Pseudomonas fluorescens* and *Rhizobacteria*.

Some examples of nutrients can be selected from the group consisting of a nitrogen fertilizer including, but not limited to Urea, Ammonium nitrate, Ammonium sulfate, Non-pressure nitrogen solutions, Aqua ammonia, Anhydrous ammonia, Ammonium thiosulfate, Sulfur-coated urea, Urea-formaldehydes, IBDU, Polymer-coated urea, Calcium nitrate, Ureaform, and Methylene urea, phosphorous fertilizers such as Diammonium phosphate, Monoammonium phosphate, Ammonium polyphosphate, Concentrated superphosphate and Triple superphosphate, and potassium fertilizers such as Potassium chloride, Potassium sulfate, Potassium-magnesium sulfate, Potassium nitrate. Such compositions can exist as free salts or ions within the seed coat composition. Alternatively, nutrients/fertilizers can be complexed or chelated to provide sustained release over time.

Some examples of rodenticides may include selected from the group of substances consisting of 2-isovalerylindan-1, 3-dione, 4-(quinoxalin-2-ylamino) benzenesulfonamide, alphachlorohydrin, aluminum phosphide, antu, arsenous oxide, barium carbonate, bisthiosemi, brodifacoum, bromadiolone, bromethalin, calcium cyanide, chloralose, chlorophacinone, cholecalciferol, coumachlor, coumafuryl, coumatetralyl, crimidine, difenacoum, difethialone, diphacinone, ergocalciferol, flocoumafen, fluoroacetamide, flupropadine, flupropadine hydrochloride, hydrogen cyanide, iodomethane, lindane, magnesium phosphide, methyl bromide, norbormide, phosacetim, phosphine, phosphorus, pindone, potassium arsenite, pyrinuron, scilliroside, sodium arsenite, sodium cyanide, sodium fluoroacetate, strychnine, thallium sulfate, warfarin and zinc phosphide.

In the liquid form, for example, solutions or suspensions, bacterial populations can be mixed or suspended in water or in aqueous solutions. Suitable liquid diluents or carriers include water, aqueous solutions, petroleum distillates, or other liquid carriers.

Solid compositions can be prepared by dispersing the bacterial populations in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil and cottonseed oil, glycerol, ethylene glycol, polyethylene glycol, propylene glycol, polypropylene glycol, etc.

Plant Species

The methods and bacteria described herein are suitable for any of a variety of plants, such as plants in the genera *Hordeum, Oryza, Zea*, and *Triticeae*. Other non-limiting examples of suitable plants include mosses, lichens, and algae. In some cases, the plants have economic, social and/or environmental value, such as food crops, fiber crops, oil crops, plants in the forestry or pulp and paper industries, feedstock for biofuel production and/or ornamental plants. In some examples, plants may be used to produce economically valuable products such as a grain, a flour, a starch, a syrup, a meal, an oil, a film, a packaging, a nutraceutical product, a pulp, an animal feed, a fish fodder, a bulk material for industrial chemicals, a cereal product, a processed human food product, a sugar, an alcohol, and/or a protein. Non-limiting examples of crop plants include maize, rice, wheat, barley, sorghum, millet, oats, rye triticale, buckwheat, sweet corn, sugar cane, onions, tomatoes, strawberries, and asparagus. In some embodiments, the methods and bacteria described herein are suitable for any of a variety of transgenic plants, non-transgenic plants, and hybrid plants thereof.

In some examples, plants that may be obtained or improved using the methods and compositions disclosed herein may include plants that are important or interesting for agriculture, horticulture, biomass for the production of biofuel molecules and other chemicals, and/or forestry. Some examples of these plants may include pineapple, banana, coconut, lily, grass peas and grass; and dicotyledonous plants, such as, for example, peas, alfalfa, tomatillo, melon, chickpea, chicory, clover, kale, lentil, soybean, tobacco, potato, sweet potato, radish, cabbage, rape, apple trees, grape, cotton, sunflower, thale cress, canola, citrus (including orange, mandarin, kumquat, lemon, lime, grapefruit, tangerine, tangelo, citron, and pomelo), pepper, bean, lettuce, *Panicum virgatum* (switch), *Sorghum bicolor* (*sorghum*, sudan), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), *Pennisetum glaucum* (pearl millet), *Panicum* spp. *Sorghum* spp., *Miscanthus* spp., *Saccharum* spp., *Erianthus* spp., *Populus* spp., *Secale cereale* (rye), *Salix* spp. (willow), *Eucalyptus* spp. (*eucalyptus*), *Triticosecale* spp. (*triticum*—25 wheat X rye), Bamboo, *Carthamus tinctorius* (safflower), *Jatropha curcas* (*Jatropha*), *Ricinus communis* (castor), *Elaeis guineensis* (oil palm), *Phoenix dactylifera* (date palm), *Archontophoenix cunninghamiana* (king palm), *Syagrus romanzoffiana* (queen palm), *Linum usitatissimum* (flax), *Brassica juncea*, *Manihot esculenta* (cassaya), *Lycopersicon esculentum* (tomato), *Lactuca saliva* (lettuce), *Musa paradisiaca* (banana), *Solanum tuberosum* (potato), *Brassica oleracea* (broccoli, cauliflower, brussel sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum* annum (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver somniferum* (opium poppy), *Papaver orientale*, *Taxus baccata*, *Taxus brevifolia*, *Artemisia annua*, *Cannabis saliva*, *Camptotheca acuminate*, *Catharanthus roseus*, *Vinca rosea*, *Cinchona officinalis*, *Coichicum autumnale*, *Veratrum californica*, *Digitalis lanata*, *Digitalis purpurea*, *Dioscorea* spp., *Andrographis paniculata*, *Atropa belladonna*, *Datura stomonium*, *Berberis* spp., *Cephalotaxus* spp., *Ephedra sinica*, *Ephedra* spp., *Erythroxylum coca*, *Galanthus wornorii*, *Scopolia* spp., *Lycopodium serratum* (*Huperzia serrata*), *Lycopodium* spp., *Rauwolfia serpentina*, *Rauwolfia* spp., *Sanguinaria canadensis*, *Hyoscyamus* spp., *Calendula officinalis*, *Chrysanthemum parthenium*, *Coleus forskohlii*, *Tanacetum parthenium*, *Parthenium argentatum* (guayule), *Hevea* spp. (rubber), *Mentha spicata* (mint), *Mentha piperita* (mint), *Bixa orellana*, *Alstroemeria* spp., *Rosa* spp. (rose), *Dianthus caryophyllus* (carnation), *Petunia* spp. (*petunia*), *Poinsettia pulcherrima* (poinsettia), *Nicotiana tabacum* (tobacco), *Lupinus albus* (lupin), *Uniola paniculata* (oats), *Hordeum vulgare* (barley), and *Lolium* spp. (rye).

In some examples, a monocotyledonous plant may be used. Monocotyledonous plants belong to the orders of the Alismatales, Arales, Arecales, Bromeliales, Commelinales, Cyclanthales, Cyperales, Eriocaulales, Hydrocharitales, Juncales, Lilliales, Najadales, Orchidales, Pandanales, Poales, Restionales, Triuridales, Typhales, and Zingiberales. Plants belonging to the class of the Gymnospermae are Cycadales, Ginkgoales, Gnetales, and Pinales. In some examples, the monocotyledonous plant can be selected from the group consisting of a maize, rice, wheat, barley, and sugarcane.

In some examples, a dicotyledonous plant may be used, including those belonging to the orders of the Aristochiales, Asterales, Batales, Campanulales, Capparales, Caryophyllales, Casuarinales, Celastrales, Cornales, Diapensales, Dilleniales, Dipsacales, Ebenales, Ericales, Eucomiales, Euphorbiales, Fabales, Fagales, Gentianales, Geraniales, Haloragales, Hamamelidales, Middles, Juglandales, Lamiales, Laurales, Lecythidales, Leitneriales, Magniolales, Malvales, Myricales, Myrtales, Nymphaeales, Papeverales, Piperales, Plantaginales, Plumb aginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Theales, Trochodendrales, Umbellales, Urticales, and Violates.

In some examples, the dicotyledonous plant can be selected from the group consisting of cotton, soybean, pepper, and tomato.

In some cases, the plant to be improved is not readily amenable to experimental conditions. For example, a crop plant may take too long to grow enough to practically assess an improved trait serially over multiple iterations. Accordingly, a first plant from which bacteria are initially isolated, and/or the plurality of plants to which genetically manipulated bacteria are applied may be a model plant, such as a plant more amenable to evaluation under desired conditions. Non-limiting examples of model plants include *Setaria*, Brachypodium, and *Arabidopsis*. Ability of bacteria isolated according to a method of the disclosure using a model plant may then be applied to a plant of another type (e.g. a crop plant) to confirm conferral of the improved trait.

Traits that may be improved by the methods disclosed herein include any observable characteristic of the plant, including, for example, growth rate, height, weight, color, taste, smell, changes in the production of one or more compounds by the plant (including for example, metabolites, proteins, drugs, carbohydrates, oils, and any other compounds). Selecting plants based on genotypic information is also envisaged (for example, including the pattern of plant gene expression in response to the bacteria, or identifying the presence of genetic markers, such as those associated with increased nitrogen fixation). Plants may also be selected based on the absence, suppression or inhibition of a certain feature or trait (such as an undesirable feature or trait) as opposed to the presence of a certain feature or trait (such as a desirable feature or trait).

Non-Genetically Modified Maize

The methods and bacteria described herein are suitable for any of a variety of nongenetically modified maize plants or part thereof. And in some aspects, the corn is organic. Furthermore, the methods and bacteria described herein are suitable for any of the following nongenetically modified hybrids, varieties, lineages, etc. In some embodiments, corn varieties generally fall under six categories: sweet corn, flint corn, popcorn, dent corn, pod corn, and flour corn.

Sweet Corn

Yellow su varieties include Earlivee, Early Sunglow, Sundance, Early Golden Bantam, Iochief, Merit, Jubilee, and Golden Cross Bantam. White su varieties include True Platinum, Country Gentleman, Silver Queen, and Stowell's Evergreen. Bicolor su varieties include Sugar & Gold, Quickie, Double Standard, Butter & Sugar, Sugar Dots, Honey & Cream. Multicolor su varieties include Hookers, Triple Play, Painted Hill, Black Mexican/Aztec.

Yellow se varieties include Buttergold, Precocious, Spring Treat, Sugar Buns, Colorow, Kandy King, Bodacious R/M, Tuxedo, Incredible, Merlin, Miracle, and Kandy Korn EH. White se varieties include Spring Snow, Sugar Pearl, Whiteout, Cloud Nine, Alpine, Silver King, and Argent. Bicolor se varieties include Sugar Baby, Fleet, Bon Jour, Trinity, Bi-Licious, Temptation, Luscious, Ambrosia, Accord, Brocade, Lancelot, Precious Gem, Peaches and Cream Mid EH, and Delectable R/M. Multicolor se varieties include Ruby Queen.

Yellow sh2 varieties include Extra Early Super Sweet, Takeoff, Early Xtra Sweet, Raveline, Summer Sweet Yellow, Krispy King, Garrison, Illini Gold, Challenger, Passion, Excel, Jubilee SuperSweet, Illini Xtra Sweet, and Crisp 'N Sweet. White sh2 varieties include Summer Sweet White, Tahoe, Aspen, Treasure, How Sweet It Is, and Camelot. Bicolor sh2 varieties include Summer Sweet Bicolor, Radiance, Honey 'N Pearl, Aloha, Dazzle, Hudson, and Phenomenal.

Yellow sy varieties include Applause, Inferno, Honeytreat, and Honey Select. White sy varieties include Silver Duchess, Cinderella, Mattapoisett, Avalon, and Captivate. Bicolor sy varieties include Pay Dirt, Revelation, Renaissance, Charisma, Synergy, Montauk, Kristine, Serendipity/Providence, and Cameo.

Yellow augmented supersweet varieties include Xtra-Tender iddA, Xtra-Tender 11dd, Mirai 131Y, Mirai 130Y, Vision, and Mirai 002. White augmented supersweet varieties include Xtra-Tender 3dda, Xtra-Tender 31dd, Mirai 421 W, XTH 3673, and Devotion. Bicolor augmented supersweet varieties include Xtra-Tender 2dda, Xtra-Tender 21dd, Kickoff XR, Mirai 308BC, Anthem XR, Mirai 336BC, Fantastic XR, Triumph, Mirai 301BC, Stellar, American Dream, Mirai 350BC, and Obsession.

Flint Corn

Flint corn varieties include Bronze-Orange, Candy Red Flint, Floriani Red Flint, Glass Gem, Indian Ornamental (Rainbow), Mandan Red Flour, Painted Mountain, Petmecky, Cherokee White Flour, Pop Corn Pop corn varieties include Monarch Butterfly, Yellow Butterfly, Midnight Blue, Ruby Red, Mixed Baby Rice, Queen Mauve, Mushroom Flake, Japanese Hull-less, Strawberry, Blue Shaman, Miniature Colored, Miniature Pink, Pennsylvania Dutch Butter Flavor, and Red Strawberry.

Dent Corn

Dent corn varieties include Bloody Butcher, Blue Clarage, Ohio Blue Clarage, Cherokee White Eagle, Hickory Cane, Hickory King, Jellicorse Twin, Kentucky Rainbow, Daymon Morgan's Knt. Butcher, Leaming, Leaming's Yellow, McCormack's Blue Giant, Neal Paymaster, Pungo Creek Butcher, Reid's Yellow Dent, Rotten Clarage, and Tennessee Red Cob.

In some embodiments, corn varieties include P1618 W, P1306 W, P1345, P1151, P1197, P0574, P0589, and P0157. W=white corn.

In some embodiments, the methods and bacteria described herein are suitable for any hybrid of the maize varieties set forth herein.

Genetically Modified Maize

The methods and bacteria described herein are suitable for any of a hybrid, variety, lineage, etc. of genetically modified maize plants or part thereof.

EXAMPLES

The maize hybrid DKC 66-40 was grown under standard greenhouse growth conditions with a 15-hour day length and temperature set points of 25° C. during daylight hours and 22° C. during night hours. Seeds were planted in standard potting mix combined 1:1 with calcined clay by pressing (2) 2-inch holes near the center of each pot with a planting tool. One seed was then dropped into each prepared hole and inoculated with sterile PBS (UTC controls) or a bacterial suspension of the strain 137-3890, a microbe with an increased potential to fix nitrogen in planta, using cells diluted to a prescribed optical density. Seedlings were given water only for the first week, then thinned to a single plant per pot by selecting the most vigorous seedling and removing the remaining plant at approximately 7 days after planting. At one-week post planting, fertigation began on all plants using a modified Hoagland's solution containing 2 mM of total nitrogen. Fertigation typically occurred twice per week, and additional water was given to all plants as needed.

At 3 weeks post-planting, plants were moved to chamber 102. After closing and sealing the chamber, 20 L of gas were removed from the chamber and replaced with the same volume of 98% atom $^{15}$N gas (obtained from Sigma-Aldrich, St. Louis, MO), such that the internal atmosphere of chamber 102 was raised to approximately 0.5 atom % $^{15}$N. Growth conditions in the chamber were controlled such that plants experienced a constant humidity of approximately 60%, supplemental light from metal halide lamps for 15 hours per day, and day and night temperatures as described above. Oxygen and carbon dioxide levels were monitored and adjusted as necessary to pre-determined set values. Irrigation with the same 2 mM modified Hoagland's solution was performed two times per week without opening chamber 102 to the external environment.

Plants were harvested after two weeks in the chamber and approximately five weeks after planting (e.g., at the V8 growth stage). Plants were sectioned into four distinct portions: root tissue, newly emerged whorl tissue, top-collared leaf tissue, and all remaining vegetative tissue (other vegetative tissue). Dry weight (weight in grams of whole plant after complete drying to a stable weight) was measured approximately 14 days after plant harvest for each tissue portion. Samples were then ground to a fine powder and isotopic analysis was performed at the UC Davis Stable Isotope Facility (Davis, CA, USA). For each sample, percent nitrogen and percent $^{15}$N were determined.

Figure 11A:
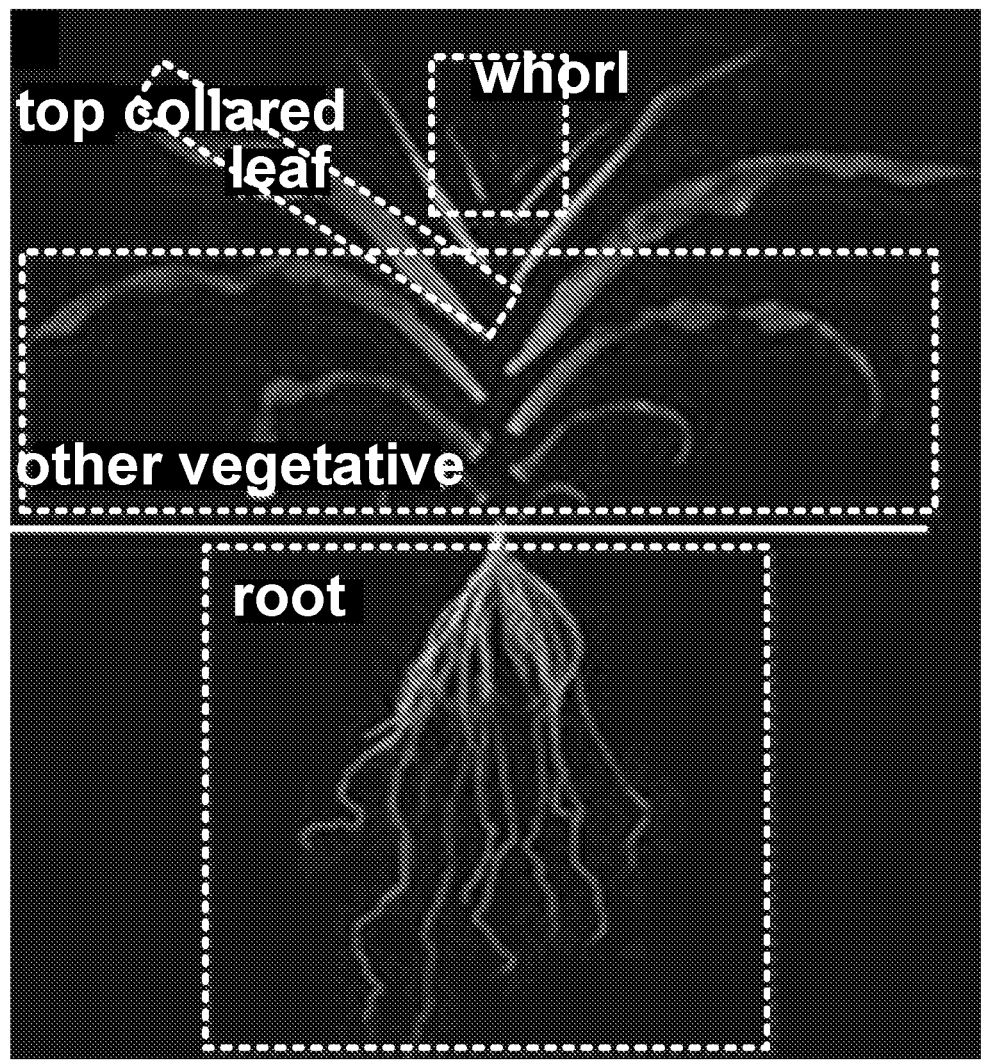
FIG. 11A is a schematic diagram showing different portions of plant tissue.
Figure 11B:
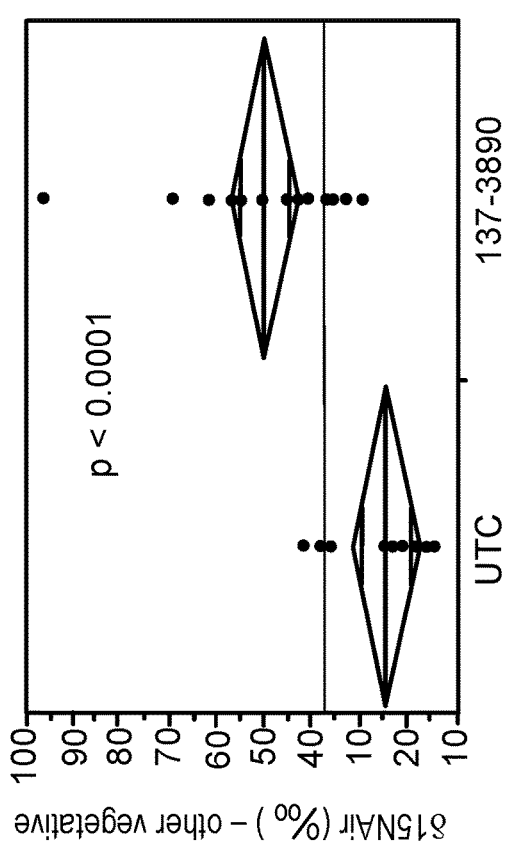
FIGS. 11B-11E are plots showing changes in $^{15}N$ abundance ($\delta^{15}N$) in tissues harvested from plants that were inoculated with a nitrogen-fixing bacterial strain, relative to tissues harvested non-inoculated plants.
Figure 11C:
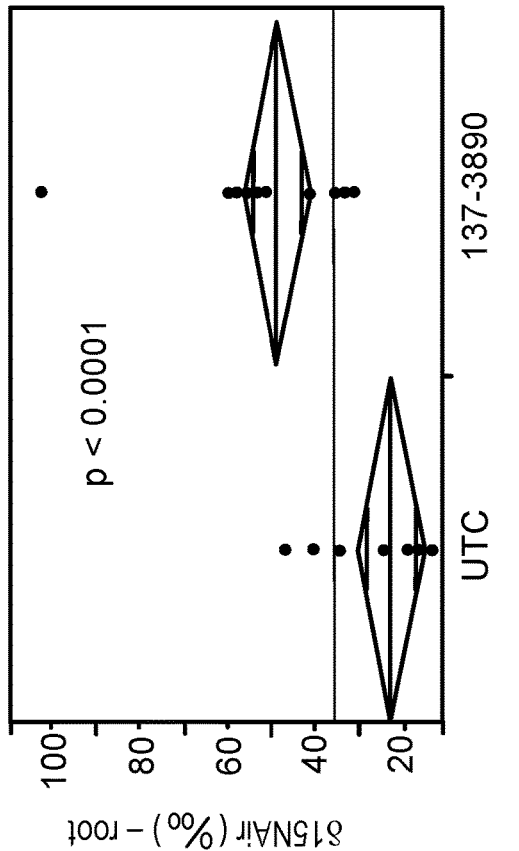
Figure 11D:
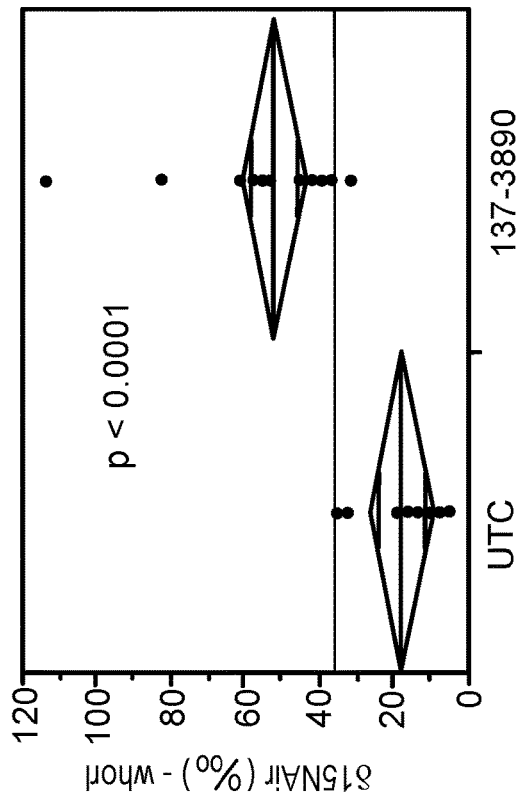
Figure 11E:
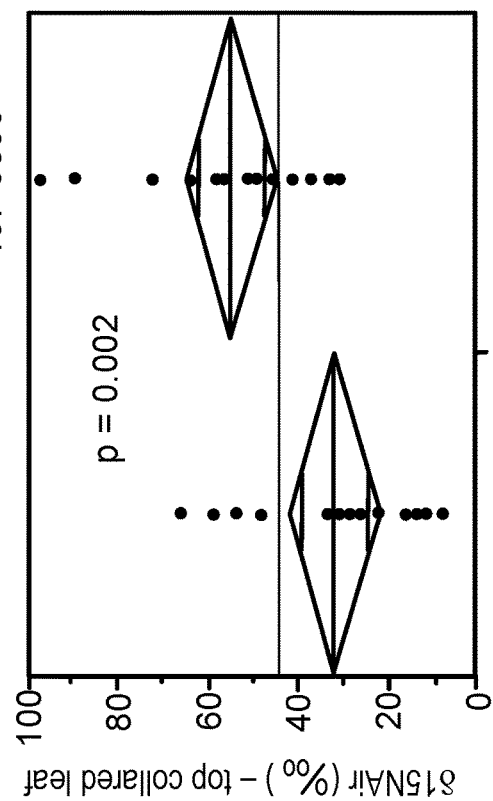

FIG. 11A is a diagram showing the different types of leaf tissue that were analyzed, and FIGS. 11B-11E are plots showing the change in $^{15}$N abundance ($\delta^{15}$N) in tissues harvested from plants that were inoculated with the strain 137-3890, relative corresponding tissues harvested and analyzed from plants that were not inoculated (the "UTC" controls). For whorl tissue (FIG. 11B), top-collared leaf tissue (FIG. 11C), other vegetative tissue (FIG. 11D), and root tissue (FIG. 11E) derived from inoculated plants, nitrogen incorporation—as measured by the change in $^{15}N$ abundance in the tissues—was higher than for corresponding tissues of non-inoculated plants.

A biologically pure culture of *Klebsiella variicola* was deposited on Apr. 2, 2020, with the American Type Culture Collection (ATCC; an International Depositary Authority), Manassas, VA, USA, and assigned ATTC Patent Deposit Designation number PTA-126749. This deposit was made under the provisions of the Budapest Treaty on the International Recognition of the Deposit of Microorganisms for the Purpose of Patent Procedure and the Regulations (Budapest Treaty).

Other Embodiments

Other features and aspects of the systems, methods, and compositions described herein are described, for example, in PCT Application Publication Nos. WO 2019/084059, WO 2019/084342, and WO 2020/014498, the entire contents of each of which are incorporated herein by reference.

While this disclosure describes specific implementations, these should not be construed as limitations on the scope of the disclosure, but rather as descriptions of features in certain embodiments. Features that are described in the context of separate embodiments can also generally be implemented in combination in a single embodiment. Conversely, various features that are described in the context of a single embodiment can also be implemented in multiple embodiments separately or in any suitable sub-combination. Moreover, although features may be described above as present in certain combinations and even initially claimed as such, one or more features from a claimed combination can generally be excised from the combination, and the claimed combination may be directed to a sub-combination or variation of a sub-combination.

In addition to the embodiments expressly disclosed herein, it will be understood that various modifications to the embodiments described may be made without departing from the spirit and scope of the disclosure. Accordingly, other embodiments are within the scope of the following claims.

What is claimed is:

1. A system for plant culture, comprising:
a chamber comprising one or more walls enclosing a spatial volume internal to the chamber, wherein the one or more walls comprise a surface for supporting a plant within the enclosed spatial volume;
a gas delivery apparatus, comprising at least one gas source;
a nutrient delivery apparatus comprising a reservoir;
a sampling apparatus connected to a port formed in the one or more walls; and
a controller connected to the gas delivery apparatus and the nutrient delivery apparatus, and configured so that during operation of the system, with a plant entirely positioned within the enclosed spatial volume of the chamber, the controller:
  activates the nutrient delivery apparatus to deliver an aqueous growth medium to the plant; and
  activates the gas delivery apparatus to deliver into the enclosed spatial volume a mixture of isotopically-substituted gases.

2. The system of claim 1, wherein a height of the enclosed spatial volume measured between the surface and a wall or wall portion opposite the surface is at least 0.5 meters.

3. The system of claim 1, wherein when the chamber is filled with a gas at a pressure p at a first time, the one or more walls of the chamber are sufficiently impermeable so that the gas pressure within the chamber at a second at least 7 days after the first time is 0.80p or more.

4. The system of claim 1, wherein the gas delivery apparatus comprises a valve connected to the controller, and wherein during operation of the system, the controller is configured to activate the valve to regulate gas delivery from the gas delivery apparatus.

5. The system of claim 4, wherein during operation of the system, the at least one gas source comprises a source of nitrogen gas for which an isotopic ratio of $^{15}N$ to $^{14}N$ is greater than a ratio of $^{15}N$ to $^{14}N$ in atmospheric nitrogen gas.

6. The system of claim 4, wherein during operation of the system, the at least one gas source comprises a source of nitrogen gas for which an isotopic ratio of $^{13}N$ to $^{14}N$ is greater than a ratio of $^{13}N$ to $^{14}N$ in atmospheric nitrogen gas.

7. The system of claim 6, further comprising a gas detector connected to the controller and configured to generate a measurement signal in response to a presence of one or more gas species within the chamber.

8. The system of claim 4, wherein during operation of the system, the gas delivery apparatus comprises a source of carbon dioxide gas.

9. The system of claim 8, further comprising a gas detector connected to the controller and configured to generate a measurement signal representing an amount of carbon dioxide gas in the chamber.

10. The system of claim 4, wherein the gas delivery apparatus comprises an acetylene gas source, and wherein the system comprises an ethylene detector connected to the controller.

11. The system of claim 1, further comprising a gas detector connected to the controller and configured to generate a measurement signal in response to a presence of one or more gas species within the chamber.

12. The system of claim 11, wherein the gas detector is configured to generate a measurement signal representing an amount of nitrous oxide in the chamber.

13. The system of claim 1, further comprising a growth monitoring apparatus connected to the controller and configured to generate a measurement signal comprising information about growth of a plant within the chamber.

14. The system of claim 13, wherein the growth monitoring apparatus comprises:
a radiation source configured to direct illumination light to be incident on a plant within the chamber; and
a detector configured to detect light emitted from the plant.

15. The system of claim 14, wherein the detector is configured to detect light emitted from the plant in multiple distinct spectral bands, each comprising a local maximum spectral wavelength.

16. The system of claim 1, further comprising at least one chemical sensor connected to the controller and configured to generate a measurement signal comprising information about an analyte within the chamber.

17. The system of claim 1, further comprising at least one sensor connected to the controller and configured to generate a measurement signal comprising information about a change in plant mass within the chamber.

18. The system of claim 1, further comprising a fluid removal mechanism comprising a conduit connected to or extending through a port formed in the one or more walls and configured to extract a fluid from the chamber.

19. A method of detecting nitrogen incorporation in a plant, the method comprising:
positioning a test plant in a support medium within an enclosed chamber of a plant culture system;
adjusting a composition of a nitrogen gas mixture within the chamber so that a ratio of at least two nitrogen isotopes is different from a naturally occurring atmospheric ratio of the isotopes;
delivering an aqueous growth medium to the test plant to cause growth of the test plant over a growth period;
performing an isotope analysis of a test plant tissue to determine relative amounts of the at least two nitrogen isotopes in the test plant tissue; and
comparing the relative amounts of the at least two nitrogen isotopes in the test plant tissue to reference information to detect nitrogen incorporation in the test plant.

20. The method of claim 19, wherein adjusting the composition of nitrogen gas comprises activating a gas delivery apparatus of the plant culture system to deliver nitrogen gas comprising a ratio of the at least two nitrogen isotopes that differs from a naturally occurring ratio of the at least two isotopes in atmospheric nitrogen gas.

21. The method of claim 19, further comprising harvesting the test plant tissue.

22. The method of claim 19, wherein the reference information is derived from tissue of a reference plant.

23. The method of claim 22, further comprising growing the reference plant with the test plant in the enclosed chamber of the plant culture system.

24. The method of claim 23, wherein growing the reference plant comprises:
positioning the reference plant in a growth medium within the enclosed chamber of the plant culture system; and
delivering an aqueous growth medium to the reference plant to cause growth of the reference plant over the growth period.

25. The method of claim 24, further comprising, prior to positioning the test and reference plants within the enclosed chamber of the plant culture system, inoculating the test plant or a seed precursor of the test plant with a bacterial suspension.

26. The method of claim 19, further comprising, during growth of the test plant over the growth period:
measuring an oxygen concentration within the enclosed chamber of the plant culture system; and
activating a gas removal apparatus of the plant culture system to adjust the oxygen concentration according to a reference value for the test plant.

27. The method of claim 19, wherein at least one of the test plant and the support medium comprises at least one nitrogen-fixing bacterium.

28. The method of claim 27, further comprising determining a relative measurement of nitrogen fixation by the at least one nitrogen-fixing bacterium.

* * * * *

SEQUENCE LISTING

```
<160> NUMBER OF SEQ ID NOS: 8

<210> SEQ ID NO 1
<211> LENGTH: 500
<212> TYPE: DNA
<213> ORGANISM: Klebsiella sp.

<400> SEQUENCE: 1
agcgtcaggt accggtcatg attcaccgtg cgattctcgg ttccctggag cgcttcattg      60
gcatcctgac cgaagagttc gctggcttct tcccaacctg gattgcacca gtgcaggtag     120
tggtcatgaa tattaccgat tctcaggctg aatacgttaa cgaattgacg cgtaaactac     180
aaaatgcggg cattcgtgta aaagcagact tgagaaatga gaagattggc tttaaaatcc     240
gcgagcacac tttacgtcgt gtcccgtata tgttggtctg tggcgacaaa gaagtcgaag     300
ccggcaaagt ggccgtgcgc acccgtcgcg ggaaagacct cggcagcatg gacgtaagtg     360
aagtgattga gaagctgcaa caagagattc gcagccgcag tcttcaacaa ctggaggaat     420
aaggtattaa aggcggaaaa cgagttcaaa cggcacgtcc gaatcgtatc aatggcgaga     480
ttcgcgccct ggaagttcgc                                                 500

<210> SEQ ID NO 2
<211> LENGTH: 400
<212> TYPE: DNA
<213> ORGANISM: Klebsiella sp.

<400> SEQUENCE: 2
gcccgctgac cgaccagaac ttccaccttg gactcggcta taccttggc gtgacggcgc       60 gcgataactg ggactacatc cccattccgg tgatcttacc attggcgtca ataggttacg     120
gtccggcgac tttccagatg acctatattc ccggcaccta caataacggt aacgtttact     180
tcgcctgggc tcgtatacag tttaattcg ctaagtctta gcaataaatg agataagcgg      240
tgtgtcttgt ggaaaaacaa ggactaaagc gttacccact aaaaaagata gcgacttta     300 tcacttttta gcaaagttgc actggacaaa aggtaccaca attggtgtac tgatactcga     360
cacagcatta gtgtcgattt ttcatataaa ggtaattttg                           400
```

<210> SEQ ID NO 3
<211> LENGTH: 400
<212> TYPE: DNA
<213> ORGANISM: Klebsiella variicola

<400> SEQUENCE: 3

```
gcccgctgac cgaccagaac ttccaccttg gactcggcta taccottggc gtgacggcgc    60
gcgataactg ggactacatc cccattccgg tgatcttacc attggcgtca ataggttacg   120
gtccggcgac tttccagatg acctatattc ccggcaccta caataacggt aacgtttact   180
tcgcctgggc tcgtatacag ttttaattcg ctaagtctta gcaataaatg agataagcgg   240
tgtgtcttgt ggaaaaacaa ggactaaagc gttacccact aaaaaagata gcgacttttta  300
tcacttttta gcaaagttgc actgacaaa  aggtaccaca attggtgtac tgatactcga   360
cacagcatta gtgtcgattt ttcatataaa ggtaattttg                         400
```

<210> SEQ ID NO 4
<211> LENGTH: 313
<212> TYPE: DNA
<213> ORGANISM: Kosakonia sacchari

<400> SEQUENCE: 4

```
ggacatcatc gcgacaaaca atattaatac cggcaaccac accggcaatt tacgagactg    60
cgcaggcatc ctttctcccg tcaatttctg tcaaataaag taaagaggc agtctacttg   120
aattaccccc ggctggttga gcgtttgttg aaaaaaagta actgaaaaat ccgtagaata   180
gcgccactct gatggttaat taacctattc aattaagaat tatctggatg aatgtgccat   240
taaatgcgca gcataatggt gcgttgtgcg ggaaaactgc ttttttttga aagggttggt   300
cagtagcgga aac                                                     313
```

<210> SEQ ID NO 5
<211> LENGTH: 1997
<212> TYPE: DNA
<213> ORGANISM: Kosakonia sacchari

<400> SEQUENCE: 5

```
atgaccctga atatgatgat ggatgccggc ggacatcatc gcgacaaaca atattaatac    60
cggcaaccac accggcaatt tacgagactg cgcaggcatc ctttctcccg tcaatttctg   120
tcaaataaag taaagaggc agtctacttg aattaccccc ggctggttga gcgtttgttg   180
aaaaaaagta actgaaaaat ccgtagaata gcgccactct gatggttaat taacctattc   240
aattaagaat tatctggatg aatgtgccat taaatgcgca gcataatggt gcgttgtgcg   300
ggaaaactgc ttttttttga aagggttggt cagtagcgga acaactcac ttcacacccc   360
gaaggggaa gttgcctgac cctacgattc ccgctatttc attcactgac cggaggttca   420
aaatgaccca gcgaaccgag tcgggtaata ccgtctggcg cttcgatttg tcccagcagt   480
tcactgcgat gcagcgcata agcgtggtac tcagccgggc gaccgaggtc gatcagacgc   540
tccagcaagt gctgtgcgta ttgcacaatg acgcctttt gcagcacggc atgatctgtc   600
tgtacgacag ccagcaggcg attttgaata ttgaagcgtt gcaggaagcc gatcagcagt   660
taatccccgg cagctcgcaa atccgctatc gtccgggcga agggctggtc gggacggtgc   720
tttcgcaggg ccaatcatta gtgctggcgc gcgttgctga cgatcagcgc tttcttgacc   780
ggctcgggtt gtatgattac aacctgccgt ttatcgccgt gccgctgata gggccagatg   840
```

```
cgcagactttc ggtgtgctga cggcacaaca ccatggcgcg ttacgaagag cgattacccg     900
cctgcacccg ctttctggaa acggtcgcta acctggtcgc gcaaaccgtg cgtttgatgg     960
caccaccggc agtgcgccct tccccgcgcg ccgccataac acaggccgcc agcccgaaat    1020
cctgcacggc ctcacgcgca tttggttttg aaaatatggt cggtaacagt ccggcgatgc    1080
gccagaccat ggagattatc cgtcaggttt cgcgctggga caccaccgtt ctggtacgcg    1140
gcgagagtgg caccggcaag gagctgattg ccaacgccat ccaccaccat cgccgcgtg     1200 ccggtgcgcc atttgtgaaa ttcaactgtg cggcgctgcc ggacacactg ctggaaagcg    1260
aattgttcgg tcacgagaaa ggggcattta ccggcgcggt acgccagcgt aaaggccgtt    1320
ttgagctggc cgatggcggc acgctgtttc ttgacgagat cggcgagagt agcgcctcgt    1380
ttcaggctaa gctgctgcgc attttgcagg aaggcgaaat ggaacgcgtc ggcggcgacg    1440
agacattgca agtgaatgtg cgcattattg ccgcgacgaa ccgcaatctt gaagatgaag    1500
tccggctggg gcactttcgc gaagatctct attatcgcct gaatgtgatg cccatcgccc    1560
tgccgccact acgcgaacgc caggaggaca ttgccgagct ggcgcacttt ctggtgcgta    1620
aaatcgccca taaccagagc cgtacgctgc gcattagcga gggcgctatc cgcctgctga    1680
tgagctacaa ctggcccggt aatgtgcgcg aactggaaaa ctgccttgag cgctcagcgg    1740
tgatgtcgga gaacggtctg atcgatcggg atgtgatttt gtttaatcat cgcgaccagc    1800
cagccaaacc gccagttatc agcgtctcgc atgatgataa ctggctcgat aacaaccttg    1860
acgagcgcca gcggctgatt gcggcgctgg aaaaagcggg atgggtacaa gccaaagccg    1920
cgcgcttgct ggggatgacg ccgcgccagg tcgcctatcg tattcagacg atggatataa    1980
ccctgccaag gctataa                                                   1997

<210> SEQ ID NO 6
<211> LENGTH: 2751
<212> TYPE: DNA
<213> ORGANISM: Klebsiella variicola

<400> SEQUENCE: 6
tgaaaagccg cgcccgcccg gcttttttat tagatagttt tttcttatgg tgacgcgatg      60
agcaactcat tacctgacac agcctcccct cttctgcccg tcccgccgga acatccggtg     120
agctggccgc agggcgatct gaactgtgct gcaattaagg cgcacatcga taccttccag     180
cactggctgg gcgaggcgtt tgactccggc atcgccgcgg agcagctcat tgcggcgcgc     240
accgaattta tcgaccagct gctgcagcgg ttgtggatcg cctacggttt tgaatccgtc     300
tgcgatctgg cgctggtggc cgtccttgat tatggccgcg gcgagctgca cccgctctct     360
gacgtcgcac tgctgatcct cagccgcaaa aaactgcctg acgaccaggc gcaaaaggtc     420
ggcgaactgc tgacgctact gtgggacgtc aagctggagg tgggccacag cgtgcgcacc     480
ctcgaagagt gtctgctcga aggactttcg gatctcaccg tcgccactaa cttgattgaa     540
tcgcgcctgc tgatcggcga cgtcgcgctg ttccttgaac tgcaaaaaca tatttttagc     600
gacggcttct ggccatcgga aaagttcttc gccgccaagg tggaagagca gaacgtccgt     660
catcaacgct atcacggcac cagctataac ctggagccgg acgtgaaaag cagcccggc      720 ggcctgcggg atatccatac gctacagtgg gtggctcgcc gtcattttgg cgccacctcg     780
atggatgaga tggtcggctt cggctttctg accgaagccg agcgcaatga gctcaacgag     840
tgtctgcatc agctgtggcg catccgtttc gcgctgcatc tcgagctcac tcgctatgac     900
aaccgtctgc ttttcgaccg ccagctcagc gtcgcccgcc ggctcggcta tgaaggcgac     960
```

```
ggcaaccagc cgattgagca tatgatgaag gacttcttcc gcgtcacccg ccgggtgagc    1020
gagctgaacc agatgctgct tcagctgttt gaagaggcta ttctcgccct gaccgaggat    1080
gaaaaaccgc gcccgataga cgatgacttc cagctgcgcg gcacccttat cgatctgcgt    1140
gacgacacgc tgtttattcg cgaaccgcag gccattctgc gcatgtttta tatgatggtg    1200
cgcaacagca ctatcaccgg catctactcc acgacgttgc gccatctgcg ccatgcccgg    1260
cgccatctga cccagccgct gtgctatatc cggaggcgc gcacgctctt tctcagcatg     1320
ctgcgccatc aggggcggt cagccgcgga ctgctgccga tgcatcgcca tagcgtgctg     1380
tgggcctata tgccgcagtg gtcacatatc gtcggccaga tgcagttcga tctgtttcac    1440
gcctacaccg tcgatgaaca caccatccgc gtgatgctga agctggagag ctttgccaaa    1500
gaagaaaccc gcagccgcca cccgctgtgc gtggagctat ggccgcgctt aacgcacccg    1560
gagctgattt taatcgccgc cctgttccac gacattgcga aagggcgtgg cggcgaccac    1620
tcgatcctcg gcgcgcagga tgtgctgaag tttgccgagc tgcacggact gaactctcgc    1680
gaaacgcagt tggtcgcctg gctggtgcgt caccatctgc tgatgtcggt caccgcccag    1740
cggcgcgaca ttcaggatcc ggaggtgatt aagcagttcg ccgaggaagt gcaaacggaa    1800
aatcgcctgc gctatctggt gtgcctgacc gtcgccgaca tctgcgccac caacgaaacg    1860
ctgtggaaca gctggaagca gagtctgctg cgcgaactct atttcgccac cgagaaacag    1920
ctgcgtcggg gcatgcaaag caccccggat atgcgcgaac gggtgcgtca tcatcagctg    1980
caggcgctgg ccctgctgcg gatggacaat attaatgaag aggcgctgca tcagatctgg    2040
aaccgctgcc gcgccaacta tttcgtgcgg catacgccga cgcagctcgc ctggcacgcc    2100
cgcaacctgc tgcgtcacga tctgaataag ccgatgattc tgctgagttc gcaggccacc    2160
cgcggcggta cggagatttt tatctggagc ccggatcgcc cttatctgtt tgccgcggtg    2220
tgcggcgaac tggaccgccg caacctcagc gtccacgacg cgcagatctt caccacccgc    2280
gacggcatgg cgatggatac ctttattgtc ctcgaacccg acggcagccc gctttccgct    2340
gaccgccacg acgcgattcg ccacggtctt gaacagacga taactcagcg cagctgggaa    2400 ccccggccc cgcgtcgtca ggcggcaaaa ctgcgtcact tctctgtgcc gacagaggtg     2460
aatttcctgc cgacccatac cgatcgaaaa tcgtttctcg agctgattgc gctcgatcag    2520
ccagggctgc tcgcccgcgt cggccaggtg ttcgccgacc tcggtatttc gcttcacggg    2580
gcgcgaatta cgacaattgg tgagcgagta aagatttat ttataatcgc caccgccgac     2640
cggcgtggcc ttaataatga gctacaacaa gaagtgcaac aacggttgac agaggccctc    2700
aatccaaacg ataaagggtg acgtatttt tttagtgaat ggaaagaaac a              2751
```

<210> SEQ ID NO 7
<211> LENGTH: 1410
<212> TYPE: DNA
<213> ORGANISM: Klebsiella variicola

<400> SEQUENCE: 7

```
atgcaacgag ggatagcctg gatcgttgat gacgatagct ccatccgctg ggtgcttgaa      60
cgcgcgctca ccggagccgg cttgagctgc acaacgttcg aaagcggcaa tgaggtgcta     120
gatgccctca ccaccaaaac cccggatgta ctgctgtcag ctatccgtat gccgggaatg     180
gatggtctgg cgctgctcaa acagattaag cagcgtcatc caatgcttcc ggtcatcata     240
atgaccgcac attccgatct ggacgctgcg gtcagcgctt atcagcaagg cgcgtttgat     300
```

```
tatctgccca aacctttga tattgatgaa gccgtcgccc tggtcgaccg ggcgataagc    360
cactatcagg agcagcaaca gccgcgaaat gcgccaataa gcagcccaac tgccgacatc    420
atcggcgaag cgccggcaat gcaggatgtc tttcgcatta ttggccgttt gtcgcgatca    480
tccatcagcg tgctgattaa tggcgaatcc ggtaccggta aagagctcgt cgctcacgcc    540
ctgcatcgtc atagcccacg ttcaaaagcg ccgtttatcg cactgaatat ggcggcaata    600
cccaaagacc tgattgagtc cgagctgttc gggcatgaaa aagggggcctt taccggcgcc    660 aataccgtcc gccagggacg cttcgaacag gctgacggcg gcacgctatt cctggatgaa    720
attggcgata tgccgcttga tgtccagact cgtctgctgc gcgtgctggc ggatggccag    780
ttttatcgcg tgggcggtta cgcgccggtg aaggtcgatg tgcggatcat cgccgccacc    840
caccagaacc tggaacagcg cgtgcaggag gggaaattcc gtgaagattt gttccaccgc    900
ctgaacgtga tccgggtgca tttaccgccg ctgcgcgagc gccgggaaga tattccacgc    960
ctggcccgcc attttctgca gatagccgcc cgcgagctcg gtgttgaagc caaacagctg   1020
catccggaaa cggagacagc gctgacacgc ctggcgtggc ctggcaacgt ccgtcagctg   1080
gaaaacacct gtcgctggct caccgtcatg gccgccggcc aggaggtact gacgcaggat   1140
ctgccgagcg aactgtttga gactacggtt ccggacagcc cgacgcagat gcagcccgac   1200
agctgggcga cgctgctggg tcagtgggcc gatcgggcgt tgcgatccgg tcatcaaaac   1260
ctgctctcag aagcgcaacc cgaaatggag cgcacgctgc tgacgaccgc cctgcgccat   1320
acccaggggc acaagcagga ggctgcgcgt ctgctgggat ggggtcgtaa taccctgacg   1380
cgtaagctaa aagagctggg aatggagtag                                    1410
```

<210> SEQ ID NO 8
<211> LENGTH: 9
<212> TYPE: PRT
<213> ORGANISM: Artificial
<220> FEATURE:
<223> OTHER INFORMATION: synthetic polypeptide

<400> SEQUENCE: 8

Leu Ala Gly Leu Ile Asp Ala Asp Gly
1               5